(12) United States Patent
Terman

(10) Patent No.: US 6,340,461 B1
(45) Date of Patent: Jan. 22, 2002

(54) SUPERANTIGEN BASED METHODS AND COMPOSITIONS FOR TREATMENT OF DISEASES

(76) Inventor: David Stephen Terman, 3183 Palmero Way, Pebble Beach, CA (US) 93953

( * ) Notice: Subject to any disclaimer, the term of this patent is extended or adjusted under 35 U.S.C. 154(b) by 0 days.

(21) Appl. No.: 08/992,877

(22) Filed: Dec. 17, 1997

Related U.S. Application Data

(60) Provisional application No. 60/033,172, filed on Dec. 17, 1996, and provisional application No. 60/044,074, filed on Apr. 17, 1997.

(51) Int. Cl.⁷ .................. A61K 39/385; A61K 39/00; A61K 39/39; A61K 45/00; C12N 15/09; C12N 15/12; C12N 15/62; C12N 15/63

(52) U.S. Cl. .................. 424/193.1; 424/192.1; 424/194.1; 424/277.1; 424/278.1; 424/280.1; 424/282.1; 435/68.1; 435/69.1; 435/69.3; 435/69.7

(58) Field of Search .................. 424/277.1, 193.1, 424/194.1, 192.1, 278.1, 280.1, 282.1; 435/68.1, 69.7, 69.3, 69.1

(56) References Cited

PUBLICATIONS

Wong, S.S. In Chemistry of Protein Conjugation and Cross Linking CRC Press (1991) pp. 1–5 and Contents Pages (12 pages).*

Litton Et Al Eur. J. Immunol. 1996. vol. 26:1–9.*

* cited by examiner

*Primary Examiner*—Geetha P. Bansal
(74) *Attorney, Agent, or Firm*—Venable; Shmuel Livnat

(57) ABSTRACT

The present invention relates to therapeutic methods and compositions employing superantigens. Methods and compositions employing superantigens and immunotherapeutic proteins in combination with one another have been found to provide more effective treatment than either component used alone. Superantigens, in conjunction with one or more additional immunotherapeutic antigens, may be used to either induce a therapeutic immune response directed against a target or to inhibit a disease causing immune response. Specific combinations of superantigens and immunotherapeutic antigens are used to treat specific diseases. The induction (or augmentation) of a desired immune against a target may be used, for example, to kill cancer cells or kill the cells or an infectious agent. The inhibition of an immune response, e.g., through the induction of T cell anergy, may be used to reduce the symptoms of an autoimmune disease. Diseases that may be treated by the methods and compositions of the invention include neoplastic diseases, infectious diseases, and autoimmune diseases. One aspect of the invention is to provide methods for the treatment of diseases comprising the steps of administering an effective amount of a superantigen and an immunotherapeutic so as to have the desired therapeutic effect. The superantigen and immunotherapeutic antigen may be administered together as a mixture. Alternatively, the superantigen and immunotherapeutic antigen may be administered separately. In one embodiment of the invention, the superantigen and immunotherapeutic antigen are administered to the patient in the form of a immunotherapeutic antigen-superantigen polymer of the invention. Another aspect of the invention is to provide methods for the treatment of diseases comprising the steps of incubating a lymphocyte population ex vivo a superantigen and an immunotherapeutic protein so as to either activate or anergize T cells within the selected population.

7 Claims, 8 Drawing Sheets

MART-1 Peptide

N-Terminal Serine Added (or threonine)

MART-1 Peptide Labeled with N-Terminal Serine

Oxidation to N-Terminal Aldehyde with Release of Formaldehyde

MART-1 Peptide

SUPERANTIGEN BASED METHODS AND COMPOSITIONS FOR TREATMENT OF DISEASES

This application claims benefit of Provisional applications Ser No. 60/033,172 filed Dec. 17, 1996 and Ser. No. 60/044,074 filed Apr. 17, 1997.

FIELD OF THE INVENTION

This invention in the field of immunology, more particularly the therapeutic use of superantigens.

BACKGROUND ART

The immune system plays a central role in both preventing and causing many diseases. It is of interest to provide methods and compositions for the induction of immune response directed against harmful cells and viruses. Similarly, it is of interest to provide methods and compositions to inhibit unwanted immune responses in autoimmune diseases such as rheumatoid arthritis or transplanted organ rejection. Superantigens, such as some bacterial enterotoxins, have been found to have profound effects on the proliferation of T cell populations. The invention described herein relates to methods and compositions for using superantigens to exert desirable therapeutic effects on the immune system.

Many superantigens are bacterial enterotoxins. The staphylococcal enterotoxins comprise a family low molecular weight proteins which share common physico-chemical properties. They are the most potent T-cell mitogens known being capable of activating a resting T-cell population in concentrations of $10^{-13}$ molar. Compared to a conventional antigen which may activate 1/3000 T-cells, enterotoxins may evoke proliferation in up to 30% of a resting T-cell population. The enterotoxins are members of a group of proteins known as superantigens which share the common property of binding to T-cell Vβ receptors without the need for additional diversity elements resulting in massive lymphoproliferation, cytotoxic T-cell generation and lymphokine secretion (Bergdoll, M. S., Academic Press, London. (1983), Marrack, P., et al., Science, 248:750, (1990), Kotzin, B. L., et al., Advances in Immunology, 54:99, (1993), Drake, C.G., et al., J. Clinical Immunology, 18:12, (1992), Herman, A., et al., Annu. Rev. Immunol. 9:745, (1993), Scherer, M. T., et al., Annu. Rev. Cell Biology, 9:101–28, (1993), Terman, D. S., Cancer Research Institute, New York, N.Y., June (1993)).

Recent studies have shown that several enterotoxins are capable of inducing antitumor effects against established rodent melanoma, sarcoma and carcinoma when given parenterally Mokyr, M. B., et al., *J Immunol.*, 151:4838, (1993), Weiner, G. J., et al., *J. Immunol.*, 152:2385, (1994), Wallgren, A., et al., Blood, 31:1230 (1993), Rubin, M., et al., *J. Immunol.*, 152:3522, (1994), Lando, P. A., et al., *Cancer Immunol. Immunother.*, 33:231, (1991), Dohlsten, M., et al., Immunology, 97:520, (1993), Dohlsten, M., et al., *Proc. Nat. Acad. Sci. USA,* 88:9287, (1991), Dohlsten, M., et al., Proc. Nat. Acad. Sci., 91:8945, (1994), Dohlsten, M., et al., Int. J. Cancer, 54:482, (1993), Lando, P. A., et al., *Cancer Immunol. Immunother.*, 36:223, (1993), Penna, C., et al., Cancer Research, 54:2738, (1994), Kalland, T., et al., *Med. Oncol. & Tumor Pharmacother.*, 10:37, (1993), Newell, K. A., et al., *Proc Nat'l. Acad. Sci. USA* 88:1074 (1991), Ochi, A., et al., *J. Immunol.* 151:3180 (1993), Hedlund, G., et al., *Cancer Immunol. Immunother.* 36:89 (1993)).

In view of the numerous shortcomings with various currently available methods and compositions for the treatment of multiple neoplastic diseases, infectious disease, and autoimmune diseases, it of interest to provide new methods and compositions for the treatment of such diseases. The invention described herein relates to methods and compositions for using superantigens to exert desirable therapeutic effects on the immune system

SUMMARY OF THE INVENTION

The present invention relates to therapeutic methods and compositions employing superantigens. Methods and compositions employing superantigens and immunotherapeutic proteins in combination with one another have been found to provide more effective treatment than either component used alone. Superantigens, in conjunction with one or more additional immunotherapeutic antigens, may be used to either induce a therapeutic immune response directed against a target or to inhibit a disease causing immune response. Specific combinations of superantigens and immunotherapeutic antigens are used to treat specific diseases. The induction (or augmentation) of a desired immune response against a target may be used, for example, to kill cancer cells or kill the cells of an infectious agent. The inhibition of an immune response, e.g., through the induction of T cell anergy, may be used to reduce the symptoms of an autoimmune disease. Diseases that may be treated by the methods and compositions of the invention include neoplastic diseases, infectious diseases, and autoimmune diseases.

One aspect of the invention is to provide methods for the treatment of diseases comprising the steps of administering an effective amount of a superantigen and an immunotherapeutic so as to have the desired therapeutic effect. The superantigen and immunotherapeutic antigen may be administered together as a mixture. Alternatively, the superantigen and immunotherapeutic antigen may be administered separately. In one embodiment of the invention, the superantigen and immunotherapeutic antigen are administered to the patient in the form of a immunotherapeutic antigen-superantigen polymer of the invention.

Another aspect of the invention is to provide methods for the treatment of diseases comprising the steps of incubating a lymphocyte population ex vivo with a superantigen and an immunotherapeutic protein so as to either activate or anergize T cells within the selected population. The treated lymphocytes could then be introduced into a patient so as to have the desired therapeutic effect. The superantigen and immunotherapeutic antigen may be administered together as a mixture. Alternatively, the superantigen and immunotherapeutic antigen may be administered separately. In one embodiment of the invention, the superantigen and immunotherapeutic antigen are incubated with the lymphocyte population in the form of an immunotherapeutic antigen-superantigen polymer of the invention.

Another aspect of the invention is to provide immunotherapeutic antigen-superantigen polymers that comprise a first subunit that is a superantigen and a second subunit that is an immunotherapeutic antigen. The first and second subunits may be joined together either directly or indirectly through the use of crosslinking agents. The subunits may be joined together either covalently or non-covalently. The invention also provide methods of making a immunotherapeutic antigen-superantigen polymer useful for the treatment of various disease and immunotherapeutic antigen-superantigen polymers made by the subject methods; these methods involve the step of joining a superantigen and an immunotherapeutic protein to one another, especially through the use of crosslinking agents. In other embodiments of the invention, the immunotherapeutic antigen-superantigen polymers are recombinant chimeric proteins that comprise superantigen portions and immunotherapeutic antigen portions. Other embodiments of the invention include vectors and host cells for the recombinant production of the subject chimeric proteins.

Another aspect of the invention is to provide superantigen containing formulations for the treatment of neoplastic diseases, infectious diseases, and autoimmune diseases. The subject composition comprise either (I) a mixture of a superantigen and an immunotherapeutic antigen or (ii) a immunotherapeutic antigen-superantigen polymer of the invention. The subject formulations may further comprise carriers and excipients. The formulations of the invention may be adapted for a wide variety of methods of administration. In additional embodiments of the invention, the formulations may be encapsulated in liposomes.

DESCRIPTION OF THE SPECIFIC EMBODIMENTS

Figure 1:
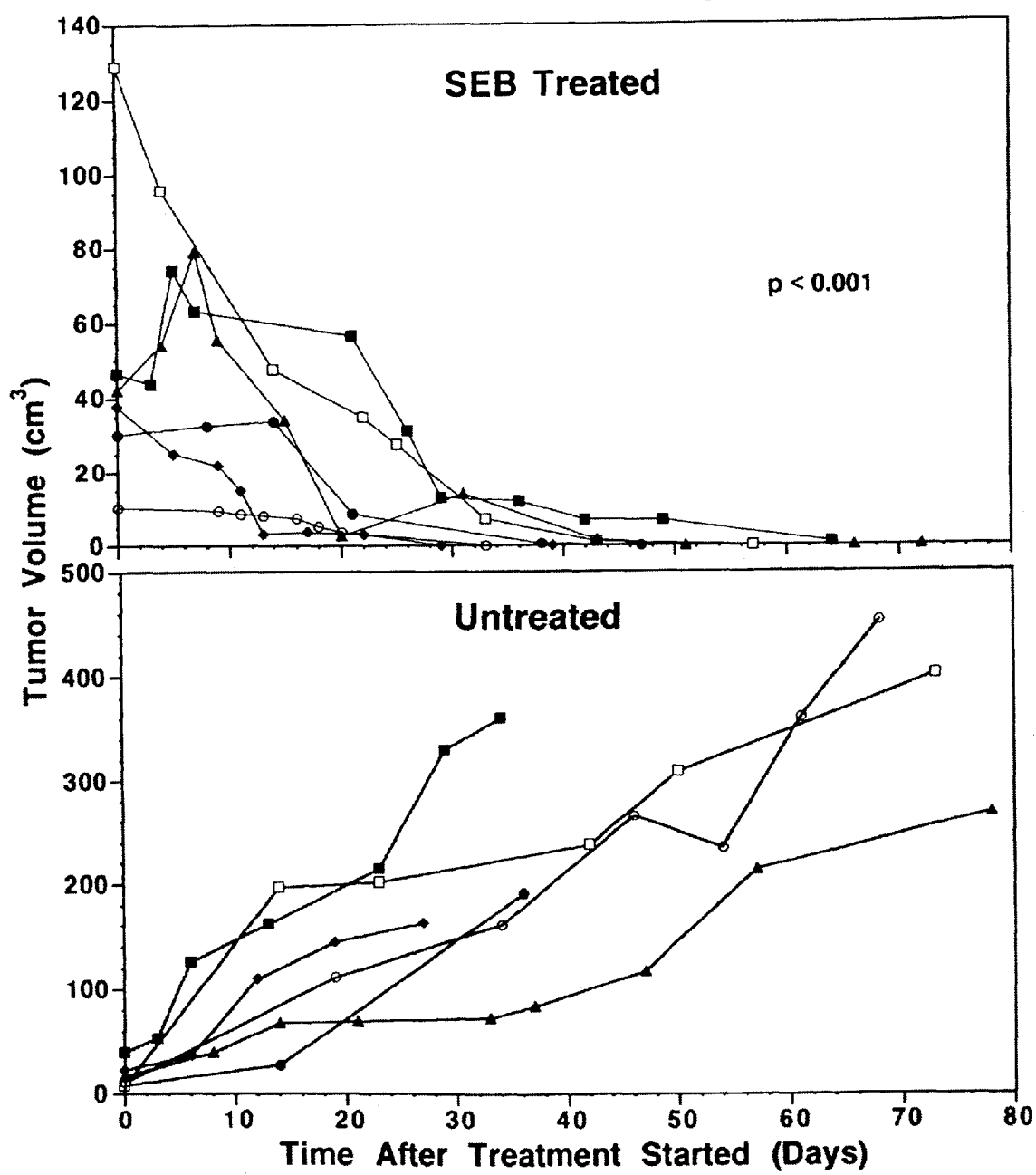
FIG. 1 shows the results of an experiment using a rabbit carcinoma (VX-2) model in which the rabbits are treated with SEB.

The present invention provides therapeutic methods and compositions employing superantigens. The present invention relates to the discovery that methods and compositions employing superantigens and immunotherapeutic proteins in combination with one another have been found to be more effective for disease treatment than either component used alone. The present invention provides compositions comprising superantigens and immunotherapeutic antigens useful for treating a subject with an autoimmune, infectious or a neoplastic disease. Preferably the superantigens and immunotherapeutic are joined to each other in the form of a polymer. Autoimmune (or other immune-related diseased) which may be treated include but are not limited to idiopathic thrombocytopenic purpura, rheumatoid arthritis, systemic lupus erythematosus, multiple sclerosis, transplant rejection, paraneoplastic syndrome, hemolytic anemia. A more complete, though not exhaustive, list of autoimmune diseases treatable by the present invention appears in Catalogue 1. Tumors treatable by this invention encompass carcinomas of breast, lung, colon, kidney, melanomas, lymphomas, but may also include any and all neoplastic processes.

When practicing certain embodiments of the invention, the characterization of the magnitude and quality of the immune responses to each of these reagents facilitates the design of novel therapeutic compositions and methods for treating neoplastic, autoimmune and infectious diseases. For example, in infectious diseases and cancer it is desirable to augment T cell response with peptides (immunotherapeutic antigens) and superantigens or conjugates thereof whereas in autoimmune disease it is desirable to induce specific anergy in T cells which control or suppress the autoimmune response. Anergy or sensitization of a given clone of T cells may be produced depending on the dose and timing of administration of the peptide and superantigen. The immunotherapeutic antigen-superantigen polymers of the invention may also be used to provide for similar in vitro activation of T cell clones in autoimmune, neoplastic and infectious diseases. Alternatively, the subject immunotherapeutic antigen-superantigen polymers may be given parenterally to the host. Adjustments of the ratios of peptide to superantigen in the subject immunotherapeutic antigen-superantigen polymers may be used to provide for either sensitization or anergy of T cell clones as desired. The present invention also includes the use of superantigens conjugated to various chemicals such as porphyrins which may selectively localize in tumor based on their affinity for tissues with increased metabolic activity for use in the treatment methods of the invention.

The terms "immunotherapeutic antigen-superantigen polymer" or "oligomer" are used interchangeably herein to refer to a molecular entity comprising of a first and second monomeric unit. The first monomer is a superantigen. The second monomer is an immunotherapeutic antigen. The monomers are preferably covalently bonded, more preferably crosslinked. The terms "immunotherapeutic antigen-superantigen polymer" and "crosslinked polymer" are intended to include immunotherapeutic antigen-superantigen polymers in which the subunits are bonded "end to end" as well as immunotherapeutic antigen-superantigen polymers that comprise randomly joined subunits. It is understood that such crosslinked immunotherapeutic antigen-superantigen polymers or oligomers may include additional atoms not native to the protein or peptide and which are derived from the crosslinking agent.

In the immunotherapeutic antigen-superantigen polymers of the present invention, the individual monomeric units are preferably randomly linked, such that any given immunotherapeutic antigen-superantigen polymeric structure may contain a variable number and variable structural arrangement of monomers. However, the total amount of peptide in the final composition is preferably in the ranges delineated herein.

The present invention relates to the discovery that the clinical effects of an activated T cell preparation are related in part to the amount of superantigen used alone or complexed with tumor peptides. Ratios of immunotherapeutic antigens to superantigen of about 1000 (by weight) may be used to produce antitumor effects. In contrast, ratios >1000, with superantigen in quantities >1 ng/ml, by inactivating T cells may not result in antitumor effects. Superantigen in intermediate amounts, between 1 ng/ml and 1 g/ml may result in T-cell desensitization and anergy. Indeed, according to the present invention, the therapeutic effect of immunotherapeutic antigens and superantigens for the treatment of autoimmune diseases is due, in part to, the induction of T-cell anergy by enterotoxin (or other superantigens).

The immunotherapeutic antigen-superantigen polymers may be produced by recombinant means, for example in the form of fusion proteins or as products of sequentially arranged genes that encode a protein having more than one unit of peptide (or a fragment or derivative thereof) or one or more units of peptide and one or more units consisting of all or a fragment of another protein such as a bacterial superantigen. Hence, immunotherapeutic antigen-superantigen polymers made by recombinant methods (rather than by chemical means) are included herein.

By utilizing purified peptides as immunotherapeutic antigens, embodiments of this invention may avoid the use of non-specific whole tumor cells or irradiated tumor cells. This allows for a more reliable immunizing preparation and avoids the use of cumbersome and heterogeneous cell populations, which may express a large number of surface antigens with incomplete expression of the desired Vβ. The T-cells activated and expanded by peptide-superantigen preparations are then infused into patients with cancer or autoimmune disease. The infused cells contain very low or minimal amounts of the superantigen. The enriched T-cells with tumor specificity may then target and destroy tumor cells in vivo after infusion into tumor bearing hosts.

Imnmunotherapeutic antigen-superantigen polymers may also be produced by transfecting tumor cells with superantigen genes to permit expression of both tumor associated antigens and superantigen on the same cell surface. To further augment the immunogenicity of the tumor cell, selected tumor cells, selected tumor antigen genes, as well as class I histocompatibility genes and B7 genes, may be cotransfected with the superantigen gene into tumor cells.

Moreover, the present invention provides for the reconstitution of deleted Vβ bearing T cell clones with stem cells that have been genetically engineered to produce the missing Vβ segments by transfection with Vβ encoding polynucleotides in the appropriate vectors. Immunization of these virgin stem cells with tumor specific antigen may be used to produce a tumor specific T cell clone, which in turn, may be used to produce a T cell hybridoma or expanded T cell population. The sustained growth of selected Vβ bearing clones may be stimulated using the appropriate superantigens.

Superantigens

The term "superantigen" as used herein refers broadly to those proteins that are generally recognized to have the properties of superantigens, e.g., the ability to stimulate proliferation a large set of CD4+ T cells by binding to certain Vβ segments of T cell receptors, irrespective of the presence of an antigen on the T cell receptor. Detailed descriptions of the effect of superantigens on T cells can be found, among other places, in (Berg doll, M. S., Academic Press, London. (1983), Marrack, P., et al., Science, 248:750, (1990), Kotzin, B. L., et al., Advances in Immunology, 54:99, (1993), Drake, C. G., et al., J. Clinical Immunology, 18:12, (1992), Hennan, A., et al., Annu. Rev. Immunol, 9:745, (1993), Scherer, M. T., et al., Annu. Rev. Cell Biology, 9:101–28, (1993), Terman, D. S., Cancer Research Institute, New York, N.Y., June (1993)). The term "superantigen" as used herein refers not only to naturally occurring superantigens, but also to various derivatives of naturally occurring superantigens that have the same effects on lymphocytes as naturally occurring superantigens. Such derivative of naturally occurring superantigens may readily be designed by making use of amino sequence homology information between known superantigens, computer-aided molecular designs, combinatorial design, the use of anti-idiotypic antibodies corresponding in structure to superantigens, and like techniques. Many bacterial enterotoxin have been recognized to be superantigens. In a preferred embodiment, one or more bacterially derived superantigens, preferably enterotoxin, are present in the therapeutic composition. These enterotoxins may be produced recombinantly, by chemical synthesis of purified from native sources, using methods known in the art. See, for example, Ranelli, D. M. et al., *Proc. Nat'l. Acad Sci. USA* 82:850–854 (1985); Iandolo, J. J. *Annu. Rev. Microbiol.* 43:375 (1989); Kappler, J. W. et al., *J. Exp. Med.* 175:387 (1992); Rahim, A. et al., *J. Exp. Med.* 180:615 (1994;Lando, P. A. et al., *Canc. Immunol. Immunother.* 33:231 (1991) Dohlsten, M. et al., 88:9287 (1991); Dohlsten, M. et al., *Immunology* 79:520 (1993); Dohlsten, M. *Proc. Nat'l. Acad. Sci. USA* (1994); Marrack, P. et al., *Science* 248:750 (1990); and Terman, D. S. et al., PCT Publication WO91/10680 (1991).

Various enterotoxins will activate T-cells with specific TCR Vβ phenotypes. This relationship between the specific superantigen and the TCR Vβ phenotypes should be taken into account when choosing specific combinations of superantigens and immunotherapeutic antigens. For example, $SEC_1$ activates T-cell clones with TCR Vβ phenotypes that are identical to those which appear in some melanoma specific TIL (tumor infiltrating lymphocytes) Hence, once the specific clonality or Vβ phenotype of the T-cells activated by tumor specific peptide has been identified, a superantigen known to activate that Vβ phenotype may be used to further enrich and expand the presensitized T-cell population. (Bergdoll, M. S., Academic Press, London, (1983), Marrack, P., et al., Science, 248:750, (1990), Kotzin, B. L., et al., Advances in Immunology, 54:99,(1993), Drake, C. G., et al., J. Clinical Immunology, 18:12, (1992), Herman, A., et al., Annu. Rev. Immunol., 9:745, (1993), Scherer, M. T., et al., Annu. Rev. Cell Biology, 9:101–28, (1993)).

Most preferred superantigens are *Staphylococcus aureus* enterotoxins A, B, C1, C2, D or E (SEA, SEB, SEC1, SEC2, SED, SEE). Examples of other preferred enterotoxins or superantigens are: *Streptococcus pyogenes toxins A and C (SPE-A and SPE-C; Staphylococcus aureus* toxic shock syndrome-associated toxin (TSST-1); *Staphylococcus aureus* exfoliating toxins A and B (ETA and ETB) and *Staphylococcus aureus* alpha toxin. Also included are toxins from *Mycoplasma arthritides* and *Yersinia enterocolitica*. Various enterotoxins share differing degrees of immunological relatedness (Bergdoll, M. S. et al., *Infect. Immun.* 4:593 (1971); Bergdoll, M. S., *Enterotoxins.* In: STAPHYLOCOCCI AND STAPHYLOCOCCI INFECTIONS, C. S. F. Easmon et al., eds, pp. 559–598, 1983, London, Academic Press; Freer, J. H. et, *J. Pharmacol Pharm. Ther.* 19:55 (1983). Immunologic cross-reactivity between SPE-A, SEB and SEC1 suggests the presence of a conserved domain. SEA, SEB, SEC, SED, TSST-1 and the pyrogenic exotoxins share considerable DNA and amino acid sequence homology. Overall there are several stretches of protein having similarities throughout the total group of Staphylococcal enterotoxins, Streptococcal pyrogenic exotoxins and Staphylococcal exfoliative toxins. The structural homologies between the enterotoxins and the S. *pyogenes*, toxins, above, apparently are responsible for the identity of clinical responses to them. These toxins induce hypotension, fever, chills and septic shock in humans, apparently by inducing cytokines such as interleukin-1, interleukin-2, tumor necrosis factors, interferons and procoagulant activity which are the prime mediators of the clinical symptoms. Additional agents which are candidates for use in accordance with this invention in place of an enterotoxin, based upon structural homology or identity of clinical effects, are gram positive bacterial products, cell wall bacterial constituents such as peptidoglycans and various gram negative bacterial components including products of Meningococci, Pseudomonas and *E. coli*.

Various naturally occurring surface molecules, viruses and peptides may bear a striking sequence homology to the Staphylococcal enterotoxins to account for their superantigenic properties. Examples of these include the mammary tumor virus, minor lymphocyte stimulating loci, naturally occurring heat shock proteins, as well as numerous species of mycoplasma and mycobacterium, rabies nucleocapsid and Epstein-Barr virus. These peptide sequences with superantigenic properties may exert powerful antitumor effects similar to the native enterotoxins and therefore may be considered superantigens for the purpose of the invention.

Mouse mammary tumor viruses are retroviruses that are found either as free virus particles transmitted from mother to pup in milk or as integrants in mouse genomes, transmitted in the germ line from parents to their progeny. MTV's each encode a superantigen (vSAG) in the 3 long terminal repeats of their DNA. Like the bacterial superantigens, the vSAGs act by binding to class II molecules, then engaging the T cell receptor Vβ and thus activating T cells. vSAG associated with any I-E class II protein react well with T cells. vSAGs are also stimulatory with some I-A class II proteins. The vSAG's consist of a family of proteins 317–321 amino acids in length which is highly conserved except for the last 30 residues. The promoter is contained within the 5 LTR and contains a glucocorticoid-inducible transcriptional enhancer element.

vSAG proteins contain four glycosylation sites and have a molecular weight of about 37K to 45K. They are transported into microsomes as type II transmembrane proteins, i.e. with their N termini in the cytoplasm and extracellular C terminus. The C terminus is important for superantigen function and residues 190–200 are partly responsible for Vβ specificity.

The vSAG proteins can be grouped according to homology at the 3' end and these groupings correlate with known Vβ specificities. Five different subfamilies of vSAG have been discovered bearing Vβ6, 7, 8.1 and 9; Vβ7; Vβ3; Vβ5, 11 and 12; or Vβ 14 and 15.

Immunotherapeutic Antigens

The term "immunotherapeutic antigen" as used herein refers to a broad range of molecules that when used in conjunction with a superantigen in accordance with the methods and compositions of the invention, can produce a desirable therapeutic effect. A given molecule is said to be an "immunotherapeutic antigen" with respect to a specific disease or set of diseases. Immunotherapeutic antigens are usually proteins, but may belong to other classes of macromolecules, such as carbohydrates, nucleic acids, and the like. Immunotherapeutic antigens bind to the T cell receptors of a lymphocyte population that would either (i) produce a desirable therapeutic if stimulated, e.g., as in cancer treatment, or (ii) produce desirable therapeutic effects if anergized, e.g., as in autoimmune disease treatment. Exemplary, but not exclusive of, categories of immunotherapeutic antigens are (1) tumor antigens, (2) pathogenic organism antigens, (3) autoimmune antigens. Immunotherapeutic antigens may be obtained from natural sources or from host cell genetically engineered to produce the immunotherapeutic antigen. In embodiments of the invention employing immunotherapeutic antigens that are relatively small polypeptides, the immunotherapeutic antigen may be synthesized in vitro using techniques well known to the person skilled in the art.

One category of immunotherapeutic antigen is the tumor antigen. The term "tumor antigen" refers to tumor associated antigens (TAA) and other peptides that are capable of evoking an immune response in the host (Reisfeld et al., *Adv. Immunol.* 1991). These antigens also include mutated products of various oncogenes and P53 genes which are expressed in tumor cells. Common melanoma antigens recognized by T lymphocytes have been identified and may be used as immunotherapeutic antigens. Five genes coding for different melanoma antigens have been identified. For example, MAGE 1 and 3, expressed on melanoma and other tumor cells, are recognized by CTL in the context of HLA-A1 (Van der Bruggen, P., et al., Science, 254:1643, (1991), Gauler, B., et al., J. Exp. Med., 179:921, (1994)). They were identified by T cell clones from peripheral blood of patients who were immunized with mutagenized tumor. MART-1 (identical to Melan-A) (Kawakami, Y., et al., *Proc. Nat'l. Acad. Sci.,* 91:3515, (1994), Coulie, P. G., et al., J. Exp. Med., 180:35, (1994)), gp100 (Kawakami, Y., et al., *Proc. Nat'l. Acad. Sci.,* 91:6458, (1994)), and tyrosinase (Brichard, V., et al., J. Exp. Med., 178:48, (1993)) are melanocyte lineage-related antigens expressed on both melanoma and melanocytes. MART-1 and gp100 have been shown to be recognized by MHC-class I-restricted CTL in the context of HLA-A2, and tyrosinase in the context of HLA-A2 and HLA-A24 (Robbins, P. F., et al., Cancer Res., 54:3126, (1995).

Another category of immunotherapeutic antigens is the autoimmune antigen. In many autoimmune diseases, lymphocyte populations expressing surface receptors (antibodies or T cell receptors) reactive with antigens normally found in the body. Various antigens and peptides important in stimulating autoimmune diseases have been identified. These include for example myelin basic protein in multiple sclerosis, heat shock proteins and IgG $V_H$ regions in rheumatoid arthritis and lupus erythematosus. Another example of an autoimmune antigen is galactoseal-1-3-galactose-β1-N-acetylglucosamine, which has been implicated in xenograft rejection of pig organs by primates (see Collins et al., J. Immunol., 154:5500, (1995)).

With respect to autoimmune disease, certain antigens and peptides are known to activate the immune response resulting in organ or tissue destruction. It is now possible to identify Vβ clonality in T cell responses to these immunogens. Superantigens are capable of selectively inducing anergy in those T-cell clones especially when used in appropriate doses. Thus in some embodiments of the invention, autoimmune antigens may be used to activate certain T-cell clones and superantigens to inactivate, anergize or induce apoptosis in these autoreactive T-cell clones.

Another category of immunotherapeutic antigens is the pathogenic organism antigen. Various peptides have also been found to be significant in stimulating a protective immune response in infectious diseases. Immunotherapeutic antigens useful for the treatment of infectious diseases may be obtained from pathogenic bacteria, viruses, and eukaryotes. For example, hepatitis viral peptides, HIV envelope peptides, Plasmodium yoeli circumsporozoite peptide are capable of protecting the host against challenge with the infectious agent from which they are derived.

Anergy and Immunization

The invention provides methods and compositions for enhancing the in vitro stimulation by utilizing superantigens in conjunction with immunotherapeutic antigens. In vitro stimulation of T cells through the complex of T cell-antigen receptor and CD3 alone in the absence of other signals, induces T cell anergy or paralysis. T cell activation as measured by interleukin-2 production and proliferation in vitro requires both antigenic and co-stimulatory signals engendered by cell to cell interactions among antigen-specific T cells and antigen presenting cells. Various interactions of these CD2 proteins on the T-cell surface with CD58 (LFA-3) proteins and antigen-presenting cells, those of CD11a/CD18 (LFA-1) proteins with CD54 (ICAM-1) proteins and those of CD5 proteins with CD72 proteins can impart such a co-stimulatory signal in vitro. Cytokines derived from antigen-presenting cells (e.g. interleukin-1 and interleukin-6) can also provide co-stimulatory signals that result in T-cell activation in vitro. The delivery of both antigenic and co-stimulatory signals leads to stable transcription of the interleukin-2 gene and other pivotal T cell-activation genes. The foregoing co-stimulatory signals depend on protein kinase C and calcium. Potent antigen presenting cells express CD80 (B7 and BB1) and other related surface proteins and many T cells express B7 binding proteins namely CD28 and CTLA-4 proteins. Binding of CD80 by CD28 and CTLA-4 stimulates a T cell co-stimulatory pathway that is independent of protein kinase C and calcium and that also leads to stable transcription of the interleukin-2 gene and other activation genes leading to vigorous T cell proliferation. The stimulation of B cells also depends on the antigenic signal and co-stimulatory signal. The antigenic signal is generated by the interaction between the specific antigen and the cell-surface immunoglobulin. T cell derived cytokines (e.g., interleukins 1 and 4), physical contact between T cells and B cells through specific pairs of receptors and co-receptors, or both provide the signal or signals essential for B cell stimulation.

For in vitro immunization with superantigens, there is a requirement for class II molecules either on APCs or T cells or in purified form immobilized or solid supports. Some superantigens may activate T cells without requiring class II molecules and only various cytokines. Superantigens may be presented in immobilized form to T cells producing a proliferative response hence bypassing the need for APCs. T cells may be added to superantigens in vitro followed by APCs or superantigens may be added to APCs followed by T cells. Alternatively, the major components may be placed together simultaneously to produce immunization. Amplifying and co-stimulatory molecules including adhesion proteins (VCAM-1,ICAM-1) and B7 may be co-immobilized. In addition, various cytokines may be used to amplify the T cell response namely IL-1, IL-4 or IL-6. For anergy induction in vitro superantigens may be added to T cells in the absence of APCs or co-stimulatory molecules. In vivo anergy is induced by administration of superantigen parenterally or in the form of an adjuvant.

Functional Derivatives of Superantigen Protein and Immunotherapeutic Antigens

As previously discussed, the term "superantigen" refers not only to naturally occurring superantigens, but also to functional derivative thereof. Similarly, the term "Immunotherapeutic antigen" refers not only to naturally occurring immunotherapeutic antigens, but also to functional derivatives thereof. Peptide subfragments of whole enterotoxin molecules may be used to achieve the desired biological effect on lymphocytes while eliminating some of the toxic effects of the whole enterotoxin.

By "functional derivative" is meant a "fragment," "variant," "homologue," "analogue," or "chemical derivative" of peptide or of an enterotoxin, which terms are defined below. A functional derivative retains at least a portion of the function of the native protein monomer which permits its utility in accordance with the present invention.

A "fragment" refers to any shorter peptide. A "variant" of refers to a molecule substantially similar to either the entire protein or peptide fragment thereof. Variant peptides may be conveniently prepared by direct chemical synthesis of the variant peptide, using methods well-known in the art.

Biologically active enterotoxin fragments are known in the art and are preferred functional derivatives for use in accordance with the present invention. Studies of amino acid homology of Streptococcal pyrogenic exotoxin and enterotoxin B have suggested that there may be biologically active fragments present within the whole molecule. Indeed, cyanogen bromide generated toxin fragments of TSST-1 have been shown to be responsible for T lymphocyte mitogenicity and suppression of immunoglobulin synthesis. These functions could be selectively blocked by monoclonal antibodies directed to the respective fragments. Amino acid analysis of the toxins show that they contain similar domains that may give rise to mitogenic and emetic properties in susceptible cells. A peptide fragment of SEC was shown by Spero and Morlock to contain the active sites for emesis and diarrhea. The mitogenic region resided in the C terminal tryptic fragment of SEC. An immune functional site on Staphylococcal enterotoxin A has been identified corresponding to residues 1–27 of SEA which is responsible for stimulation of T cell proliferation and induction of interferon-γ. This SEA (1–27) sequence corresponds to N-Ser-Glu-Lys-Ser-Glu-Glu-Ile-Asn-Glu-Lys-Asp-Leu. Arg Lys-Lys-Ser-Glu-Leu-Gln-Gly-Thr-Ala-Leu-Gly-Asn-Leu-Lys- and blocks SEA induced T cell proliferation and production of interferon γ which was not seen with SEA (28–48) peptide. Thus, a functional site on SEA responsible for modulation of T cell function involves the N-terminal 27 amino acids. These molecules may interact at either the level of TCR or the binding of SEA to class II MHC antigens.

For TSST-1, mitogenic activity was shown to be located on a 14,000 dalton cyanogen bromide generated toxin fragment. Other studies using proteolytic digestion of the TSST-1 with papain demonstrated mitogenic activity in 12,000 dalton fragment occupying 2/3 of TSST-1 molecule toward COOH terminal end of holotoxin. On the other hand, non-specific mitogenicity of rabbit lymphocytes demonstrated by enterotoxins A, B, and $C_1$ was associated with the $NH_2$ terminal ends of the molecules.

Carboxymethylation of histidine residues of SEB caused a complete loss of emetic and skin sensitizing activity without changing the immunological specificity, e.g., T cell stimulating activity. An anti-idiotype monoclonal antibody against the combining site of an anti-SEB monoclonal antibody had no enterotoxic activity but can inhibit the enterotoxic activity, e.g., emetic response and diarrhea of a 10,000 molar excess of SEB. Anti-idiotype antibody also inhibited antibody and carboxymethylated enterotoxins may be useful tools to protect against the enterotoxin induced intestinal toxicity.

A homolog refers to a natural protein, encoded by a DNA molecule from a different species, which shares a minimum amount of structure and thereby function with the reference protein. Homologues, as used herein, typically share at least about 18% sequence similarity in the amino acid sequence.

An "analogue" refers to a non-natural molecule substantially similar to either the entire molecule or a fragment thereof.

A "chemical derivative" contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Biologically active regions of the enterotoxins and SPE-A, are substantially structurally homologous, thereby enabling a person skilled in the art to prepare synthetic peptides that exhibit similar biological effects in accordance with this invention (Johnson, L. P. et al., Mol. Gen. Genet. 203:354–356 (1986)).

A common method for evaluation sequence homology, and more importantly, for identifying statistically significant similarities, is by Monte Carlo analysis using an algorithm written by Lipman and Pearson to obtain a Z value. According to this analysis, Z>6 indicates probable significance, and Z>10 is considered to be statistically significant (Pearson, W. R. et al., Proc. Nat'l. Acad. Sci. USA 85:2444–2448 (1988); Lipman, D. J. et al., Science 227:1435–1441 (1985)). In the present invention, synthetic peptides corresponding to peptides on the one hand, or to enterotoxins are the other hand, are characterized in that they are substantially homologous in amino acid sequence to superantigen or an enterotoxin with statistically significant (Z>6) sequence homology and similarity to include alignment of cysteine residues and similar hydropathy profiles.

Variants

One group of variants are those in which at least one amino acid residue in the peptide molecule, and preferably, only one, has been removed and a different residue inserted in its place. For a detailed description of protein chemistry and structure, see Schulz, G. E. et al., Principles of Protein Structure, Springer-Verlag, New York, 1978, and Creighton, T. E., Proteins: Structure and Molecular Properties, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1–2 of Schulz et al. (supra) and FIGS. 3–9 of Creighton (supra). Based on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture.

Most deletions and insertions, and substitutions according to the present invention are those which do not produce radical changes in the characteristics of the protein or peptide molecule. However, when it is difficult to predict the exact effect of the substitution, deletion or insertion in advance of doing so, one skilled in the art will appreciate that the effect will be evaluated by routine screening assays, for example direct or competitive immunoassay or biological assay as described herein. Modifications of such proteins or peptide properties as redox or thermal stability, hydrophobicity, susceptibility to proteolytic degradation or the tendency to aggregate with carriers or into multimers are assayed by methods well known to the ordinarily skilled artisan.

In the present invention, functional derivatives of enterotoxins or other related toxins include synthetic polypeptides characterized by substantial structural homology to enterotoxin A, enterotoxin B and Streptococcal pyrogenic exotoxins with statistically significant sequence homology and similarity (e.g., Z>6 in the Lipman and Pearson algorithm in Monte Carlo analysis (see above)).

2. Chemical Derivatives

Covalent modifications of the monomeric or polymeric forms of superantigens or immunotherapeutic antigens may be employed in the subject compositions. Such modifications may be introduced into the molecule by reacting targeted amino acid residues of the protein or peptide with an organic derivatizing agent that is capable of reacting with selected side chains or terminal residues. This may be accomplished before or after polymerization.

Cysteinyl residues most commonly are reacted with a-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, a-bromo-b-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides as noted above. Aspartyl and glutamyl residues are converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl and threonyl residues, methylation of the a-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980).

Form and Production of Immunotherapeutic Antigen-Superantigen Polymers

The immunotherapeutic antigens and superantigens comprising the present invention may be in the form of an antigen-superantigen polymer, as a noncovalent combination of monomers, or as a mixture of monomers and polymers. The active composition of the invention can vary depending on the type of antigen and superantigen employed, the relative amount of each component in the mixture or conjugate, and the mode of conjugation used in forming the antigen-superantigen polymers. In one embodiment, the immunotherapeutic antigen molecules are directly conjugated with superantigen molecules through the use of a cross-linking agent able to form covalent linkages between the antigen and superantigen. When homobifunctional cross-linkers are used to effect this type of linkage, large molecular weight complexes may be created due to polymerization. In such cases, the size of the antigen-superantigen polymer may be several hundred thousand daltons in size, and in some instances, they may be even millions of daltons in size. Conjugations done using the water-soluble 1-ethyl-3-(3-dimethylaminopropyl) carbodiimide (EDC),which facilitates amide bond formation between carboxylates and amines on proteins, can result in similar polymeric conjugates having molecular masses of many millions of daltons, often while maintaining complete solubility (particularly if the original monomers had good solubility properties). Large molecular weight polymers also may be formed if a carrier is used to attach immunotherapeutic antigens to superantigen molecules. If a protein is used as a carrier, the molecular size of such complexes will be greater than the combined mass of the antigen plus superantigen monomers by the amount and mass of carrier present. When using a large molecular weight carrier such as a keyhole limpet hemocyanin (KLH) that has an average mass of about 5 million daltons, the combined mass of the antigen-superantigen-KLH polymer will be even larger. A polymeric carrier such as periodate-oxidized dextran, which has numerous aldehyde coupling sites on its polysaccharide chain, can be used to form very large complexes by coupling multiple antigen and superantigen molecules along its length.

In another aspect of this invention, the antigen-superantigen conjugate may be relatively small in molecular mass by controlled cross-linking using heterobifunctional reagents. For instance, when using a heterobifunctional cross-linker like SMCC., a superantigen may be modified with the NHS ester end of the reagent to form amide bond derivatives of the protein that terminate in maleimide groups. The number of maleimide groups incorporated into a superantigen may vary from about 1 per protein molecule to perhaps as many as 30–40 per protein molecule, depending on the molar ratio of SMCC-to-superantigen used in the initial modification reaction. Reacting a sulfhydryl-containing peptide antigen with such a maleimide-activated superantigen could yield conjugates containing anywhere from about 1 peptide molecule per superantigen up to 30–40 peptides per superantigen. In practice, the lower ratio would not be targeted because statistics would dictate a large percentage of superantigen with no peptides attached (reactions are never 100% efficient). Similarly, the upper end of this ratio would be avoided, as high levels of cross-linker modification may result in loss of superantigen activity or precipitation. Thus, the optimal ratio of peptide-to-superantigen for this conjugation scheme is somewhere between these extremes and highly dependent on the nature of solubility of the antigen and superantigen making up the conjugate.

Thus, another aspect of this invention is that polymer conjugates of antigen and superantigen can consist of widely different ratios of the two components depending on the mode of cross-linking employed. When using a carrier such as periodate-oxidized dextran to form the peptide-superantigen conjugate there is great facility to create low and high ratios of peptide-to-superantigen complexes. For instance, a peptide can be reacted with the activated dextran carrier with a superantigen added to the mixture at a very low molar ratio to form a conjugate with perhaps only one molecule of superantigen per 100 molecules of peptide. Even higher ratios of peptide-to-superantigen can be used to prepare such conjugates, thus allowing discrete adjustment of the enterotoxin component to avoid toxicity issues. Using a multivalent carrier such as dextran to form the final immunotherapeutic polymer therefore allows the better potential for optimization of the activity of the conjugate than direct linking of antigen and superantigen. Similar to this approach is conjugation through a liposome carrier, wherein the antigen and superantigen are coupled to phospholipid derivatives on the vesicle surface. The ratio of antigen-to-superantigen used during the coupling reaction dictates the relative activity of the conjugate in the intended application.

Therefore, the immunotherapeutic antigen-superantigen polymers described by this invention may have ratios of antigen-to-superantigen that vary from equivalence (1:1) to as high as $10^6$:1 or even $10^8$:1 or as low as $10^{-6}$:1 or even $10^{-8}$:1. Each antigen-superantigen polymer is optimized in the ratio of components as well as in the mode of conjugation to produce a immunotherapeutic agent of this invention having high activity in its intended application while maintaining low toxicity. Such optimization is critical due to the wide variety of antigens that can be employed-each antigen having its own unique physical properties and biological activities that must be considered when preparing the final immunotherapeutic agent.

Peptide-superantigen polymers may be formed using conventional crosslinking agents such as carbodiimides. Examples of carbodiimides are 1-cyclohexyl-3-(2-morpholinyl-(4-ethyl)carbodiimide (CMC), 1-ethyl-3-(3-dimethyaminopropyl)carbodiimide (EDC) and 1-ethyl-3-(4-azonia-4,4-dimethylpentyl)carbodiimide. Preferred crosslinking agents are selected from the group consisting of 1-cyclohexyl-3-(2-morpholinyl-(4-ethyl)carbodiimide,(1-ethyl-3-(3-dimethyaminopropyl carbodiimide (EDC) and 1-ethyl-3-(4-azonia-4,4-dimethylpentyl)carbodiimide.

Examples of other suitable crosslinking agents are cyanogen bromide, glutaraldehyde and succinic anhydride. In general any of a number of homobifinctional agents including a homobifunctional aldehyde, a homobifinctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative and a homobifunctional photoreactive compound may be used. Also included are heterobifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homobifunctional crosslinking agents include the bifunctional N-hydroxysuccinimide esters dithiobis(succinimidylpropionate), disuccinimidyl suberate, and disuccinimidyl tartrate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio)propionamido] butane, bismaleimidohexane, and bis-N-maleimido-1, 8-octane; the bifunctional aryl halides 1,5-difluoro-2,4-dinitrobenzene and 4.4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether, the bifunctional hydrazides adipic acid dihydrazide, carbohydrazide, and succinic acid dihydrazide; the bifunctional diazoniums o-toluidine, diazotized and bis-diazotized benzidine; the bifunctional alkylhalides N,N'-ethylene-bis(iodoacetamide), N,N'-hexamethylene-bis(iodoacetamide), N,N'-undecamethylene-bis(iodoacetamide), as well as benzylhalides and halomustards, such as α,α'-diiodo-p-xylene sulfonic acid and tri(2-chloroethyl)amine, respectively.

Examples of other common heterobifunctional crosslinking agents that may be used to effect the conjugation of superantigen molecules to immunotherapeutic antigens that are peptides include, but re not limited to, SMCC succinimidyl-4-(N-maleimidomethyl)cyclohexane-1-carboxylate), MBAs (m-maleimidobenzoyl-N-hydroxysuccinimide ester), SLAB (N-succinimidyl(4-iodoacteyl)aminobenzoate), SMPB (succinimidyl-4-(p-maleimidophenyl)butyrate), GMBS(N-(γ-maleimidobutryloxy)succinimide ester), MPBH (4-(4-N-maleimidopohenyl)butyric acid hydrazide), M2C2H (4-(N-maleimidomethyl)cyclohexane-1-carboxyl-hydrazide), SMPT (succin-imidyloxycarbonyl-α-methyl-α-(2-pyridyldithio)toluene), and SPDP (N-succinimidyl 3-(2-pyridyldithio)propionate).

Crosslinking may be accomplished by coupling a carbonyl group to an amine group or to a hydrazide group by reductive amination.

Immunotherapeutic antigen-superantigen polymers also may be prepared by non-covalent attachment of monomers through ionic, adsorptive, or biospecific interactions. Complexes of peptide-superantigen with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of peptide-superantigen may be done to surfaces such as microparticle latex beads or to other hydrophobic polymers, forming non-covalently associated peptide-superantigen complexes effectively mimicking crosslinked or chemically polymerized protein. Finally, peptide-superantigen may be non-covalently linked through the use of biospecific interactions between other molecules. For instance, utilization of the strong affinity of biotin for proteins such as avidin or streptavidin or their derivatives could be used to form immunotherapeutic antigen-superantigen species. These biotin-binding proteins contain four binding sites that can interact with biotin in solution or be covalently attached to another molecule (Wilchek, M. et al., Anal Biochem. 171:1–32 (1988). Superantigens or peptides can be modified to posses biotin groups using common biotinylation reagents such as the N-hydroxysuccinimidyl ester of D-biotin (NHS-biotin) which reacts with available amine groups on the protein. Biotinylated superantigens or peptides then can be incubated with avidin or streptavidin to create large complexes. The molecular mass of such polymers can be regulated through careful control of the molar ratio of biotinylated peptide to avidin or streptavidin. The incorporation of biotinylated superantigen molecules to this complex can be done as well.

The therapeutic composition of the present invention may be prepared by crosslinking a mixture of peptide (or functional derivative) and a superantigen (or a functional derivative) with a carrier. The carrier preferably consists of a protein, a lipid or another polymer which can be covalently bonded to peptide (or derivative) and the superantigen. Preferred protein carriers include serum albumin, keyhole limpet hemocyanin, tetanus toxoid, ovalbumin, thyroglobulin, diphtheria toxoid, myoglobin, immunoglobulin and purified protein derivative of tuberculin. A non-protein polymer carrier may be a polysaccharide, a poly (amino acid), a poly(vinyl alcohol), a polyvinylpyrrolidone, a poly(acrylic acid), a polyurethane and a polyphosphazene. The immunotherapeutic antigen-superantigen polymer may be covalently bonded to a liposome.

Pharmaceutical Compositions and Their Preparation

The invention provides a variety of pharmaceutical compositions useful for practicing the methods of the invention. The pharmaceutical compositions of the invention may comprise either a (I) novel immunotherapeutic antigen-superantigen polymers described herein or a (ii) composition comprising a superantigen and an immunotherapeutic antigen in a formulation suitable for use in the treatment methods of the invention. Thus the compositions may be in the form of a lyophilized particulate material, a sterile or aseptically produced solution, a tablet, an ampule, etc. Vehicles, such as water or other aqueous solutions preferably buffered to a physiologically acceptable pH (as in phosphate buffered saline) or other inert solid or liquid material such as normal saline or various buffers may be present. The particular vehicle is not critical, and those skilled in the art will readily be able to determine suitable vehicles for use in a given embodiment of the subject methods.

Enterotoxins are highly soluble in aqueous solutions, as are immunotherapeutic antigen-superantigen polymers. The immunotherapeutic antigen-superantigen polymer or composition may be maintained in liquid or lyophilized form.

In general terms, a pharmaceutical composition may be prepared by mixing, dissolving, binding or otherwise combining the immunotherapeutic antigen-superantigen polymer of the invention with one or more water-insoluble or water-soluble aqueous or non-aqueous vehicles. If necessary, another suitable additive or adjuvant is included. It is imperative that the vehicle, carrier or excipient, as well as the conditions for formulating the composition are such that do not adversely affect the biological or pharmaceutical activity of the immunotherapeutic antigen-superantigen polymer.

Administration and Methods of Use of Compositions

The immunotherapeutic antigen-superantigen polymers and other immunotherapeutic antigen-superantigen compositions may be administered in predispensed unit dosage forms, each one containing an effective amount of the conjugate that is preferably in the range of 10 mg–50 mg per unit dose. The exact dosage varies from case to case and depends on patient's weight and age, administration route, type of disease, toxicity and can readily be determined by the skilled artisan without undue experimentation. The response to treatment is monitored preferably after each dose using methods well-known in the art as well as those disclosed herein. The total duration of treatment and number of doses given depends on the response of the subject to the previous dose or doses.

Conventional routes of administration are used. A T-cell stimulating or anergy producing amount (or therapeutically effective amount as described above) of a immunotherapeutic antigen-superantigen polymer according to the invention is contacted with the target cells. By "T-cell anergy effective amount" is intended an amount which is effective in producing a statistically significant inhibition of a cellular activity mediated by a TCR. This may be assessed in vitro using T-cell activation tests. Typically T-cell anergy or activation is assayed by tritiated thymidine incorporation in response to specific antigen.

The immunotherapeutic antigen-superantigen polymers may also be used in vitro to test products, monitor therapy, and diagnose diseases associated with abnormal function of T-cell receptors or abnormal processing of antigens. Thus, for example, it is possible to test whether a subject has a disease or a condition amenable therapy by the immunotherapeutic antigen-superantigen polymers of the present invention. The subject's cells, e.g., peripheral blood lymphocytes or regional lymph nodes, are analyzed in vitro for TCR expression. If the immunotherapeutic antigen-superantigen polymer activates or inhibits TCR expression and T-cell proliferation, the subject is considered a candidate for a given therapy. In this way, it may be possible to select among various immunotherapeutic antigen-superantigen polymers for a size and composition range and a dose range most likely to be efficacious in vivo. For monitoring therapy with the compositions of the present invention, one would assay TCR expression over time after administering the immunotherapeutic antigen-superantigen polymers. Additionally, cells bearing TCR would be assayed for the presence of the immunotherapeutic antigen-superantigen polymer bound to the cell surface, for example, by conventional immunoassay. Decreases in the relevant TCR binding or post-binding effector function would prognosticate or corroborate therapeutic efficacy. Restoration of these functions over time would serve as a useful indicator of the need to prolong or reinstate therapy.

For the diseases or conditions described herein, administration of the composition is typically parenteral, for example, by subcutaneous (sv), intravenous (iv), intra-arterial or intramuscular (im) injection or infusion to a mammal, preferably a human. The immunotherapeutic antigen-superantigen polymer may be administered locally, regionally, systemically or a combination of the above to the subject to achieve a therapeutic response.

Methods for the Treatment of Diseases

The invention provides for a wide variety of different embodiments for treating diseases with a combination of superantigen and immunotherapeutic antigen. The term "treatment" as used herein does not refer exclusively to a cure of a given disease, but includes any alleviation of symptoms or decrease in the rate of progression of the disease.

In one embodiment of the invention, the superantigens and immunotherapeutic antigens are administered directly into a patient. The superantigens and immunotherapeutic antigens may be administered in numerous different combinations. The superantigens and immunotherapeutic antigens may be administered together in the form of a solution containing both the superantigens and immunotherapeutic antigens. Alternatively, the superantigens and immunotherapeutic antigens may be administered separately to a patient. In those embodiments of the subject methods in which the superantigens and immunotherapeutic antigens are administered separately, the immunotherapeutic antigen may be conjugated to a carrier. When the superantigens and immunotherapeutic antigens are administered separately, the time between administrations may be anywhere in the range of from a few minutes to up to about one week, varying in accordance with the specific disease and the specific combination of therapeutic agents employed. In a preferred embodiment of the invention, the superantigens and immunotherapeutic antigens are administered in the form of a immunotherapeutic antigen-superantigen polymer of the invention.

In another embodiment of the invention, the superantigens and immunotherapeutic antigens are administered ex vivo. Ex vivo therapy is particularly advantageous because it avoids many of the toxic effects that may be associated with certain superantigens and immunotherapeutic antigens. In ex vivo therapy, lymphocytes are removed from a patient (or compatible donor) and exposed to a superantigen and an immunotherapeutic antigen. The superantigens and immunotherapeutic antigens may be administered to the lymphocytes in numerous different combinations. The superantigens and immunotherapeutic antigens may be administered together in the form of a solution containing both the superantigens and immunotherapeutic antigens. Alternatively, the superantigens and immunotherapeutic antigens may be administered separately. In those embodiments of the subject methods in which the superantigens and immunotherapeutic antigens are administered separately, the immunotherapeutic antigen may be conjugated to a carrier. In a preferred embodiment of the invention, the superantigens and immunotherapeutic antigens are administered in the form of a immunotherapeutic antigen-superantigen polymer of the invention. After exposure to the immunotherapeutic antigen-superantigen polymers or other superantigen containing compositions of the invention, the exposed lymphocytes may introduced into the patient. Lymphocytes for use in ex vivo therapy may be either purified or not. The use of filtration on suitable absorbing columns or fluorescence activated cell sorting may be used to obtain blood cells enriched for particular lymphocyte populations having markers of interest.

Tumoricidal effects may be accomplished with biologically active superantigen peptides, intact enterotoxins or superantigens alone or attached to antigen presenting cells (class II MHC, HLA-DR) and incubated ex vivo with a random T cell population or a population which may have been pre-enriched for the appropriate Vβ receptor. The T cell population would have been previously exposed to TAA. The activated T cell population with or without bound enterotoxin may then be reinfused into the host. Similar tumoricidal effects may be achieved with enterotoxins or biologically active fragments infused into a host who has had an "organoid" (an enriched T lymphocyte organ) implanted on a biocompatible matrix and placed in a site in the host such as the abdominal cavity, adjacent to the liver or subcutaneously.

A therapeutic amount of the novel peptide-superantigen composition is effective to treat an autoimmune, infectious or a neoplastic disease, as described in detail below. The desired therapeutic amount may also be measured in an in vitro test when the peptide-superantigen immunotherapeutic antigen-superantigen polymer is added to fresh plasma. Other in vitro assays are described below.

A method of treating a patient having autoimmune, infectious or neoplastic disease is also provided. The method comprises parenteral administration of a composition according to this invention to subject patients in need of such treatment.

In one embodiment, the therapeutic composition is administered intravenously. The composition can be administered once, but is preferably administered six to twelve times at intervals which may range from daily administration to administration at intervals of about one week to four weeks. Repeating the full treatment regimen is also contemplated, as described hereinafter.

The present invention also relates to the discovery that tumor specific responses to tumor peptides and superantigens exceeds that of either agent alone leading to augmented tumoricidal responses. The fundamental discovery is that peptide sensitization may induce an activation of a T-cell clone with selected TCR Vβ expression. Selected superantigens are capable of massively activating certain T-cells with defined TCR expression. Indeed, certain superantigens are specific for selected TCR phenotypes which are defined by their Vβ expression as shown in table 1. Hence an aspect of this invention is the selection of a superantigen or superantigen mutant which is capable of massively expanding a recognizable Vβ subset previously activated by the peptide. Hence, the initial invention involves the method of sequential use of TAA peptides followed by superantigens to massively expand a clone of T-cells with defined Vβ expression and tumor specificity. This expanded clone of tumor specific T-cells will then be reinfused into a tumor bearing host to produce a tumoricidal response.

In another embodiment of the invention, the subject methods of treating cancer may further comprise the step of genetically modifying the cancer cells in vitro so as express one or more gene products that will improve the stimulation of the tumor cells by T cells. Such gene products include, but are not limited to superantigen genes, superantigen mutant genes, tumor specific antigen genes, class I histocompatibility antigen genes, class II histocompatibility antigens. A wide variety of vectors may be used to express the desired gene products. Preferably, such vectors are designed for the constitutive expression of the genes of interest. Preferably, the vectors used are viral vectors because of the high efficiency of such vectors. Suitable viral vectors include vaccinia vectors, adenovirus vectors, retrovirus vectors, and the like. A review of protocols for viral vectors can be found in, among other places, Kaplit, *Viral Vectors: Gene Therapy and Neuroscience Applications,* Academic Press, San Diego (1995).

The specified amount of immunotherapeutic antigen-superantigen polymer, preferably about 2–100 µg, is added to about 700 ml of human plasma that is diluted 1:1 with heparinized saline solution at room temperature. Human IgG in a concentration of 500 µg/dl (in the 700 ml total volume) may also be used. The solutions are allowed to stand for about 1 hour at room temperature. The solution container may then be attached directly to an iv infusion line and administered to the subject at a preferred rate of about 20 ml/min.

In one embodiment, immunotherapeutic antigen-superantigen polymer is directly infused into a subject. The appropriate amount, preferably about 2–100 µg, is added to about 250 ml of heparinized saline solution and infused iv into patients at a rate of about 20 ml/mim.

The present composition can be given one time but generally is administered six to twelve times. The treatments can be performed daily but are generally carried out every two to three days or as infrequently as once a week, depending on the toxic effects observed in the patient.

The present invention provides an in vitro sensitization system in which human T cells are sequentially exposed to a specific shared melanoma antigen or to TAA attached to HLA-A1 followed by a bacterial superantigen. This provides an enriched and expanded T-cell clonal population with enhanced potency compared to a clone activated by peptide antigen alone. Specific immunization induced by the recently identified melanoma specific antigens coupled with the massive lymphoproliferative expansion and Vβ selectivity induced by the superantigens provides a reasonable predictability of producing a potent clone of T cells with tumor specificity. Specifically, the present invention uses the capacity of superantigens to promote the differentiation of tumor specific effector cells from TIL, peripheral blood lymphocytes or tumor vaccine primed lymph node cells obtained from patients with cancer. These cells will be exposed to the TAA in vitro. Once the predominant Vβ phenotype in TIL after the TAA stimulation is identified, the appropriate superantigen will be selected to activate, enrich and expand the preimmunized T-cell clonotype. The expanded T-cell clone will then be infused into patients and antitumor effects assessed. This invention provides TAA and superantigen, used sequentially in vitro to produce T cell clones capable of producing antitumor effects in patients with advanced cancer.

An effective dose of an enterotoxin in the therapeutic methods of this invention is between about 0.001 ng and 5 ng per treatment or between about 0.01 and 100 pg/kg body weight per treatment. The purity of the enterotoxin may be assured by producing it using recombinant methods although enterotoxins isolated by biochemical means are also included. In its monomeric form, an enterotoxin preferably shows a single band corresponding to a molecular mass of 28 kDa on PAGE (under reducing conditions) and a sharp peak on HPLC. The enterotoxin component of the present composition should be substantially free of other substances with which it is natively associated, e.g., endotoxins, nucleases and proteases.

Conjugates comprising peptides and superantigens are extremely efficient in activating T-cells and produce a tumoricidal T-cell preparation using a one step in vitro culture method over 3–4 days compared to a 7 day in vitro incubation period using the sequential immunization protocol In another aspect of the present invention, the Vβ repertoire of the tumor infiltrating lymphocytes or peripheral blood after stimulation with TAA will be assessed at various time before and after treatment. If a predominant Vβ clonality is identified, it will be further enriched and expanded in vitro with appropriate superantigen and then reinfused into the same host. Therefore, this invention analyzes the Vβ repertoire of T cells in tumor sites before and after treatment with the TAA. If a restricted clonality is identified, this clone is expanded in vitro with appropriate superantigen and reinfused into the same host to achieve additional tumor killing effects.

EXAMPLES

The following studies evaluated the underlying basis for the therapeutic effects and the toxicities of superantigens in a metastatic tumor model. More specifically, it was noted that with tumor sensitized lymph node cells incubated with SEB ex vivo and reinfused into the host produced a potent tumoricidal response.

Example 1

Preclinical Antitumor Efficacy and Safety Studies of Superantigen Staphylococcal Enterotoxin B (SEB)

Recently, experiments in murine sarcoma and rabbit carcinoma have been completed in which were designed to test the anti-tumor effects of a bacterial superantigen namely staphylococcal enterotoxin B (SEB). Potent tumoricidal activity was demonstrated against established tumor in these models at both primary and metastatic sites (Terman, D.S., Cancer Research Institute, New York, N.Y.,( June 1993), Shu, S., et al., *J. Immunol.*, 152, 1277, (1994)). Further studies in baboons using SEB injected intravenously provided a quantitative basis for a starting dose of SEB in human cancer patients. After evaluation of the efficacy and safety data, the FDA approved a phase 1/2 studies in patients with advanced cancer using intravenously administered SEB and ex vivo SEB respectively. Those data in IDs #4059 and #6090 pertaining to anti-tumor efficacy and safety of SEB are summarized herein.

The preclinical ex vivo sensitization system is briefly described. Anti-tumor effects were observed in mice bearing the murine 205/207 fibrosarcoma with pulmonary metastases using tumor draining lymph node cells which were harvested and incubated in vitro with SEB for 2 days and IL-2 for 3 days. These expanded T cells were injected intravenously into mice bearing established MCA 205/207 pulmonary metastases. After administration of SEB primed T cells, a highly significant reduction of pulmonary metastases in treated mice was noted compared to controls given IL-2 alone.

This ex vivo sensitization method had significant advantages over intravenously administered SEB as follows: (a) minimal amounts of SEB were administered to the host (b) the major T cell population contributing to the anti-tumor effects was stimulated directly by the superantigen (c) the potential neutralizing effect of circulating naturally occurring SEB specific antibodies was eliminated (d) host toxicity was minimal. The salient data from these efficacy studies are given below. Moreover, the amount of SEB infused into the host after in vitro incubation is anticipated to be well below the 0.32 ng/kg dose which was used as a starting intravenous dose in our FDA approved phase 1/2 trial.

We now apply the principles of this in vitro sensitization approach to human cancer patients using T cell stimulants coupled with superantigens. We examine the Vβ phenotype of TIL obtained after treatment with the MART-1 antigen. If a specific Vβ phenotype is observed then an appropriate superantigen will be used to expand that clone after which it will be reinfused into the same patient.

Experimental Studies

Staphylococcal enterotoxins form a group of structurally and serologically distinct extracellular proteins of similar molecular weight. Characteristically, they have a disulfide loop near the middle of the molecule and are readily soluble in water and salt solutions. They are relatively resistant to proteolytic enzymes and heat (Bergdoll, M. S., Academic Press, London, (1983), Marrack, P., et al., Science, 248, 750, (1990)). Functionally, the enterotoxins are the most powerful T-lymphocyte mitogens known, eliciting strong polyclonal proliferation of a large proportion of murine and human $CD4^+$ and $CD8^+$ T cells at concentrations $10^3$ lower than such conventional T cell mitogens as phytohemagglutinin and concanavalin A. They are capable of stimulating DNA synthesis at concentrations of $10^{-13}$ to $10^{-16}$ M. They bind to the variable region of the Vβ segment of the T cell receptor heterodimer and their activity is restricted by the major histocompatibility complex (MHC) class II antigens. The frequency of murine and human T cells responding to the enterotoxins exceeds that of conventional peptide molecules by several orders of magnitude. A striking resemblance exists between T cell responses to the enterotoxins and those to the minor lymphocyte stimulating locus (Mls) located on chromosome 1 (Bergdoll, M. S., Academic Press, London. (1983), Marrack, P., et al., Science, 248, 750, 1990), Kotzin, B. L., et al., Advances in Immunology, 54, 99, (1993), Drake, C. G., et al., J. Clinical Immunology, 18, 12, (1992), Herman, A., et al., Annu. Rev. Immunol., 9, 745, (1993), Scherer, M. T., et al., Annu. Rev. Cell Biology, 9, 101–28, (1993)).

In vitro studies have demonstrated that enterotoxins are potent inducers of various lymphokines, in particular, IL-1, and IL-2, tumor necrosis factor and interferon. Most recently, they have also been shown to induce lymphocyte serine protease and thromboglobulin production. In vivo studies in rabbits and monkeys indicate that most of the enterotoxins are capable of inducing fever and hypotension. In man, several of the enterotoxins have been implicated in the toxic shock syndrome. Bergdoll, M. S., *The Enterotoxins in Staphylococci and Staphylococcal Infections,* Easmon, CSF & Adlam, C., ed, *Academic Press, London.* 1983, Marrack, P. & Kappler. J., *Science,* 248. 750, 1990, Kotzin, B. L., Leung, D. Y. M. et al., *Adv Immunol,* 54, 99, 1993, Drake, C. G. & Kotzin, B. L., *J. Clinical Immunol.* 18, 12, 1992, Herman, A. et al., *Annu. Rev. Immunol.,* 9, 745, 1993, Scherer, M. T. et al, *Annu. Rev. Cell Biology,* 9, 101–28, 1993.

Methods

Highly purified SEB was prepared from culture media by a combination of resin adsorption, ion exchange chromatography, and gel filtration. SEB appeared as a predominant single band at 28 kDa and an additional weaker band at 20 kDa. SEB displayed single precipitin line in immunodiffusion using monospecific antisera. High performance liquid chromatography carried out on a MAC Plus controlling a Rainin Rabbit with a Hewlett Packard 104A Diode Array Detector and a Vyodac protein and peptide C18 column demonstrated sharp peak for SEB without significant shoulder. Amino acid analysis, performed with a Beckman 1000 unit, showed profiles corresponding to those of known SEB standards. Vβ profiles of murine splenocytes following SEB activation revealed predominantly Vβ 3, 8.1, 8.2 and 8.3. Purified SEB was devoid of endotoxin [Etoxate assay (Sigma)], alpha hemolysin, nuclease and protease (Quanti-Cleave assay). The SEB preparations were found to be mitogenic in a tritiated thymidine assay using murine Balb/C spleen cells and demonstrated no growth on fluid thioglycollate medium and soybean-casein digest.

New Zealand white female rabbits (Elkhorn Rabbitry, Watsonville, Calif.) weighing 2.5–5.0 kg, ages 2–4 months were used for these studies. The rabbit VX-2 tumor, a carcinoma indigenous to New Zealand white rabbits, was obtained from the Frederick Cancer Research Facility of the National Cancer Institute. Tumor fragments for inoculation were obtained from VX-2 carcinomas growing in the rabbit thigh. Fragments were implanted intramuscularly into the right thigh of recipient animals under halothane anesthesia. Tumors usually appeared at the implantation site within two to four weeks.

Therapy was started only after tumors grew to a size exceeding 8 $cm^3$. Tumors reaching this size showed no spontaneous regressions. For the SEB treated rabbits, the mean volume of tumors at the onset of therapy was 41.8 $cm^3$ (range: 10–129 $cm^3$ ). For the untreated group, the mean tumor volume was 22.8 $cm^3$ (range: 8–53 $cm^3$). Each toxin was diluted in sterile 0.9% NaCl to concentration of 250 μg/ml, filtered through a 0.45 micron Millipore filter and administered intravenously via the central ear vein at a rate of 0.3 ml/min over 3 minutes after which the tubing and needle were washed with 3 ml of 0.9% NaCl over an additional 3 minutes. SEB was administered to seven rabbits bearing VX-2 carcinomas in a mean dose of 26 μg/kg (range: 20–30 μg/kg) on 1, 2 or 3 occasions over a period of 12 days. The administration of additional injections of SEB was based on the tumor response to each injection. If tumor showed signs of regression during the three days after an injection, no further SEB was given, however, additional injections were given if tumors showed no change or progression.

Rabbit Carcinoma (VX-2) Model

Five of seven animals receiving SEB showed complete tumor remissions and one additional animal demonstrated 96% regression; one animal showed tumor progression. Five of the six animals displayed no tumor recurrences while one animal had a recurrence of tumor at the primary site. Five animals with complete remissions had sustained tumor regressions for 6–12 weeks. All six untreated control animals demonstrated tumor progression over an 80 day observation period with associated weight loss, inanition, anorexia and early death.

In 6 of 7 rabbits treated with SEB, complete tumor regressions were evident by day 65 after starting treatment without weight loss or anorexia (FIG. 1). Remissions were sustained in 5 animals for 6 to 12 weeks while one had a tumor recurrence at the primary site. In contrast, tumors in six untreated control animals had increased in size by 5–20 fold before day 40. Weight losses of 1–2 kg and anorexia were noted in all control animals. Three control rabbits died before day 40 and 3 before day 80 (FIG. 1). Toxicity following SEB infusion was predominantly acute and self limited. It included temperature elevations of 1–4□ F. above baseline for 24–72 hours after treatment associated with anorexia and mild weight loss. Temperatures and nutritional patterns normalized thereafter and most rabbits gained weight over the ensuing weeks as tumors regressed. Ibuprofen, 1 mg/kg was given subcutaneously every 6 hours to animals receiving SEB which reduced febrile responses exceeding 105° F. and shortened the period of anorexia and inanition. Histologic studies of the tumor in SEB treated rabbits 48 hours after the first injection of SEB showed extensive tumoricidal effect associated with mixed mononuclear cell infiltration. In summary, highly purified staphylococcal enterotoxin B (SEB), a superantigen which activates a large proportion of T cells via the variable region of the Vβ heterodimer, injected intravenously in a dose of 26 μg/kg into rabbits bearing large established VX-2 carcinomas (mean size: 41 $cm^3$) induced complete remissions in 6 of 7 animals. Remissions were induced within 40–80 days and sustained for 6 to 12 weeks in 5 of these animals. Tumor killing effects of the treatment were confirmed histologically. Untreated control tumors showed progressive growth and death in 40–80 days. Toxicity included transient anorexia, fever and inanition which was attenuated by subcutaneous administration of Ibuprofen. The potent antitumor effect of SEB suggested that anti-tumor immunity may reside within tumor specific T cell subsets bearing Vβ phenotypes which were selectively expanded and activated by SEB. These results demonstrated antitumor activity of a known superantigen against large tumor burdens in animals with established carcinomas when given via intravenous injection. These findings suggested a novel role of bacterial superantigens in host natural antitumor defenses and offered a potentially new approach to treatment of established carcinoma.

These studies raised several possibilities regarding the mechanisms of the tumor killing effects induced by SEB. We surmised that the potent antitumor effects of SEB might reside in a population of T lymphocytes bearing specific Vβ phenotypes which may have been pre-immunized in vivo by prior exposure to tumor. Hence, the complete remissions given above might be due to activation of a tumor specific T cell subset expressing a selective Vβ phenotype. Augmented T cell cytotoxicity induced by superantigens and directed to superantigens bound to class II receptors on tumor cells and endothelium in situ would be an additional mechanism of tumor killing attributable to SEB.

The enterotoxins are also capable of stimulating the production of numerous cytokines, in particular interferon gamma and beta as well as interleukin 1 and 2 and tumor necrosis factor. The enterotoxins might selectively direct presensitized tumor specific T cells to differentiate into interferon producing Th-1 T cells possibly under the influence of IL-12. Interferon γ induced by the initial in vivo administration of SEB in the model given above may have upregulated class II receptor expression on antigen presenting cells creating additional sites for SEB binding in situ with subsequent injections. Hence, an enhancement of interferon n production by tumor specific T cells may have contributed to the potent tumoricidal effects noted with SEB. Indeed, significant augmentation SEB and interleukin 2 mediated tumor specific T cell proliferation mediated by SEB and IL-2 in vivo coupled with enhanced interferon production by this subpopulation may account for the antitumor response noted with SEB.

Hence, we attempted to confirm the antitumor effects observed in the rabbit carcinoma system with SEB by testing this agent in a second tumor model, namely the murine MCA 205/207 sarcoma with established pulmonary metastases. This is a particularly challenging therapeutic model since it is resistant to IL-2 therapy. Moreover, it permitted the elucidation of the T cell subsets involved in the antitumor effects. Additional objectives of this collaboration were: a) to determine the Vβ profile of lymphocytes in tumor draining lymph nodes activated by SEB, b) to determine the specificity of the tumor killing effects reduced by SEB, c) to identify the Vβ restricted clone(s) responsible for the tumoricidal effect, d) to determine the mechanism of tumor cell killing induced by the SEB activated T cells population.

Murine Fibrosarcoma (MCA 205/207) Model

Employing identical lots of purified SEB that were used to induce antitumor effects in rabbits, antitumor efficacy was tested in the weakly immunogenic murine 205/207 sarcoma model in mice with established pulmonary metastases. Results of this collaborative study were reported in Shu, S., et al., *J. Immunol.* 152:1277–1288 (1994).

The experimental system of in vitro sensitization requires removal of tumor draining lymph nodes from tumor bearing mice and incubation of these cells in vitro for 2 days with SEB and then with IL-2 for an additional 3 days. The cells were then harvested and various cell volumes were injected intravenously into C57BL/6 mice bearing MCA-205 tumors with extensive pulmonary metastases. Control mice were given no treatment, or IL-2 alone. Phenotype analysis of SEB stimulated cells revealed that virtually all were $CD3^+$ T cells (>95%) while 47% were $CD4^+$ and 47.8% were $CD8^+$. SEB stimulated proliferation of T cells who showed particular Vβ expression. SEB stimulated primarily Vβ3 and all three members of the Vβ8 family (8.1, 8.2 and 8.3) (Table 1).

The antitumor efficacy of toxin-stimulated cells was assessed in adoptive immunotherapy experiments. We first tested cells generated by stimulation with different concentrations of SEB. Table 2 shows that stimulated MCA 205 tumor draining lymph node cells were effective when $10^7$ cells were given to a tumor bearing mouse regardless of different concentrations of SEB used for stimulation. However, at a lower cell dose ($5\times10^6$), cells generated with 2 μg/ml of SEB were most effective.

The activation procedure also involved the culture of stimulated cells in a low concentration (4 U/ml) of IL-2 for 3 days. The antitumor reactivity of activated cells appeared to be inversely proportional to the concentration of IL-2 from which they were generated. Cells expanded in 4 U/ml of IL-2 appeared to be optimal. In the absence of IL-2, SEB stimulated LN cells had potent antitumor reactivity but this culture condition resulted in decreased numbers of viable cells (Table 3).

The specificity of the adoptive immunotherapy mediated by SEB stimulated cells was examined in criss-cross experiments. Cells from lymph nodes draining MCA 205 or MCA 207 tumors were activated and tested against pulmonary metastases established from the same two tumors. The results clearly demonstrate that cells derived from either the MCA 205 ort MCA 207 tumor mediated tumor specific effects corresponding to their sensitization during in vivo tumor growth. The immune effector cells were generated from tumor sensitized pre-effector cells as a result of SEB stimulation (Table 4).

TABLE 1

Vβ Use of Tumor-Draining LN T Cells Stimulated with Anti-CD3, SEA, and SEB

| | % of Total T Cells | | | |
|---|---|---|---|---|
| | Fresh MCA 205 | Tumor-Draining LN Cells Stimulated With | | |
| Vβ T Cells | Tumor-Draining LN | Anti-CD3 | SEA | SEB |
| Vβ2 | 5.9 | 13.3 | <1.0 | 0 |
| Vβ3 | 5.2 | 4.4 | 29.9 | 32.5 |
| Vβ5.1, 5.2 | 8.7 | 11.6 | <1.0 | 1.2 |
| Vβ6 | <1.0 | <1.0 | <1.0 | 0 |
| Vβ7 | 9.0 | 8.6 | <1.0 | <1.0 |
| Vβ8.1 | 5.2 | 7.2 | | 4.8 |
| Vβ8.2 | 10.8 | 11.3 | 1.5 | 15.0 |
| Vβ8.3 | 7.5 | 5.8 | | 19.8 |
| Vβ9 | 2.1 | 2.3 | 0 | 0 |
| Vβ11 | 5.8 | 7.1 | 34.3 | 2.9 |
| Vβ12 | ND | 3.2 | 7.4 | 0 |
| Vβ13 | 4.4 | 4.0 | 1.5 | <1.0 |
| Vβ14 | 9.0 | 6.2 | <1.0 | 0 |
| Vβ17 | <1.0 | <1.0 | 0 | ND |
| Others | 24.4 | 16.2 | 20.4 | 21.8 |

TABLE 2

Generation of Therapeutic Immune Effector Cells from MCA 205 Tumor-Draining LN by Activation with SEB

| | | Treatment | | |
|---|---|---|---|---|
| SEB (μg/ml) | Cell Expansion | No. Cells × ($10^{-6}$) | In Vivo IL-2 | Mean No. Metastases (SE) |
| | | 0 | − | 210 (36) |
| 10 | 3.8X | 0 | + | 250 |
| | | 10 | + | 24 (9) |
| 2 | 3.2X | 5 | + | 164 (27) |
| | | 10 | + | 3 (2) |
| 0.4 | 2.1X | 5 | + | 19 (10) |
| | | 10 | + | 2 (1) |
| | | 5 | + | 52 (6) |

TABLE 3

Effects of IL-2 Concentration on Generation of Effector Cells from MCA 205 Tumor-Draining LN After SEB Stimulation

| IL-2 (U/ml) | Cell Expansion Exp. 1 | Cell Expansion Exp. 2 | Treatment No. Cells (×10⁻⁶) | Treatment In Vivo IL-2 | Mean No. Metastases (SE) Exp. 1 | Mean No. Metastases (SE) Exp. 2 |
|---|---|---|---|---|---|---|
|   |   |   | 0 | − | 250 | 250 |
|   |   |   | 0 | + | 250 | 248 (2) |
| 100 | 9.6X | 7.4X | 12 | + | 250 | 187 (28) |
|   |   |   | 6 | + | 250 | 243 (4) |
| 10 | 7.5X | 5.6X | 12 | + | 177 (33) | 73 (35) |
|   |   |   | 6 | + | 234 (14) | 86 (29) |
| 4 |   | 3.6X | 12 | + |   | 2 (2) |
|   |   |   | 6 | + |   | 43 (7) |
| 2 | 2.2X | 2.1X | 12 | + | 52 (11) | 0 |
|   |   |   | 6 | + | 189 (35) | 15 (10) |
| 0 |   | 0.5X | 12 | + |   | 1 (1) |
|   |   |   | 6 | + |   | 11 (5) |

To investigate the possibility that Vβ3 T cells which were selectively stimulated by SEB activation constituted the majority of the antitumor effects in the SEB activated cell population, Vβ3 or Vβ8 T cells were depleted with immunomagnetic bead absorption and monoclonal antibody inhibition. Therapeutic efficacy was enhanced in Vβ3 T cells were depleted and was diminished if Vβ T cells were removed. These results suggested a potential significant regulatory interaction between Vβ3 and Vβ8 in the antitumor effects and a preferential use of TCR genes in the immune response to autologous tumors (Table 5).

TABLE 4

Specificity of Adoptive immunotherapy mediated by SEB-Activated Tumor-Draining Cells

| Draining LN | In vivo IL-2 | Mean number of Metastases (SE) MCA 205 | Mean number of Metastases (SE) MCA 207 |
|---|---|---|---|
|   | — | 250 | 250 |
|   | + | 250 | 200 (32) |
| MCA 205 | + | 4 (2) | 116 (43) |
| MCA 207 | + | 250 | 0 |

In vivo deletion of CD4⁺ and CD8⁺ using specific monoclonal antibodies administered immediately after adoptive transfer of effector resulted in abrogation of antitumor effects suggesting that both CD4⁺ and CD8⁺ cells participated in mediating tumor regression. (Table 6).

The capacity of SEB stimulated cells to mediate tumor specific cytotoxicity was carried out using standard 4 hour $^{51}$Cr release assay. We consistently failed to demonstrate cytotoxic reactivity against specific or other syngeneic tumor target cells. Thus, despite in vivo therapeutic efficacy and the presence of CD8⁺ immune cells, SEB activated cells lacked a direct cytotoxic effect in vitro. (See FIG. 2 of Shu, S. et al, supra, at page 1285.)

We next examined whether the SEB stimulated effector cells secreted interferon γ, TNF or IL-2 when they encountered specific tumor cells in vitro. In several assays, stimulation of SEB 15 activated cells with irradiated tumor cells led to the secretion of an average of 49.1 U/ml of IFN-γ. (See FIG. 3 of Shu, S. et al., supra, at page 1285.)

TABLE 5

Therapeutic Efficacy of SEB-activated Tumor-Draining LN Cells After Depletion of Either Vβ3 of Vβ8 T Cells

| Cell Transferred | Mean No. metastases (SE) Magnetic bead depletion Exp. 1 | Magnetic bead depletion Exp. 2 | mAb Inhibition Exp. 3 | mAb Inhibition Exp. 4 |
|---|---|---|---|---|
| — | 233 (15) | 235 (10) | 182 (13) | 250 |
| Whole population | 133 (35) | 79 (15) | 60 (14) | 55 (14) |
| Vβ3 depleted | 18 (7) | 43 (13) | 6 (1) | 1 (1) |
| Vβ8 depleted | 160 (72) | 137 (15) |   |   |

TABLE 6

Effect of In vivo T cell Subset Depletion on Adoptive
Immunotherapy of Pulmonary Metastases with EB-Activated
MCA 205 Tumor Draining LN Cells

| No. Cells (×10⁻⁶) | mAb for In Vivo Depletion | Mean No. Metastases (SE) In Vivo Administration | |
|---|---|---|---|
| | | HBSS | IL-2 |
| 20 | Rig | 11 (7) | 0 |
| 20 | Anti-CD4 | 250 | 63 (30) |
| 30 | Anti-CD8 | 250 | 250 |

Summary of Major Conclusions from Anti-Tumor Efficacy Studies (1) Enterotoxin B (SEB) demonstrated antitumor effects against established tumors in two animal species namely rabbits and mice bearing two distinct types of tumors namely, MCA 205 murine sarcoma and the VX-2 rabbit carcinoma.
(2) Enterotoxin B was capable of inducing tumoricidal activity at both primary and metastatic sites.
(3) Enterotoxin B induced anticancer effects by two modes of administration namely:
  (a) Direct intravenous injection into tumor bearing hosts.
  (b) Ex vivo incubation of tumor draining lymph node cells from tumor bearing animals with SEB and subsequent reinfusion of the expanded cell population into the host. Enterotoxin B stimulated lymph node cells were capable of killing tumor in vivo whereas interleukin 2 alone was ineffective in the same system. The tumoricidal effect was specific for the immunizing tumor.
(5) Side effects of enterotoxin B injected intravenously or of reinfused SEB stimulated lymphoid cells were minimal and manageable with Ibuprofen.
(6) Enterotoxin B in the murine tumor system appeared to selectively activate a subset of T cells with Vβ phenotype which appeared to mediate the antitumor effects.
(7) The antitumor effects of enterotoxin B were not due to direct cytotoxicity but rather to interferon γ production by the SEB stimulated cells in contact with specific tumor.
(8) Interferon γ appeared to be the major cytokine produced by SEB stimulated tumor draining lymph node cells in contact with specific antigen.

The antitumor effect produced by SEB stimulated cells was specific for the tumor of origin used for initial stimulation.

Summary of Toxicity Studies of SEB in Primates Brief Design of the Study

Initial studies were carried out in Cynomolgus monkeys given SEB intravenously on study days 1, 4 and 11. Each article was infused through a cephalic or saphenous catheter over a one hour period via a previously calibrated Harvard infusion pump. Treatments were given at the same time each morning. The first animal received 0.2 µg/kg of SEB, and subsequent animals were given doses of 1 µg/kg and 5 μg/kg respectively. Subsequent studies were carried out in adolescent baboons with doses of SEB starting at 0.002 μg/kg and extending to 0.128 μg/kg on days 1 and 11. Animals were monitored for toxic reactions to the test article. Observations included daily weights, assessment of activity, urine volume, stool texture, general physical activity. In addition, vital signs were monitored before and at various intervals after administration of the test article. Blood for CBC, liver and renal function, electrolytes and fibrinogen was analyzed for two control periods prior to infusion and daily in the days following the infusions.

Summary of Clinical Findings

The initial studies were carried out with three Cynomolgus monkeys. The first monkey was given SEB in a dose of 0.2 μg/kg intravenously, the second received 1 μg/kg and the third 5.0 μg/kg on days 1 and 4. Baseline control clinical parameters and serologic studies showed no significant abnormalities.

Following the initial infusion, each of the three animals in this group developed renal failure with serum creatinine levels rising on the day following infusion to 2.8, 4.4 and 5.9 mg/dl, respectively. Two animals given the highest dose of SEB showed hyponatremia, metabolic acidemia and death within two to three days following the infusion. An animal given a second infusion on day 3 died immediately thereafter, but was in severe renal failure at the time of infusion. Autopsy findings in this group included fibrinous pleuritis with evident pulmonary edema and multifocal hemorrhage in the lungs, gastrointestinal tract and spleen. One animal showed evidence of tubular necrosis in the kidneys.

Due to the toxicity observed in this initial study, several changes were made in the protocol for subsequent studies. First, the species was changed from Cynomolgus monkey to baboon. The reasoning was that the baboon was a larger animal and would be easier to monitor clinically for signs of toxicity. If toxicity was encountered, particularly with respect to kidney failure, intravenous fluids could readily be administered and dehydration averted. Blood pressure measurements which were difficult if not impossible to obtain in smaller Cynomolgus monkeys would be readily measurable in baboons. Finally, because of their size it was felt that baboons would more closely approximate the human clinical condition. Accordingly, seven adolescent baboons were studied beginning with a dose of enterotoxin B of 0.002 μg/kg given intravenously on days 1 and 11. In subsequent animals the dose of SEB was increased two-fold to a maximum of 0.128 μg/kg in the seventh baboon treated.

Evaluation of clinical and serologic data in the baseline period before enterotoxin B infusion revealed that these animals were in excellent physical condition. Pertinent clinical findings that appeared shortly after infusion included a slight elevation in blood pressure and pulse rate up to 120 minutes after infusion. Over the same time period there were minimal changes in respiratory rate and rectal temperature. In the ensuing days following infusion over the entire dose range employed, activity was generally well maintained. Two animals showed evidence of transient anorexia and inactivity. An additional three had loose stools and one had frank diarrhea. This was generally self limited lasting no more than two to three days with full recovery. A second infusion was carried out on day 11 and was generally associated with hemodynamic changes that were similar to the first infusion. There were no sustained effects noted with subsequent follow-up. However, the second infusion appeared to be slightly better tolerated than the first. Ibuprofen, given subcutaneously in a dose of 5 mg every 8 hours during the preinfusion period, appeared to abrogate some of the anorexia and malaise that the animals experienced. It was the impression of the supervising veterinarian, that the animals' general demeanor, activity and appetite improved following the administration of this drug.

Serologically, all animals showed a slight elevation of their SGOT and SGPT values following infusion which lasted approximately two to three days thereupon reverting to normal. There was no evidence of significant elevation of the serum creatinine level. Six of the seven baboons studied did extremely well and at the end of the 21 day observation period were found to be in excellent condition. Autopsy of these animals carried out at the end of the 2 day period failed to show any signs of significant organ toxicity associated with the treatment.

One animal, however, died on the second day following infusion of 0.032 µg/kg of SEB. Clinically, the animal became anorexic and lethargic on the day following the infusion. There were ecchymoses, bruises and bleeding from the gums and rectum. The animal was found with fixed and dilated pupils together with labored respiration on the second day after infusion. His chemistries revealed an elevated serum creatinine and BUN indicative of acute renal failure. In addition, the SGOT, SGPT and LDH and alkaline phosphatase levels were elevated and there was evidence of metabolic acidosis and hyperkalemia. Platelets were markedly decreased as was serum fibrinogen. Clinically, the animal died of acute renal failure associated with disseminated intravascular coagulation. At autopsy, hemorrhage was noted in the lungs, skin, adrenal and intestine with multifocal necrosis in the lymph nodes, adrenal, liver and kidney. Focal to diffuse and severe nephrosis was noted.

At the conclusion of the 21 day observation period, 6 of the 7 animals were in excellent physical condition with normal appetite, stool texture and urine output. Their activity was assessed as excellent and their vital signs were within normal limits. Autopsies showed no significant findings in these 6 baboons.

Example 2

The following examples outline the therapeutic method, preparation of compositions and outcomes using peptides, superantigens and peptide-superantigen conjugates.

I. Immunizing Constructs (a) Peptides (b) Superantigens and superantigen mutants (c) Peptide-superantigen conjugates and fusion proteins (d) Tumor cells transfected with superantigens The clinical protocol given herein describes the sequential use of tumor associated peptides and superantigens to stimulate T cells in vitro. Once a predominant Vβ profile is identified after peptide stimulation then a superantigen or superantigen mutant which is known to stimulate that particular Vβ clone will be used to further expand that T cell population (Table 7). The peptides may include any tumor associated antigen which is capable of immunizing T cells.

Moreover, the peptides may be selected from a group such as viral hepatitis surface antigens, heat shock proteins, myelin basic protein. T cell anergic or stimulatory responses will occur based, in part, on the strength of the peptide stimulus and costimulating signals as well as the nature and potency of the superantigenic signal. In multiple sclerosis and rheumatoid arthritis induction of anergy to myelin basic protein and heat shock proteins respectively, may be desirable whereas in hepatitis and cancer, activation of specific T cell clones may be preferable.

TABLE 7

Exogenous Bacterial Superantigens Vβ Specificity

| Toxin | Mouse | Human |
|---|---|---|
| SEA | 1, 3, 10, 11, 17 | ND |
| SEB | 7, 8.1–8.3 | 3, 12, 14, 15, 17, 20 |
| SEC1 | 3, 8.2, 8.3, 11 | 12 |
| SEC2 | 3, 8.2, 10, 17 | 12, 13.1, 13.2, 14, 15, 17, 20 |
| SEC3 | 7, 8.2 | 5, 12 |
| SED | 3, 7, 8.3, 11, 17 | 5, 12 |
| SEE | 11, 15, 17 | 5.1, 6.1–6.3, 8, 18 |
| TSST-1 | 15, 16 | 2 |
| ExFT | 10, 11, 15 | 2 |
| SPE-A | ND | 8, 12, 14 |
| SPE-B | ND | 2, 8 |
| SPE-C | ND | ND |
| MAM | 6, 8.1–8.3 | 17 |

An alternative approach to sequential presentation of peptide antigens and superantigen to T-cells would be to create chemical conjugates between the two molecules to allow for a single molecular presentation. Such a conjugate could be constructed using any of a number of chemical cross linking agents. Care would need to be taken to ensure that the cross linking did not interact with the T-cell or the MHC binding region of the superantigen and the antigenic site of the tumor antigenic peptide. The peptide itself might be polymerized before cross linking to the purified HLA-A1 molecule and the superantigen in order to increase the number of available antigenic sites.

Similarly, chemical conjugates of peptide antigens, B-7 molecules, HLA-A1, superantigen and MHC class II molecules (preferentially the beta chain) will be created and appropriate fusion proteins may be constructed since the genes for all of the structures are now available.

Fusion proteins may consist of peptides such as tumor antigen (MART-1 for example), hepatitis peptides, heat shock proteins or myelin basic proteins coupled to superantigens for example. The genes for these agents are available and they could be transfected into high producing bacteria using known methodology. Considerations applicable to the chemical conjugates would also be relevant to fusion proteins, namely avoidance of steric hindrance of the antigenic and superantigenic binding sites.

Fusion proteins consisting of the above peptides plus class I HLA-A1 plus superantigen plus class II HLA antigens will be prepared by methods to be described. The purified peptides, HLA-A1, HLA class II and superantigens are all available and may be used for appropriate chemical constructs or fusion proteins to be used for in vitro or in vivo sensitization. Peptides useful in autoimmune disease or chronic viral diseases may also be substituted for the MART-1 to induce activation of T cell clones, as in hepatitis and HIV, or anergy, as in rheumatoid arthritis or multiple sclerosis. Induction of anergy or activation is related in part to the dose of superantigen and presence or absence of coactivating signals.

The basic invention involves several steps and includes several stimulator constructs and several methods for the production of effector T cells. In step 1, the host is immunized with tumor antigens in the form of peptides or naked or plasmid DNA coding for tumor specific antigens. Peptide superantigen conjugates or superantigen tumor cell transfectants may also be used. In step 2, after the host is immunized, usually 6 days to 3 months after vaccination, T cells are obtained which are further stimulated in vitro by stimulator constructs consisting of tumor peptides plus superantigens given sequentially or as fusion proteins or chemical conjugates of tumor peptides and superantigens or as tumor cells transfected with superantigen or α-Gal genes.

The superantigen stimulated T cell population may be further expanded in IL-2. An antiapoptotic step is introduced to prevent the stimulated T cells from undergoing activation induced cell death before they can be used therapeutically. In further steps, the DNA from the expanded T cell population containing tumor specificity and showing Vβ overexpression is extracted and transfected into an embryonic stem cell line as a means of creating a new line of genetically engineered T cells with tumor specificity. Moreover, the tumor specific T cell line generated from superantigen stimulation may also be fused with a T cell thymoma to create a T cell hybridoma producing a large number of tumor specific T cells with Vβ bias. Finally the DNA from tumor cell-superantigen transfectants may be extracted and used in naked or plasmid form as a vaccine for immunization prior to implantation of tumor or for intratumoral parenteral injection into hosts with established tumors. Example 10 exemplifies more specific methods for producing these inventions.

In autoimmune disease, the autoimmune peptides and superantigens, superantigens alone and peptide-superantigen conjugates as provided herein are used to anergize, tolerize or induce apoptosis in autoreactive T cell clones by employing these agents in vitro and in vivo for T cell stimulation as given in examples 9 and 10. The basic invention involves several steps and includes several stimulator constructs and several methods for induction of anergy in autoimmune T cells. In step 1, autoimmune peptides and superantigens or peptide-superantigen conjugates or naked or plasmid DNA coding for autoimmune antigen and superantigens are used to immunize the host Peptide-superantigen conjugates or fusion proteins may also be employed. In step 2, after primary immunization (6 days to 3 months), the host is further stimulated with the same reagents. This results in a state of specific tolerance or anergy in vivo to the immunizing peptide.

A. Preparation of Key Peptides for Immunization or Conjugation to Superantigens Preparation of HLA-Class II HLA class II DR peptides were affinity purified from an EBV-transformed β cell line LG-2 as described. (Van Seventer, G. A. *J Exp. Med* 174, 901 (1991)).

Preparation of HLA-A1 Peptides

For the peptide-MHC binding assays the HLA-A1 molecules are purified using Steinlin cells (HLA-A1-homozygous) as a source of MHC molecules. Briefly, detergent extracts of Steinlin cells are first depleted of HLA-B and -C antigens by repeated passage over a column prepared with monoclonal antibody B1.23.2, which is specific for these molecules (Ferradini, L., et al., Cancer Research, 52, 4649, (1992)). HLA-A1 molecules are subsequently purified by affinity chromatography using an immunoadsorbent prepared with antibody W6/32, which recognizes all human MHC class I molecules associated to β2-microglobulin. The adsorbed HLA-A1 molecules are eluted from the column with base (50 mM diethylamine) containing 1% octyl β-D-glucoside. The eluted HLA-A1 molecules are neutralized and dialyzed against phosphate-buffered saline containing 1% octyl glucoside and concentrated by ultrafiltration. Purity of HLA-A1 molecules is determined to be >90% by SDS/PAGE.

3. Preparation of MART 1 Antigen and Synthetic Peptides

MART-1 peptides are identified on the basis of the HLA-A2.1 binding motif. MART-127-35 peptide is synthesized by Peptide Technologies, Inc. (Gaithersburg, Md.). The other MART-1-derived peptides (the 9-mers MART-122-30, MART-156-64, MART161-60, MART195-103, MART-109-107, and the 10-mers MART-120-35 and MART-127-36) are synthesized by a solid phase method by using a multiple peptide synthesizer and purified by HPLC. The relative binding of peptides to HLA-A2.1, on the basis of the inhibition of binding of a radiolabeled standard peptide to detergent-solubilized MHC molecules, will be performed using various doses of the test peptides (ranging from 100 mM to 1 nM) coincubated with the 5-nM radiolabeled Hbc18-27 (FLPSDYFPSV) (SEQ ID NO:1) peptide and HLA-A2.1 heavy chain and β2-microglobulin for 2 days at room temperature in the presence of a mixture of protease inhibitors. The percentage of MHC-bound radioactivity will be determined by gel filtration and the ID50 will be calculated for each peptide.

4. Preparation of Ganglioside Tumor Antigens

There is marked increase in expression of the disialoganglioside GD2 and GD3 in human melanoma and neuroblastoma. Antigens consist of the GQ1b ganglioside (containing 2 sialic acid resides) in neuroblastoma and the disialoganglioside GD2. GD2 is heavily expressed as neuroblastoma, melanoma, glioma and small cell cancer of the lung. Viral transfection may lead to upregulation of expression of the GD2 or 3 system in tumor cells. Neutralization of virus may lead to downregulation of expression of this antigen system.

Ganglioside Extraction. Packed neuroblastoma cells (1 ml) are washed extensively with PBS and homogenized in chloroform:methanol(2:1). The residue is re-extracted with chloroform:methanol (1:1) and passed through a sintered glass funnel, and the remaining residue is again extracted with this same solvent. The extracts are combined, dried under nitrogen and partitioned in diisopropyl ether:n-butyl alcohol (6:4) and 50 ml mM NaCl.

5. Preparation of Glycoprotein Tumor Antigens

Numerous tumor glycoprotein antigens have been identified. For these purposes representative glycoprotein antigens from human melanoma will be described and their isolation.

6. Preparation of Xenograft Antigens

The Galα1-3 Galβ1-4GlcNAc(galactoseα1-3galactoseβ1-4-N-acetylglucosame) epitope (αGal) constitutes the major structure on pig cells to which human antibodies bind and produce hyperacute xenograft rejection. These antigens may be isolated as follows: Endothelial cell monolayers are washed with 50 mM sodium borate, 150 mM NaCl, 1.0 mM $MgCl_2$, 1.0M $CaCl_2$, and 0.1M PMSF at pH 7.2 (33). The cells are then scraped from the flasks in borate buffer and centrifuged at 450× for 10 min. Cell membranes are then extracted by resuspending the pellets in 50 mM n-octyglucoside, 1.0 mM $MqCl_2$, 1.0 M $CaCl_2$, and protease inhibitors (1.0 mM pepstatin, 1.0 mM aprotinin, 10 mM leupeptide, 10 mM antipain, and 10 mM chymostatin) for 1 h at 4° C. The porcine aortic endothelial cell membrane extracts are then centrifuged at 30,000× g at 4° C. for 30 min. and stored at −80° C. until used.

7. Preparation of Heat Shock Proteins

Peptides are prepared by automated simultaneous multiple peptide synthesis. The simultaneous multiple peptide synthesis set-up was developed using a standard autosampler (Gilson 221) as described previously. Briefly, for the concurrent synthesis of peptides, standard Fmoc chemistry with Pfp-activated amino acids (Dhbt for serine and threonine) in a six-fold molar excess and Hobt as catalyst is employed. Peptides are obtained as C-terminal amides from 6 mg resin/peptide (0.33 mEq/g PAL resin, Millipore, Bedford, Mass.). Two panels of peptides are synthesized, based on the sequences of Mtb hsp65 and rat hsp60. Peptides are 15-mers with 10 amino acid overlap with each adjacent peptide (i.e., residues 1–15, 6–20, 11–25, etc). Thus, every possible 11-mer sequence of each protein is contained within a peptide. For peptide solid-phase synthesis, an A430 peptide synthesizer (Applied Biosystems, Weiterstadt, FRG) was used. Shortly, 9-fluorenylmethoxycarbonyl-protected amino acids are used and converted to hydroxybenzotriazol-activated esters before synthesis. The first residue is coupled to p-alkoxybenzylalcohol-substituted polystyrene (Bachem A G, Bubendord, Switzerland). In order to complete the coupling reaction double cycles are used. 9-Fluorenylmethoxycarbonyl groups are removed with 20% piperidine, side-chain protecting groups are cleaved by 4 h treatment in 50% trifluoroacetic acid in N,N'-dimethylformamide containing 10% thioanisol and 10% metacresol. After precipitation in t-butylethylether and repeated washing, the deprotected peptide is suspended in 1.5% ammonium bicarbonate, lyophilized, and purified by reversed phase HPLC (TKS ODS 120T, LKB, Grafelfing, FRG) by using a gradient of 0 to 70% acetonitrile in 0.1% trifluoroacetic acid.

8. Preparation of HIV Peptides and HIV (IV9) Peptide

Peptide Synthesis and Purification. Peptides are synthesized either manually by conventional solid-phase methods using tBoc chemistry or on an Applied Biosystems 430A synthesizer and are analyzed by HPLC and amino acid analysis.

Some peptides (including RY12 and IV9) are purified by C18 reverse-phase HPLC (Vydac 218TP104) in aqueous trifluoroacetic acid with a 1%/min (or shallower) CH3CN gradient. All peptide concentrations are measured by micro BCA (bicinchoninic acid) assay (Pierce). Iodination is performed by using $Na^{125}I$ and a 4-to 5-fold molar excess of $Na^{125}I$ over peptide to achieve stoichiometric incorporation by the IodoBead method (Pierce). For histidine residue iodination, a higher pH (8.2 vs. 7.0) is used to favor imidazole ring proton dissociation.

Iodinated peptide species are separated by HPLC for cytotoxicity assays.

Radioactivity of the HPLC eluate is monitored by using an on-line radioisotope detector (Beckman 170).

Peptides prepared by solid-phase synthesis are obtained from Neosystem (Strasbourg, France). Sequences are given in Table 8. They are derived from influenza A virus proteins (Matrix, nucleoprotein, or hemagglutinin), and HIV-1 proteins (Gag, Env, Nef, Vif, Rev, and Vpr) of the BRY isolate. Peptides Gag. 205–219 and Gag. 265–279 are derived from the HIV-1 SF2 isolate.

Different peptides spanning the NEF aa sequence of the Hiv-BRU isolate are synthesized by Neosystem (Strasbourg, France), and supplied by the Agence Nationale de Recherche sur le SIDA. These overlapping peptides contain 9–16 aa. Lyophilized peptides are diluted in RPMI 1640 (Flow Laboratories) before use.

TABLE 8

| PEPTIDE | | SEQUENCE | |
|---|---|---|---|
| Influenza A virus | | | |
| Matrix | | | |
| M57–68 | | KGILGFVFTLTV | (SEQ ID NO:2) |
| MY+57–68 | | YKGILGFVFTLTV | (SEQ ID NO:3) |
| Nucleoprotein | | | |
| N147–158R⁻ | | TYQRTRALVTG | (SEQ ID NO:4) |
| N335–349Y⁺ | | SAAFEDLRVLSFIRGY | (SEQ ID NO:5) |
| Hemagglutinin | | | |
| H.130–142 | | HNTNGVTAACSHE | (SEQ ID NO:6) |
| H.305–329 | | CPKYVKQNTLKLATGMRNVPEKQTR | (SEQ ID NO:7) |
| HIV 1 | | | |
| Gag | 51–65 | LETSEGCRQILGQLQ | (SEQ ID NO:8) |
| | 205–219 | ETINEEAAEWDRVHP | (SEQ ID NO:9) |
| | 219–233 | HAGPIAPGQMREPRG | (SEQ ID NO:10) |
| | 265–279 | KRWIILGLNKIVRMY | (SEQ ID NO:11) |
| | 378–391 | MQRGNFRNQRKIVK | (SEQ ID NO:12) |
| | 418–433 | KEGHQMKDCTERQANF | (SEQ ID NO:13) |
| Env | 105–117 | HEDIISLWDQSLK | (SEQ ID NO:14) |
| | 312–327 | IRIQRGPGRAFVTIGK | (SEQ ID NO:15) |
| | 428–445 | FINMWQEVGKAMYAPPIS | (SEQ ID NO:16) |
| | 474–489 | RPGGGDMRDNWRSELY | (SEQ ID NO:17) |
| | 510–521 | VVQREKRAVGIG | (SEQ ID NO:18) |
| | 584–604 | RILAVERYLKDQQLLGIWGCS | (SEQ ID NO:19) |
| | 827–843 | YVAEGTDRVIEVVQGACR | (SEQ ID NO:20) |
| | 846–860 | RHIPRRIRQGLERIL | (SEQ ID NO:21) |
| Nef | 66–80 | VGFPVTPQVPLRPMT | (SEQ ID NO:22) |
| | 79–94 | MTYKAAVDLSHFLKEK | (SEQ ID NO:23) |
| | 113–128 | WIYHTQGYFPDWQNYT | (SEQ ID NO:24) |
| | 132–147 | GVRYPLTFGWCYKLVP | (SEQ ID NO:25) |
| | 137–145 | LTFGWCYKL | (SEQ ID NO:26) |
| | 160–174 | ENTSLLHPVSLHGMD | (SEQ ID NO:27) |
| Vif. | 1–15 | MENRWQVMIVWWVDR | (SEQ ID NO:28) |
| | 25–40 | VKHHMYVSGKARGWFY | (SEQ ID NO:29) |
| | 46–60 | SPHPRISSEVHIPLG | (SEQ ID NO:30) |
| | 60–72 | GDARLVITTYWGL | (SEQ ID NO:31) |
| | 71–85 | GLHTGERDWHLGQGV | (SEQ ID NO:32) |
| Rev | 1–16 | MAGRSGDSDEDLLKAV | (SEQ ID NO:33) |
| | 18–30 | LIKFLYQSNPPPN | (SEQ ID NO:34) |
| | 37–50 | ARRNRRRWRERQR | (SEQ ID NO:35) |
| Vpra | 1–14 | MEQAPEDQGRQREP | (SEQ ID NO:36) |
| | 55–68 | AGVEAIIRILQQLL | (SEQ ID NO:37) |
| | 68–80 | LFIHFRIGCRHSR | (SEQ ID NO:38) |

9. Preparation of Myelin Basic Peptides

Guinea pig MBP is purified from brain tissue by the modified method of Deibler et al. Protein content and purity are checked by gel electrophoresis and amino acid analysis. Overlapping 20-mers of guinea pig MBP according to Martenson are synthesized in the and purified on HPLC. The amino acid sequence of peptide 21–40, is MDHARHGFLPRHRDTGILDS, and the peptide 71–90 is SLPQKSQRSQDENPVVHF.

Residues 78 and 79 are deleted in the guinea pig sequence.

10. Preparation of Hepatitis Peptides

Synthetic Peptides and HBV Ag

Any 9- or 10-residue peptide that contains a leucine in the second position and a valine at the carboxy terminus would be an "ideal HLA-A2.1-binding motif." A panel of synthetic peptides containing the ideal HLA-A2.1-binding motif (Table 9) is provided by Cytel Corporation (San Diego, Calif.) or purchased from Multiple Peptide Systems (San Diego, Calif.) or Chiron Mimotopes (Clayton, Australia). Lyophilized peptides are reconstituted at 20 mg/ml in DMSO (Malinckrodt, Paris, Ky.) and diluted to 1 mg/ml with RPMI 1640 medium (GIBCO<Grand Island, N.Y.). rHBcAg is obtained from bacterial extracts of *Escherichia coli* as previously described.

TABLE 9

HBV-Derived Ideal HLA-A2.1-Binding Motifs

| PEPTIDE | SEQUENCE | |
|---|---|---|
| 1. HbcAg18–27 | FLPSDFFPSV | (SEQ ID NO:39) |
| 2. HbsAg201–210 | SLNFLGGTTV | (SEQ ID NO:40) |
| 3. HbsAg251–259 | LLCLIFLLV | (SEQ ID NO:41) |
| 4. HBsAg260–269 | LLDYQGMLPV | (SEQ ID NO:42) |
| 5. HBsAg335–343 | WLSLLVPFV | (SEQ ID NO:43) |
| 6. HBsAg338–347 | LLVPFVQWFV | (SEQ ID NO:44) |
| 7. HBsAg348–357 | GLSPTVWLSV | (SEQ ID NO:45) |
| 8. HBsAg378–387 | LLPIFFCLWV | (SEQ ID NO:46) |

11. Preparation of Malaria Peptides

A MAP vaccine, MAP4 (QGPGAP)4 (SEQ ID NO:48) P2P30, is synthesized using a method described previously and used as the immunogen in these studies. This vaccine consists of a central lysine core and four branched chains, each containing the B cell epitope (QGPGAP)4 (SEQ ID NO:49) from the PyCSP major repeat, and two T helper epitopes, P2 and P30, from tetanus toxin. A linear peptide, C(QGPGAP)2, and a recombinant protein, PyCS.1, are used as antigens in the ELISA. PyCS.1, which includes amino acids 64 to 321 of the PyCSP fused to 81 amino acids from the nonstructural protein of influenza A, is purified from *Escherichia coli* expressing this antigen by immunoaffinity chromatography using Navy Yoelii sporozoite 1 (NYS1), a mAb directed against PyCSP coupled to cyanogen bromide-activated Sepharose 4B.

12. Preparation of Autoantibody-derived Peptides 12-or 15-mer overlapping peptides representing the entire VHD region sequence of rheumatoid factors antinuclear antibodies and anti-DNA Mabs are prepared. A total of 411 12-mer peptides are synthesized to recapitulate the sequence of 100–110 amino acids in the VHD of mAbs. Each peptide overlapped its neighbor by all but one residue. Large quantities of selected 11–15-mer peptides are synthesized, using Fmoc chemistry. The synthetic peptides are analyzed for purity by HPLC and by mass spectrometry. Each peptide chromatographs essentially as a sharp single peak. All purified peptides have the expected molecular mass.

Below are listed VHD derived peptides from anti-DNA antibodies used as immunogens and for tolerance induction (Table 10).

TABLE 10

| Peptide | Peptide | | Spontaneous Proliferation of unprimed BWF 1 T cells |
|---|---|---|---|
| 1. A6H 34–45 (p34) | MNWVKQSHGKSL | (SEQ ID NO:50) | + |
| 2. A6H 58–69 (p58) | FYNQKFKGKATL | (SEQ ID NO:51) | + |
| 3. A6H 84–95 (p84) | SEDSALYYCARD | (SEQ ID NO:52) | + |
| 4. A6H 11–22 (p11) | LVKPGASVKMSC | (SEQ ID NO:53) | – |
| 5. A6H 93–107 (p93) | ARDSPYYYGSSYGFA | (SEQ ID NO:54) | – |
| 6. HEL 106–116 (p106) | NAWVAWRNRCK | (SEQ ID NO:55) | – |

13. Preparation of Superantigen and Superantigen Mutants

SEB Construct. The SEB gene is overexpressed in *Escherichia coli* as follows. A linearized plasmid containing the genomic SEB gene is used as a template in a PCR utilizing oligonucleotide primers that flanked the portion of the gene encoding the mature SEB without the signal peptide. The 5' primer is 5'-TAG-GGAATTCCATGGAGAGTCAACCAGA-3'(SEQ ID NO:56), which contained an EcoRI site placing the SEB gene in-frame with the LacZ gene when cloned into pTZ18R (Pharmacia Fine Chemicals, Piscataway, N.J.). This oligo also has an NcoI site that added an ATG between the lacZ gene fragment and the beginning of the SEB gene so that the SEB gene could be moved easily to other plasmids carrying its own initiation ATG. The 3' primer, which contained a HindIII site after the termination codon of the SEB gene, is 5'-AGCTAAGCTTCACTTTTTCTTTGTCG-3'(SEQ ID NO:57). The PCR fragment is digested with EcoRI and HindIII and ligated into EcoRI/HindIII-digested pTZ18R. *E. coli* XL1-Blue (Stratagene, La Jolla, Calif.) is transformed with the plasmid, a single transformant picked, and the insert in its plasmid (pSEB2) sequenced to check that it had no mutations. Upon induction this construct leads to overproduction of mostly cytoplasmic SEB ( 10 μg/ml of broth). However, rather than producing a LacZ/SEB fusion protein, the bacteria produce a protein with the same apparent molecular weight as secreted SEB from *S. aureus*. Either the LacZ portion of the fusion protein is cleaved in vivo from the majority of the SEB or the ATG introduced between LacZ and SEB is a more efficient translation initiation site than that of LacZ. This construct is modified to introduce silent base changes which produce useful restriction sites in the 5'-end of the gene.

Generation of SEB Mutants. SEB mutants are prepared in two ways. First, to introduce random mutations along the entire length of the SEB gene, the SEB construct is prepared again, but the PCR is performed with the concentration of either dATP or dTTP reduced 10-fold in order to increase the error rate of Taq polymerase. This reduced the amount of product by 5–10 fold. The products of the two reactions are combined and cloned into pTZ18R as above and individual transformants screened for mutant SEB as described below (BR mutants). Of 400 toxin-producing transformants screened, 10 are identified as functional mutants by their reduced ability to stimulate T cells. Low concentrations of dCTP and dGTP were tried as well, but less reduction in product resulted and no mutants were detected in screening 200 transformants. A second PCR method is used to introduce random mutations in 60–75 base-defined regions of the SEB gene. The following oligonucleotides (A, B, and C), are synthesized with each position containing 1% each of the three incorrect bases:

(A) 5'-ATTCCCTAACTTAGTGTCCTTAATAGAATATAT
TAAAGTCAAAGTATAGAAATTGATCTATAGA-3'
(SEQ ID NO:58);
(B) 5'-AGCTAGATCTTTGTTTTTAAATTCGACTCGAA
CATTATCATAATTCCCGAGCTTA-3' (SEQ ID NO:59);
(C) 5'-CCGGATCCTAAACCAGATGAGCTCCACAAA
TCTTCCAATTCACAGGCCTGATGGAAAATATGAA
AGTTTGTAT-3' (SEQ ID NO:60).

These mutant oligonucleotides are used as primers in a PCR reaction with either a vector (A and B) or internal SEB (C) oligonucleotide as the other primer and SEB as a template. Therefore, each molecule of the synthesized SEB fragments is predicted to have two to three random base mutations in the region corresponding to the mutant primer. The mutant fragment is incorporated into the SEB gene, either by using it plus another fragment containing the 3' portion of the gene as mixed template in a PCR reaction to resynthesize a full-length SEB2 gene or by digestion with the appropriate restriction enzymes and ligation into pSEB2 from which the corresponding region had been removed.

DNA Sequencing. Plasmid inserts are sequenced directly by the dideoxynucleotide method using Sequenase (U.S. Biochemical Corp., Cleveland, Ohio) with a modification for double-stranded supercoiled plasmid templates. Several oligonucleotide primers are used matching sequences either in the vector or SEB insert.

Mutant superantigens with Class I Binding Site Inserted. Envisioned is a superantigen structure with class II binding sequences replaced by class I binding groups using point mutation in the superantigen gene. This will permit the binding of superantigens directly to class I bearing tumor cells cross-linking them predominantly to CD8+ T cell with appropriate Vβ receptors.

14. Preparation of Mutant p53 Products

Peptides derived from mutant p53 products resulting from missense point mutations in various codons have been identified and prepared. The gene for these sequences may be transfected into tumor cells or the peptide itself may be used in an immunogen for in vitro sensitization. Immunization in vivo may proceed by placing the peptide in appropriate adjuvant. Alternatively peptides may be attached to class I antigen presenting cells for use in vivo or as in vitro T cell immunogen constructs.

15. Preparation of Acetylcholine Receptor Antigens

Myasthenia gravis is due to an antibody-mediated autoimmune attack directed against acetylcholine receptors at neuromuscular junctions. The target antigen has been purified from a variety of sources including human muscle and its molecular structure is now known. The alpha subunit of the acetylcholine receptor contains several epitopes that appears to be the major immunogenic region in myasthenia gravis activating humoral and T cell responses. Each of the two α subunits has an acetylcholine binding site that is located extracellularly and centered around amino acids 192 and 193.

However, there may be other significant epitopes based on the fine specificity of antibodies present in patients with myasthenia gravis. The T lymphocyte response in these patients may be directed to additional epitopes on the acetylcholine receptor. Although the majority of T cell recognition sites are on the a subunit, T cells also recognize epitopes in the other subunits. Indeed, T cells from patients have been shown to respond to more than 30 different acetylcholine receptor derived peptides. Once the dominant peptide(s) region for each individual patient is recognized, it will be prepared by methods given below:

Peptide Synthesis and Characterization. Twenty-six peptides (P1–P26), 14–20 residues long and overlapping one another by 4–6 residues, are manually synthesized in parallel. They correspond to 83% of the human α-subunit sequence (364 residues out of 437) and to 91% of its hydrophilic parts. Since a main constituent loop of the MIR was localized to peptide P6, six peptides, HM1–HM6, corresponding to the different parts of the P6 sequence repeated two or three times, are also synthesized. Their sequences (given in standard one-letter amino acid symbolism) are as follows.

HM1: Y N L K W N Y N L K W N Y N L K W N (SEQ ID NO:61)
HM2: P D D Y G G P D D Y G G P D D Y G G (SEQ ID NO:62)
HM3: V K K I H I V K K I H I V K K I H I (SEQ ID NO:63)
HM4: K W N P D D K W N P D D K W N P D D Y (SEQ ID NO:64)
HM5: Y G G V K K Y G G V K K Y G G V K K (SEQ ID NO:65)
HM6: W N P D D Y G G V K W N P D D Y G G V K (SEQ ID NO:66)

Peptide purity is assessed by reverse-phase high-pressure liquid chromatography (HPLC) using a $C_{18}$ column (Ultrasphere ODS) and a gradient of acetonitrile in 0.1% trifluoroacetic acid. The composition of all peptides is checked by amino acid analysis using phenylthiohydantoin derivatives of the amino acids released by acid hydrolysis. For peptides P1–P6, sequence and purity are further verified by gas-phase sequencing.

Synthesis and Purification of the Peptides. Eighteen consecutive 16- or 17-residue peptides, overlapping one another by 5 residues and spanning the entire extracellular part (residues 1–210) of the α chain, are used to map the antigenic regions on this part of the chain. The peptides are prepared by solid-phase synthesis and are purified and characterized as described above.

16. Additional Molecules

Any tumor associated antigen or autoimmunioen may be used for a primary immunogen before superantigen or as a conjugate or fusion protein with superantigen. Examples would be the MAGE 1, tyrosinase and other MART-1 peptides, the SW 205 antigen in colon carcinoma, breast and lung tumor associated antigens. Likewise other viral peptides may be utilized in hepatitis or HIV infection and any peptide considered to be causative may be employed in autoimmune diseases such as rheumatoid arthritis and multiple sclerosis.

Example 3

Immunizing Constructs: Chemical Conjugates of Superantigens and Peptides

A. Methods for Preparing Superantigen-Peptide Conjugates

The conjugation of a superantigen protein, such as SEB, to peptides or other targeting molecules can be done by a number of cross-linking methods. The following sections describe some of the more commonly-used conjugation techniques for coupling such molecules together to form a covalent complex, but these protocols are by no means exhaustive. Other reaction schemes may be used to generate similar peptide-superantigen conjugates that are within the spirit and scope of the present invention. For a review of bioconjugate techniques see Hermanson, G. T., Academic Press, (1996).

1. Use of Dextran as a Carrier to Create Multivalent Complexes of Superantigens and Peptides Dextran is a naturally occurring polymer that is synthesized in yeasts and bacteria for energy storage. It is mainly a linear polysaccharide consisting of repeating units of D-glucose linked together in glycosidic bonds, wherein the carbon-1 of one monomer is attached to the hydroxyl group at the carbon-6 of the next residue. The hydroxylic content of the dextran sugar backbone makes the polymer very hydrophilic and easily modified for coupling to other molecules. Each sugar monomer contains at least 3 hydroxyls (4 on the terminal units) that may undergo derivatization reactions. This multivalent nature of dextran allows molecules to be attached at numerous sites along the polymer chain.

Soluble dextran of molecular weight 10,000–500,000 daltons has been used extensively as a modifying or cross-linking agent for proteins and other molecules. It has been used as a drug carrier to transport greater concentrations of antineoplastic pharmaceuticals to tumor sites in vivo (Bernstein, A., et al., J. Natl. Cancer Inst. 60, 379–384, (1978); Heindel, N. D., et al., Bioconjugate Chem.,1, 77–82, (1990)), as conjugated to biotin to make a sensitive anterograde tracer for neuroatomic studies (Brandt, H. M. et al., J. Neurosci. Meth., 45, 35–40, (1992)), as a hapten carrier to illicit an immune response against coupled molecules (Shih, L. B., et al., Cancer Res., 51, 4192–4198, (1991)); Dintzis, R. Z., et al., J. Immunol., 143, 1239–1244, (1989)), as an inducer of B cell proliferation by coupling anti-Ig antibodies (Brunswick, M., et al., J. Immunol. , 140, 3364–3372, (1988)), as a multifunctional linker to cross-link monoclonal antibody conjugates with chemotherapeutic agents (Heindel, N. D., et al, Bioconjugate Chem., 2, 427–430, (1991)), and as a stabilizer of enzymes and other proteins (Zlateva, T. P., et al., Acta Biochim. Biophys. Hung., 23, 225–230, (1988)); Nakamura, S., et al., Agric. Biol. Chem. ,54, 3057–3059, (1990)). Dextran modification of macromolecules can provide increased circulatory half-life in vivo, decreased immunogenicity, and a heat and protease protective effect when coupled at sufficient density (Mumtaz, S., et al., Indian J. Biochem. Biophys. , 28, 346–351, (1991)).

Figure 2:
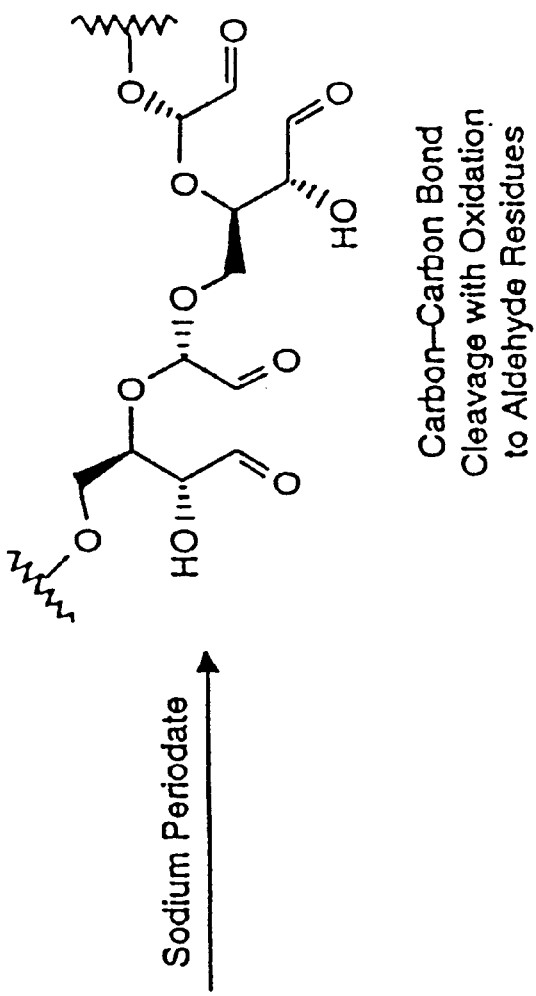
FIG. 2 shows an example of the periodate oxidation of a dextran polymer
Figure 2:
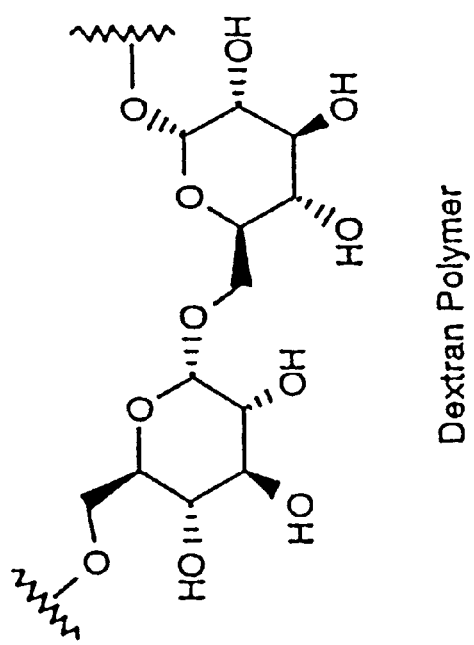
Figure 3:
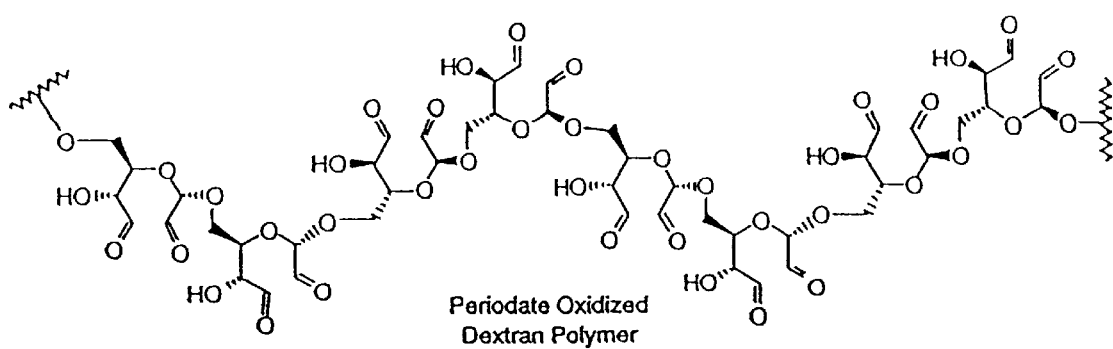
FIG. 3 shows an example of the conjugation of a superantigen and a Mart-1 peptide to an oxidized dextran polymer.
Figure 3:
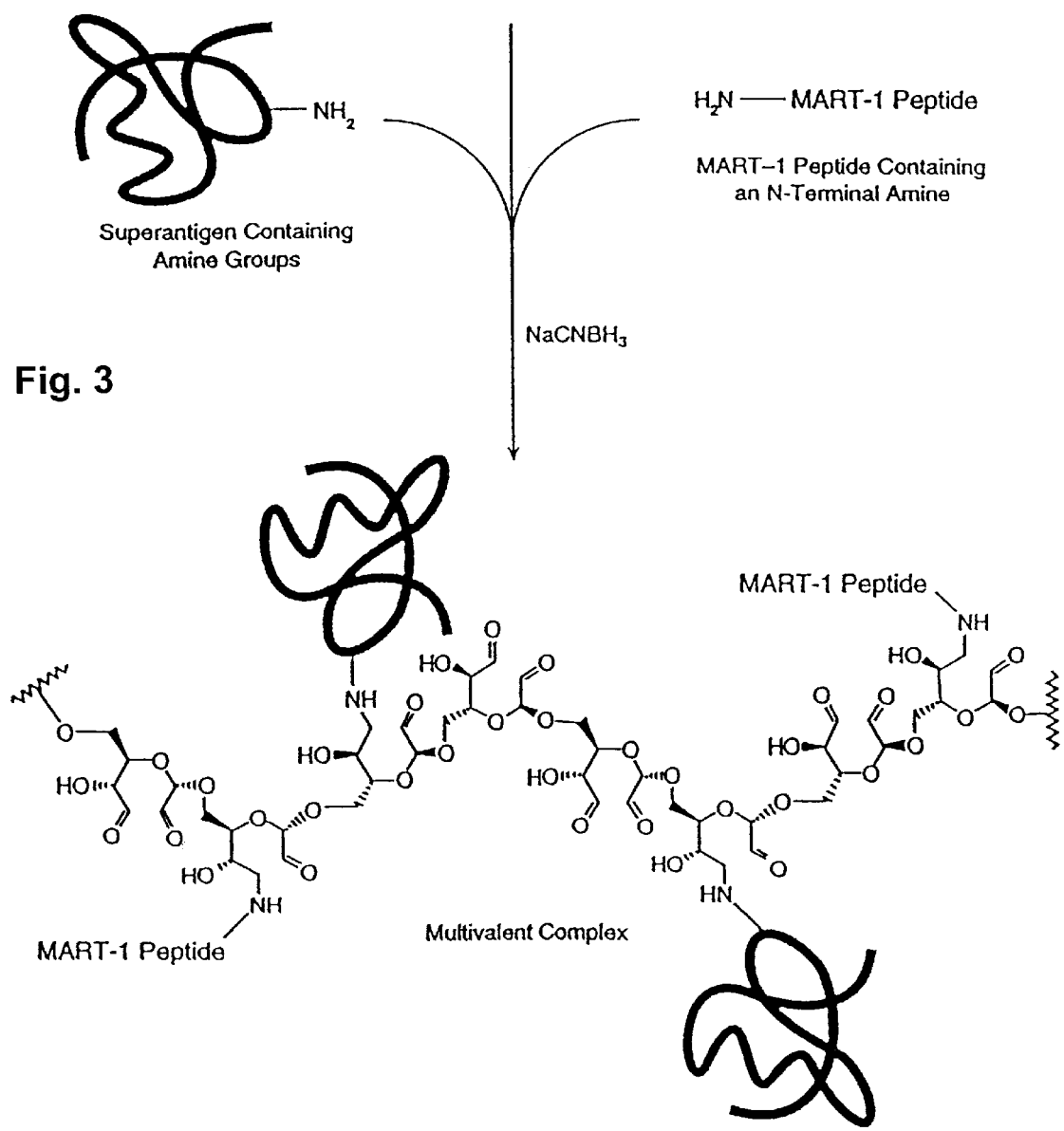
Figure 4:
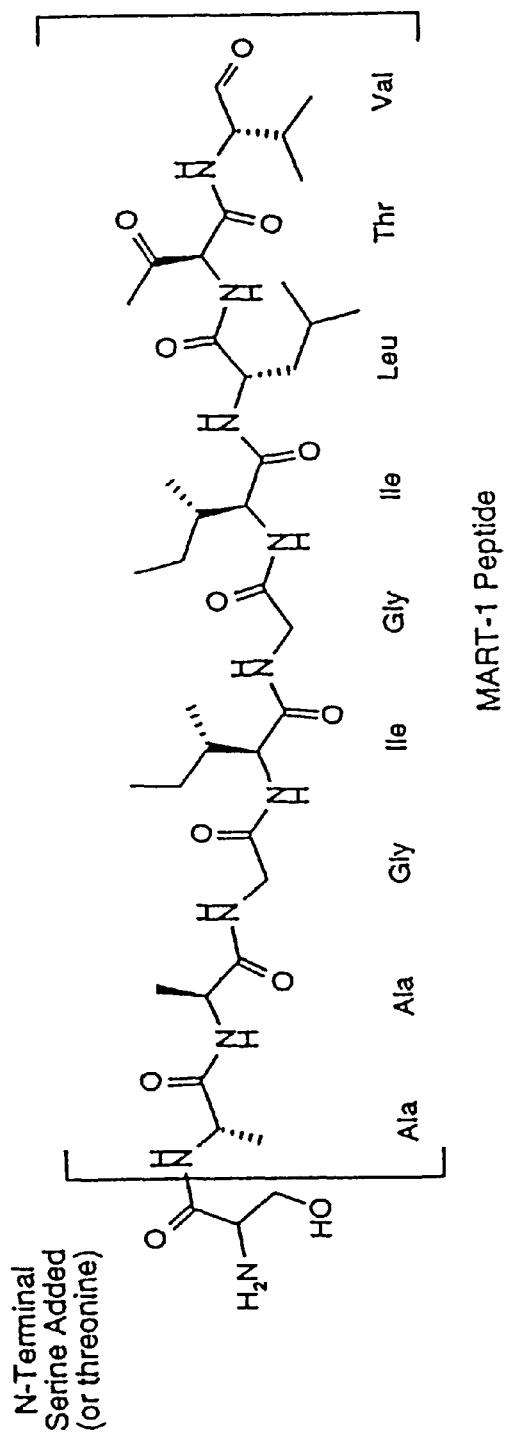
FIG. 4 shows an example of N-terminus labeling of a MART-1 peptide with a serine or threonine.
Figure 4:
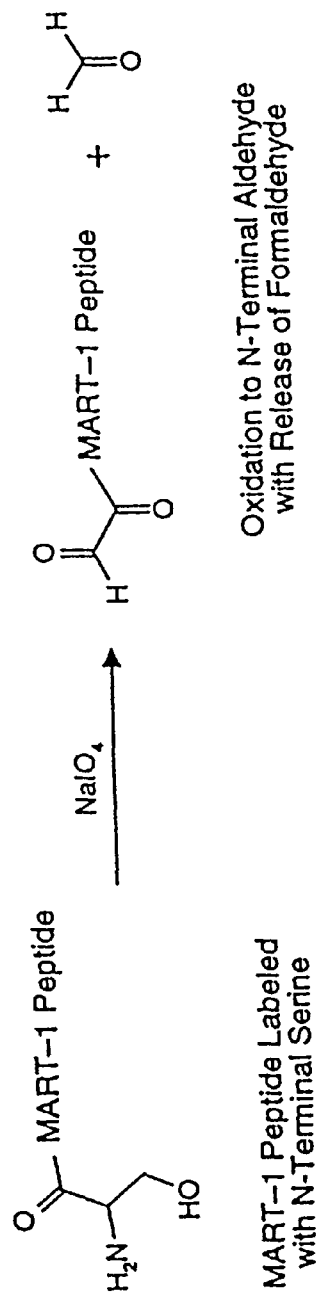
Figure 5:
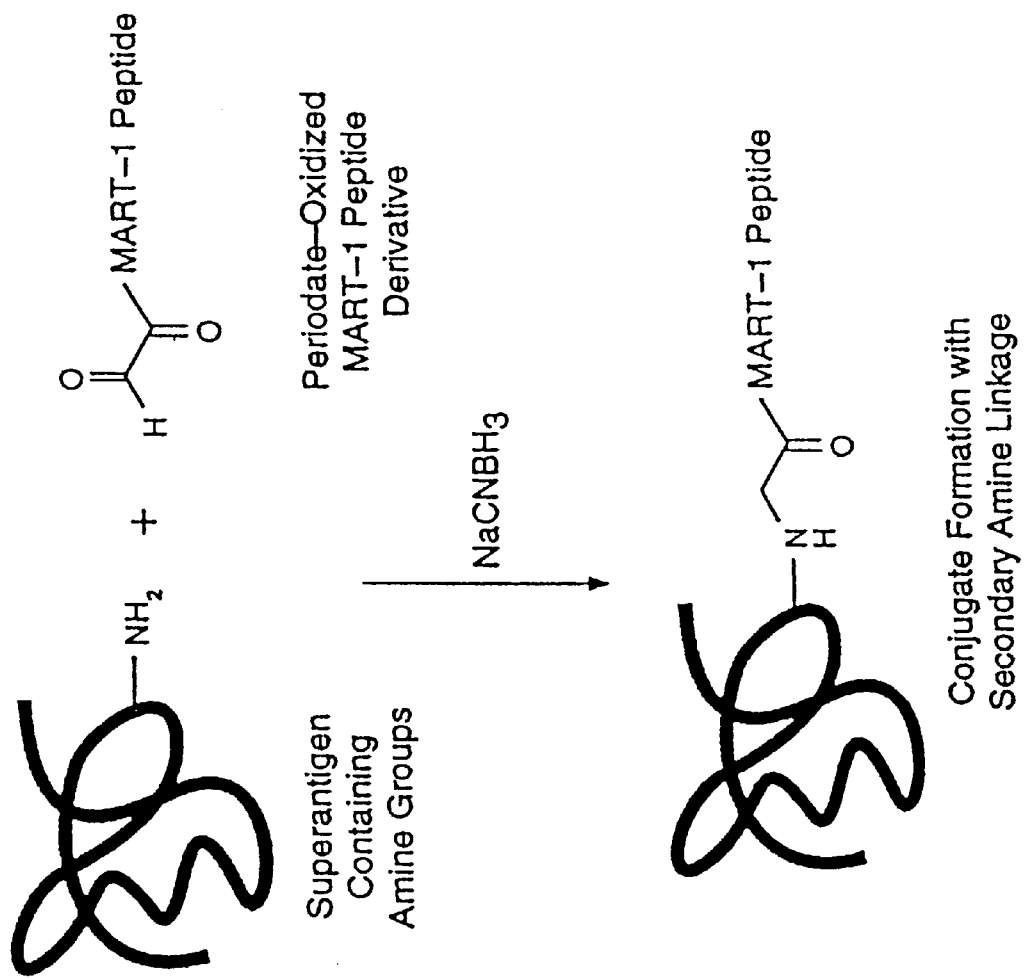
FIG. 5 shows an example of the conjugation of a superantigen to a periodate oxidized peptide.
Figure 6:
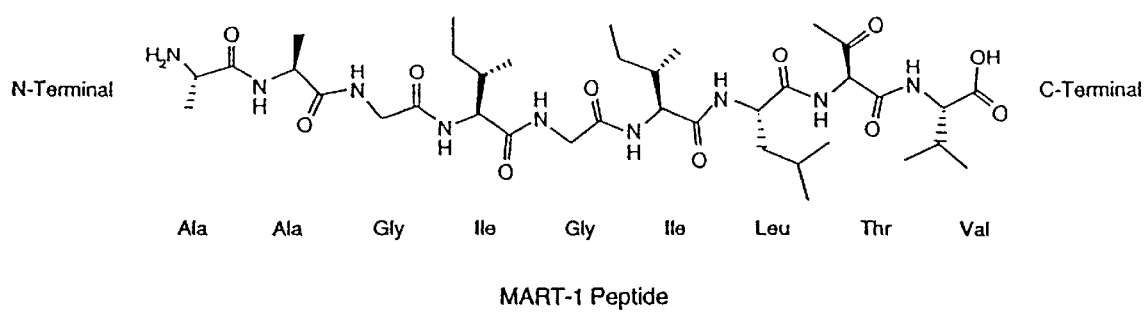
FIG. 6 shows the coupling of the superantigen protein SEB to peptide MART-1 through its amine or carboxylate terminus.
Figure 6:
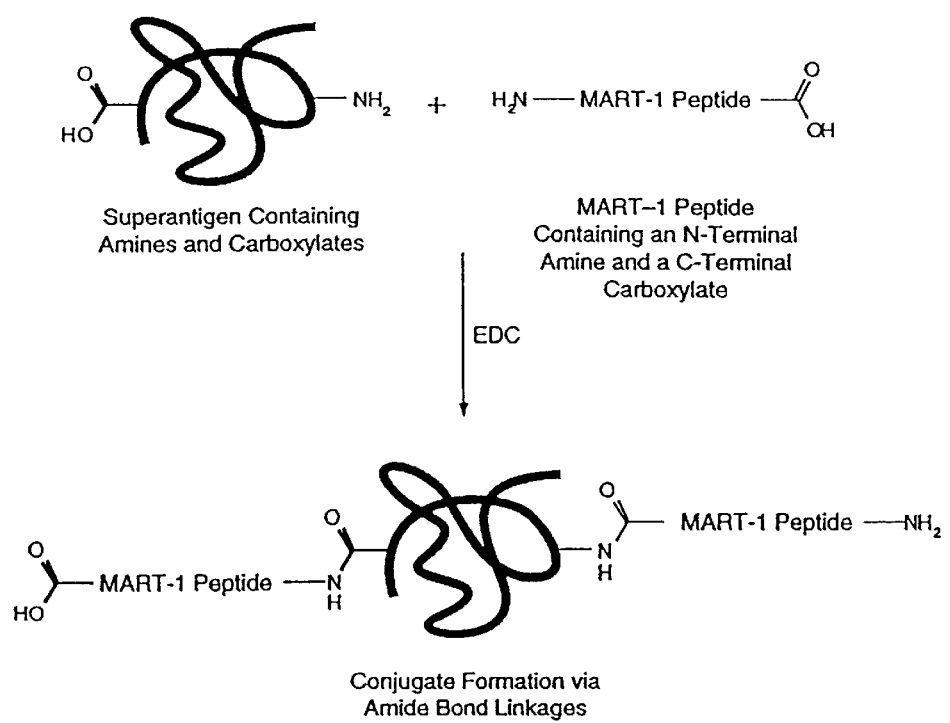
Figure 7:
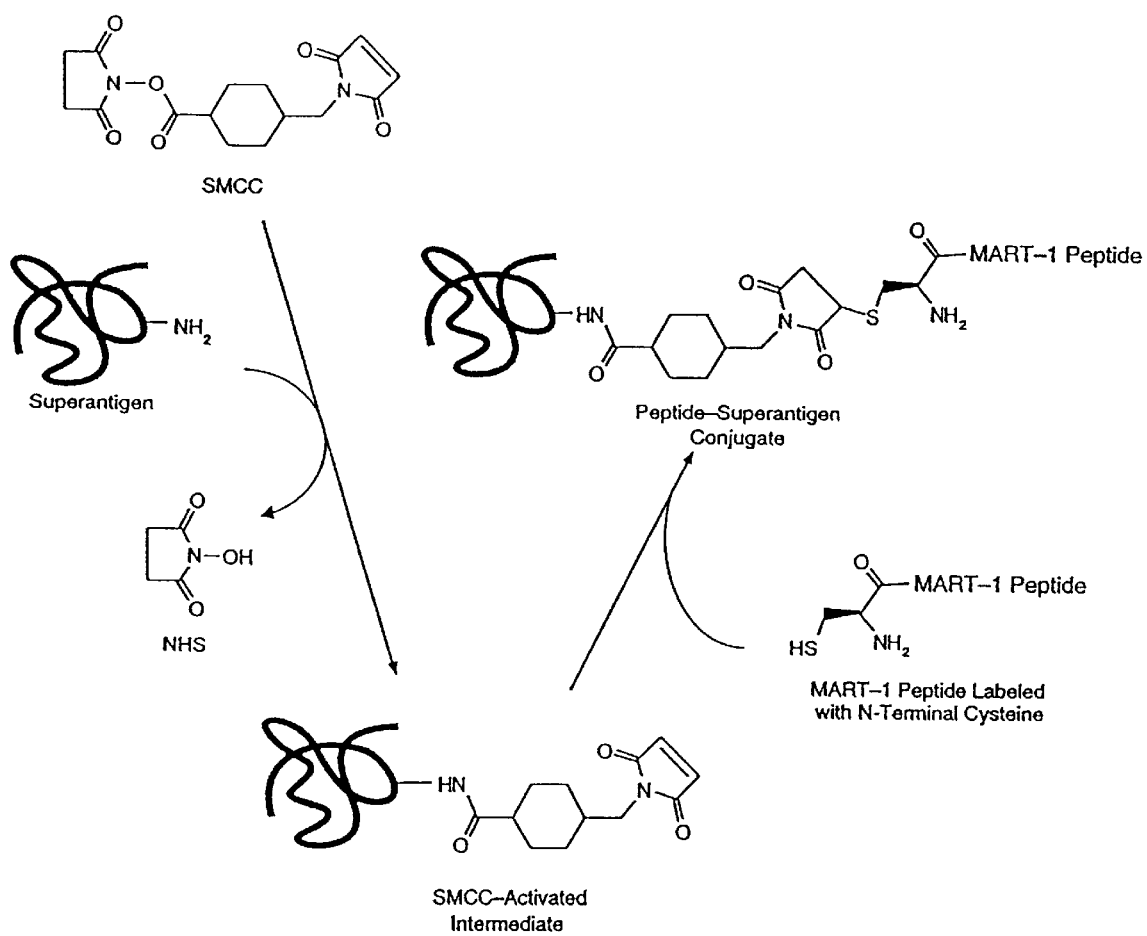
FIG. 7 shows some reactions associated with a sulfo-SMCC conjugation.
Figure 8:
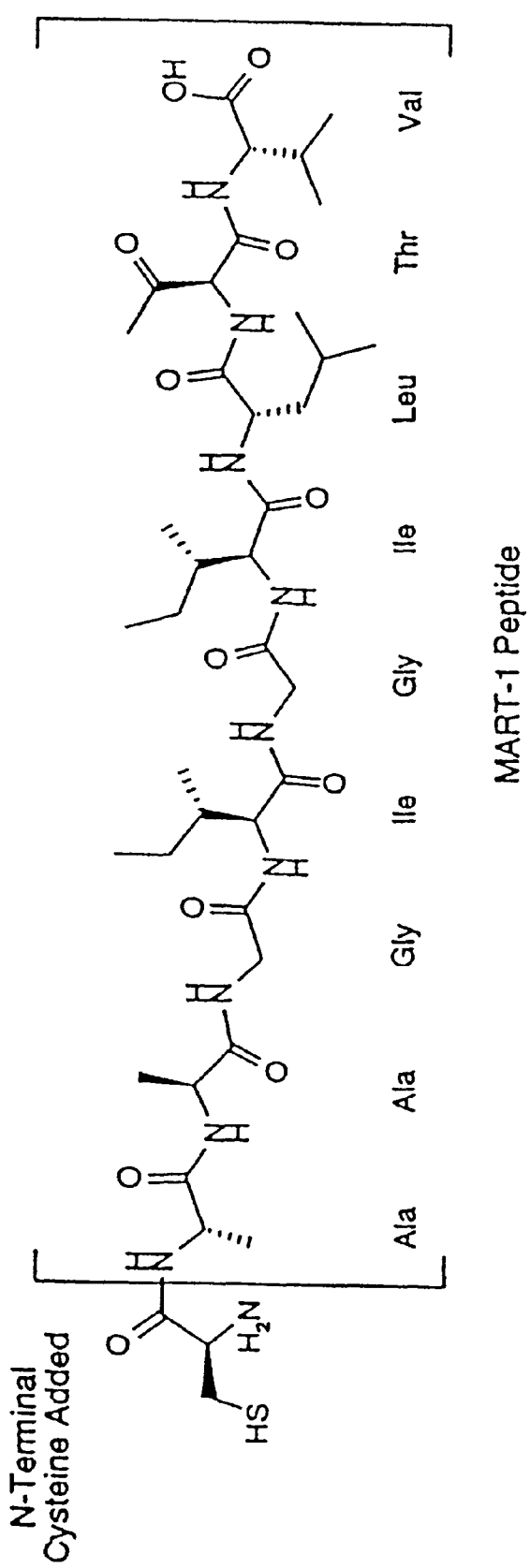
FIG. 8 shows the MART-1 peptide with a cysteine residue added to its N-terminal.
Figure 8:
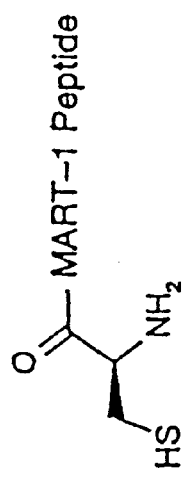

Since the dextran polymer contains adjacent hydroxyl groups on each glucose monomer, these diols may be oxidized with sodium periodate to cleave the associated carbon-carbon bonds and produce aldehydes. This procedure results in two aldehyde groups formed per glucose monomer, thus producing a highly-reactive, multi-functional polymer able to couple with numerous amine-containing molecules (Bernstein, A., et al., J. Natl. Cancer Inst., 60, 379–384, (1978)) (FIG. 2). Polyaldehyde dextran may be conjugated with amine groups by Schiff base formation followed by reductive amination to create stable secondary (or tertiary amine) linkages. Reductive amination (or alkylation) has been used for quite some time to conjugate an aldehyde- or ketone-containing molecule with an amine-containing molecule. The reduction reaction is best facilitated by the use of a reducing agent such as sodium cyanoborohydride, because the specificity of this reagent is toward the Schiff base structure and will not affect the original aldehyde groups. By contrast, sodium borohydride also is used in this reaction, but its strong reducing power rapidly converts any aldehydes not yet reacted into nonreactive hydroxyls, effectively eliminating them from further participation in the conjugation process.

Borohydride also may affect the activity of some sensitive proteins, whereas cyanoborohydride is gentler, effectively preserving the activity of even some labile monoclonal antibodies. Cyanoborohydride has been shown to be at least five times milder than borohydride in reductive amination processes with antibodies (Peng, L, et al., Appl. Biochem. Biotech., 14, 91–99, (1987)). Other reducing agents that have been explored for reductive amination processes include various amine boranes and ascorbic acid (Cabacungan, J. C., et al., Anal. Biochem., 124, 272–278, (1982)); Hornsey, V. S., et al., J. immunol. Meth., 93, 83–88, (1986)). Superantigen proteins may be modified with oxidized dextran polymers under mild conditions using sodium cyanoborohydride or sodium borohydride as the reducing agent. The reaction proceeds primarily through e-amino groups of lysine located at the surface of the protein molecules. The oxidized polymer also may react with N-terminal amines at the end of peptide molecules that do not contain lysine (such as the MART-1 peptide). The optimal pH for the reductive amination reaction is an alkaline environment between pH 7 and 10. The rate of reaction is greatest at pH 8–9 (Kobayashi, M., et al., J. Carbohydrate Chem., 10, 635–644, (1991)), reflecting the efficiency of Schiff base formation at this pH. Polyaldehyde dextran can be used to couple many small molecules, such as peptides, to superantigen molecules like SEB (FIG. 3). The multivalent nature of the oxidized dextran backbone provides more sites for conjugation than possible using direct coupling of the peptide to SEB with small cross-linking agents. The polar, hydrophilic nature of the dextran backbone also aids in maintaining solubility for conjugations with nonpolar, hydrophobic peptides such as MART-1. In addition, the flexibility of the dextran chain can provide better orientation of the SEB and peptide as they interact with cellular components of the immune system.

The following protocol for creating the polyaldehyde dextran derivative is based on the method of Berstein, A., et al., J. Natl. Cancer Inst., 60, 379–384, (1978)).

A. Protocol for Oxidizing Dextran with Sodium Periodate

1) Dissolve sodium periodate (NaIO4) (Sigma) in 500 ml of deionized water at a concentration of 0.03 M (6.42 gm).
2) Dissolve dextran (Polysciences) of molecular weight between 10,000 and 40,000 daltons in the sodium periodate solution with stirring.
3) React overnight at room temperature in the dark.
4) Remove excess reactant by dialysis against water. The purified polyaldehyde dextran may be lyophilized for long-term storage.

Protocol for Conjugating SEB to Peptides using Oxidized Dextran

The periodate-oxidized dextran prepared as described above can be used to create a covalent complex with SEB and peptides through a reductive amination process. The amount of each component in the final conjugate can be controlled through careful regulation of the molar ratios of SEB and peptide in the reaction medium.

1. Dissolve or buffer-exchange the periodate-oxidized dextran in 0.1 M sodium phosphate, 0.15 M NaCl, pH 7.2, at a concentration of 10–25 mg/ml. Other buffers having a pH range of 7–10 may be used with success, as long as they do not contain competing amines (such as Tris). A reaction environment of pH 8–9 (in 0.1 M sodium bicarbonate) will give the greatest yield of reductive amination coupling.
2. Add 1–10 mg of superantigen (e.g., SEB) and 0.1–1 mg of the peptide (e.g., MART-1) to each ml of the dextran solution. If SEB and MART-1 are being conjugated, adding 10 times more mass of the superantigen than peptide represents, on a molar ratio basis, 3.42 times more peptide than superantigen. Mix to dissolve. [Note: Due to the low solubility of MART-1 in aqueous environments, it should be first dissolved in DMF or DMSO at 10 mg/ml and then 10–100 ml of this stock solution added to each ml of the reaction solution.] A microprecipitate of MART-1 may form upon addition to the SEB solution, but the conjugation reaction will still proceed efficiently. Other ratios of SEB to peptide may be used successfully. For conjugating hydrophilic peptides, pre-dissolving them in an organic solvent is not necessary.
3. In a fume hood, add 0.2 ml of 1 M sodium cyanoborohydride (Aldrich) to each ml of the SEB/peptide/dextran solution. Mix well. Caution: cyanoborohydride is extremely toxic and should be handled only in wellventilated fume hoods. Dispose of cyanide-containing solutions according to approved guidelines. Alternatively, to avoid the toxicity problems of cyanoborohydride, an equivalent molar quantity of sodium borohydride may be added as reductant. If borohydride is used, a reaction pH of 9.0 in 0.1 M sodium bicarbonate buffer is appropriate.

4. React for at least 6 hours at room temperature. Overnight reactions also may be done.

5. To block excess aldehydes, add 0.2 ml of 1 M Tris, pH 8, to each ml of the reaction. If sodium borohydride was used as the reductant, this blocking step is unnecessary, because any remaining aldehydes would be reduced to hydroxyls. If a blocking agent is used, react for an additional 2 hours at room temperature.

7. Purify the conjugate from unconjugated SEB and peptide by gel filtration using a column of Sephacryl S-200 or S-300. Removal of excess SEB and peptide also may be removed from a dextran conjugate by dialysis using a membrane with a 30,000 molecular weight cut-off.

2. Conjugation of Peptides to Superantigens via Periodate Oxidation of N-Terminal Serine or Threonine Residues Sodium periodate also can be used to oxidize N-terminal serine or threonine residues of peptides, forming reactive aldehydes that can be used to couple to superantigen proteins using reductive amination (Geoghegan, K. F. et al., Bioconjugate Chem. 3, 138–146, (1992)). If a targeting peptide, such as MART-1, is modified during peptide synthesis to contain an N-terminal serine or threonine group (FIG. 4), then direct conjugation to superantigens can take place at ϵ-amine or α-amine groups of the protein (FIG. 5). The use of reductive amination to conjugate an aldehyde containing molecule to an amine containing molecule results in a zero-length cross-link where no additional spacer atoms are introduced between the molecules. Thus, peptides coupled to superantigen proteins using this method will all be coupled through secondary amine bonds at their N-terminals. If the peptide molecule also contains e-amine groups due to lysine amino acid residues, then there is potential for peptide-to-peptide coupling as well as peptide-to0-superantigen coupling. With MART-1 this is not a problem, since there are no lysine groups in the peptide. The degree of peptide coupling to the protein can be regulated through the molar ratio of peptide to superantigen in the conjugation reaction.

The following method for the oxidation of N-terminal serine or threonine containing peptides to form aldehydes is based on the method of Zalipsky, S., et al., Bioconjugate Chem. 6, 705–708, (1995)).

A. Protocol for Periodate Oxidation of Peptides Containing N-Terminal Serine or Threonine Residues 1. The peptide to be oxidized containing an N-terminal serine or threonine residue is dissolved in 0.05 M sodium phosphate, 0.15 M NaCl, pH 7.2, at a concentration of 1–5 mg/ml.
2. Sodium periodate is dissolved in water at a concentration of 0.2 M.
3. 100 ml of the periodate solution is added to each ml of the peptide solution and reacted for 5 min with mixing.
4. Excess periodate is consumed by the addition of 20 ml of 1 M Nα- acetylmethionine per ml of reaction volume.

B. Protocol for the Conjugation of Periodate-Oxidized Peptides to Superantigen Proteins a. Dissolve the superantigen protein to be conjugated at a concentration of 1–10 mg/ml in a buffer having a pH between 7.0 and 10.0. Higher pH reactions will result in greater yield of conjugate formation. Suitable buffers include 0.1 M sodium phosphate, 0.15 M NaCl, pH 7.2; 0.1 M sodium borate, pH 9.5; or 0.05 M sodium carbonate, 0.1 M sodium citrate, pH 9.5. Avoid amine containing buffers like Tris.
b. Add a quantity of the aldehyde-containing peptide (prepared as described above) to the superantigen solution to obtain the desired molar ratio for conjugation. A 10-fold molar excess of peptide to superantigen typically will result in 4–7 peptide molecules coupled per molecule of superantigen.
c. Add 10 ml of 5 M sodium cyanoborohydride in 1 N NaOH (Aldrich) per ml of the conjugation solution volume. Caution: Highly toxic compound. Use a fume hood and be careful to avoid skin contact with this reagent.
d. React for 2 hours at room temperature.
e. Purify the conjugate from excess peptide by dialysis or gel filtration.

3. Conjugation of Peptides to Superantigens by Carbodiimide Cross-linking

Peptides, such as the MART-1 antigen, may be conjugated with superantigen proteins using a carbodiimide to facilitate amide bond formation between carboxylates and amines on the two molecules. In this approach, the water soluble carbodiimide EDC is used for the conjugation reaction. EDC (1-ethyl-3-(3-dimethylaminopropyl) carbodiimide hydrochloride; MW 191.7; Pierce Chemical) first reacts with available carboxylic groups on either the superantigen or peptide to form highly-reactive O-acylisourea intermediates. The activated carboxylic group then can react with a primary amine to form an amide bond, with release of the EDC mediator as a soluble isourea derivative. The reaction is quite efficient with no more than 2 hours required for it to go to completion and form a conjugate. Since most peptide molecules contain either amines or carboxylic groups available for coupling, EDC-mediated conjugate formation may be the simplest method for the majority of superantigen-peptide conjugations. FIG. 6 shows the coupling of the superantigen protein SEB to peptide MART-1 through its amine or carboxylate terminus. It should be kept in mind that this type of conjugation may occur at either the C- or N-terminal of the peptide and protein or at any carboxyl- or amine-containing side chains. Therefore, this method can result in higher molecular weight complexes being formed due to peptide and/or superantigen polymerization. The degree of such oligomer formation can be controlled somewhat by the molar ratio of reactants used in the cross-linking reaction. In some cases, it may be advantageous to allow polymerization of the peptide component into a large complex prior to addition of the superantigen. In this approach, the peptide oligomer becomes macromolecular in size and thus potentially is more immunogenic in its interaction with the cells of the immune system. Subsequent addition of a superantigen to the EDC reaction forming such a peptide polymer provides the T-cell interacting component necessary for the synergistic effect envisioned in this patent. A similar large peptide complex with associated superantigen may be created by adding an excess of peptide over the amount of superantigen present before adding EDC to cause cross-linking. For instance, adding equal mass quantities of peptide and superantigen to the conjugation method described below would result in mainly peptide polymer formation with smaller quantities of cross-linked superantigen. In some instances, having a large peptide complex may provide optimal activity of the peptide-superantigen conjugate. Thus, the following protocol should be considered as flexible in the amounts of reactants added in order to form the best possible conjugate for each peptide and superantigen considered.

A. Protocol for Cross-linking Superantigen with Peptide Using EDC a. Dissolve the superantigen protein in 0. 1 M MES, 0.15 M NaCl, pH 4.7, at a concentration of 1–10 mg/ml. For neutral pH conjugations, substitute 0.1 M sodium phosphate, 0.15 M NaCl, pH 7.2, for the MES buffer.
b. Dissolve 0.1–1 mg of the peptide to be conjugated in each ml of the superantigen solution. If the peptide is sparingly-soluble in aqueous solution (such as MART- 1), it may be dissolved first in DMF or DMSO at a higher concentration (e.g., 10 mg/ml) and then an aliquot added to the superantigen solution.

c. Add the peptide/superantigen solution to a vial containing 2 mg of EDC (Pierce) and gently mix to dissolve.

d. Allow the reaction to continue at room temperature for 2 hours with periodic mixing or end-over-end rocking.

e. Purify the conjugate by gel filtration or dialysis.

4. Conjugation of Peptides to Superantigens using an NHS Ester-Maleimide Heterobifunctional Cross-linking Agent A common method for coupling peptides to proteins involves the use of a heterobifunctional cross-linker containing an NHS ester on one end and a maleimide group on the other end. This type of cross-linker allows excellent control over the coupling process by incorporating a 2- or 3-step reaction strategy directed against two different functional targets on both molecules. In this approach, the superantigen protein first is activated with the cross-linker through its amine groups, purified to remove excess reactants, and then cross-linked to a peptide molecule containing a sulfhydryl group. One of the most useful reagents for this conjugation approach is sulfo-SMCC.

The reactions associated with a sulfo-SMCC conjugation are shown in FIG. 7 [note: sulfo-SMCC is sulfosuccinimidyl-4-(N-maleimidomethyl) cyclohexane-1 -carboxylate; MW=436.37; Pierce Chemical]. This crosslinking reagent mediates the conjugation of a carrier protein through its primary amine groups to a peptide through sulfhydryl groups. The active N-hydroxysulfosuccinimide ester (sulfo-NHS) end of sulfo-SMCC first is reacted with available primary amine groups on the protein. This reaction results in the formation of an amide bond between the protein and the crosslinker with the release of sulfo-NHS as a by-product. The superantigen is then isolated by gel filtration to remove excess reagents. At this stage, the purified protein possesses modifications generated by the crosslinker resulting in a number of reactive maleimide groups projecting from its surface. The maleimide portion of sulfo-SMCC is a thiol-reactive group that can be used in a secondary step to conjugate with a free sulfhydryl (i.e., a cysteine residue) on a peptide, resulting in a stable thioether bond. A cysteine group can be incorporated at one end of a peptide during synthesis to allow this type of conjugation protocol to be used. FIG. 8 shows the MART-1 peptide with a cysteine residue added to its N-terminal. If a terminal cysteine residue is added to a peptide during its synthesis, its sulfhydryl group provides a highly specific conjugation site for reacting with an sulfo-SMCC activated superantigen. All peptide molecules coupled using this approach will display the same basic conformation after conjugation. In other words, they will have a known and predictable orientation, leaving the majority of the molecule free to interact with the targets of the immune system. This method therefore can preserve the major epitopes on the peptide while still modulating the immune response by being covalently linked to the superantigen.

The following protocol describes the activation of a superantigen with sulfo-SMCC and its subsequent conjugation with a peptide.

A. Protocol for Conjugating a Superantigen to a Cysteine-Containing Peptide Using Sulfo-SMCC a. Dissolve the superantigen of choice (e.g., SEB) at a concentration of 10 mg/ml in 0.1 M sodium phosphate, 0.15 M NaCl, pH 7.2.

b. Dissolve sulfo-SMCC (Pierce) at a concentration of 10 mg/ml in water. Immediately transfer 300 ml of this solution to each ml of the superantigen solution. Mix well. The appropriate amount of crosslinker to add is dependent on the amount of activation desired. The degree of sulfo-SMCC modification often determines whether the protein will maintain solubility after activation and coupling to a peptide. Particularly, when conjugations are done with nonpolar, hydrophobic peptides the degree of peptide substitution on the superantigen should be kept rather low to prevent precipitation.

c. React for 1 hour at room temperature.

d. Immediately purify the activated protein by gel filtration usOing a volume of Sephadex G-25 equal to 15 times the volume of the activation reaction. To perform the chromatography use 0.1 M sodium phosphate, 0.15 M NaCl, 0.1 M EDTA, pH 7.2 (conjugation buffer). The EDTA is present to prevent metal-catalyzed sulfhydryl oxidation to disulfides. Apply the reaction mixture to the column while collecting 0.5–1.0 ml fractions. Pool the fractions containing the activated superantigen (the first peak to elute from the column), and discard the fractions containing excess sulfo-SMCC (the second peak). Concentrate the activated superantigen to about 10 mg/ml using centrifuigal concentrators with a molecular weight cut-off of 10,000 (Amicon). The activated protein should be used immediately or freeze-dried to maintain maleimide stability.

e. Dissolve a sulfhydryl-containing peptide to be conjugated (e.g., MART-1 containing an N-terminal cysteine residue) at a concentration of 1 mg/ml in the conjugation buffer containing the activated superantigen. Dissolving the peptide in DMF or DMSO prior to adding an aliquot to the conjugation reaction may be done for sparingly soluble peptides.

f. Allow the conjugation reaction to proceed for 2 hours at room temperature.

g. Remove excess peptide from the peptide-superantigen complex by dialysis or gel filtration.

Conjugation of Human Tumor Antigens and Xenograft Antigens to Superantigen Molecules Conjugation of Ganglioside Tumor Antigens or Xenograft Antigens to Superantigen Molecules Tumor or xenograft antigen conjugation to superantigen molecules can be done by a number of methods well known to those skilled in the art. In cases wherein the antigen is a ganglioside, the immunogenic determinant is typically a polysaccharide in α-glycosidic linkage to a ceramide sphingolipid. One such antigen prevalent in human melanoma and neuroblastoma is GD2, containing a disialo group on the polysaccharide portion of the lipid. Another common glycolipid antigen involved in the hyperacute rejection process in xenotransplantation is the Gal alpha (1,3)Gal determinant making up the terminal region of the complex carbohydrate present on the cell surfaces of porcine tissues. Two methods of superantigen conjugation are presented for such antigens, one utilizing the isolated complex carbohydrate obtained from the purified ganglioside which is then chemically attached to superantigen, and another method wherein the ganglioside and superantigen are both incorporated into a liposomal membrane. Either method may be used to create complexes which are included in the scope of this invention, but they are by no means exhaustive of all the techniques which could be employed to conjugate human tumor antigens to superantigen molecules. Other conjugation strategies may be utilized to create an immunologically active complex as described by this invention.

Direct Conjugation of Ganglioside Polysaccharide to Superantigen Molecules

1. Ganglioside antigens are purified from cells as described previously. The gangliosides are then dissolved in aqueous solution at pH 6.0 at a concentration of 1.0 micromole/ml.

2. Endoglycoceramidase from Rhodococcus (Genzyme) is added to the ganglioside solution to a level of 5 milliunits. The solution is incubated overnight at 37□ C. with gentle agitation. The endoglycoceramidase specifically cleaves at the ceramide-polysaccharide bond, liberating ceramide and clipping off the complex carbohydrate making up the ganglioside.
3. The polysaccharide is isolated by HPLC size exclusion chromatography or by ultrafiltration.
4. Superantigen is dissolved in 0.1 M sodium phosphate, 0.15 M NaCl, pH 7.5, at a concentration of 1 mg/ml. The purified polysaccharide antigen is added to this solution at a concentration of at least 1 micromole/ml.
5. In a fume hood, 20 microliters of 5 M sodium cyanoborohydride solution in 1 M NaOH (Aldrich) is added to each ml of the superantigen solution.
6. The reaction is mixed gently and incubated at room temperature for 72 hours or 4□ C. for 1 week. This reaction reductively animates the reducing end of the polysaccharide (at the point it was cleaved by the endoglycoceramidase) to the amine groups on the superantigen protein, creating a stable conjugate coupled through a secondary amine linkage. The degree of polysaccharide coupling can be controlled by limiting the time of reaction.
7. Remove unreacted carbohydrate and cyanoborohydride by gel filtration on Sephadex G-25 or by dialysis.

Use of Liposomes to Create Ganglioside-Superantigen Complexes

1. Prepare a 5 mg/ml liposome suspension in 20 mM sodium phosphate, 0.15 M NaCl, pH 7.4, containing, on a molar ratio basis, a mixture of phosphatidyl choline:cholesterol:phosphatidyl glycerol of 8:10:1. Other liposome compositions may be used, for example recipes without cholesterol, as long as a periodate-oxidizable component containing vicinal hydroxyls (e.g., phosphatidyl glycerol) is present. Any method of liposome formation may be used that is common to those skilled int he art, including mechanical dispersion, detergent-assisted solubilization, or solvent-mediated dispersion.
2. Dissolve sodium periodate to a concentration of 0.6 M by adding 128 mg per ml of water. Add 200 μl of this stock periodate solution to each ml of the liposome suspension with stirring.
3. React for 30 min. at room temperature in the dark.
4. Dialyze the oxidized liposomes against 20 mM sodium borate, 0.15 M NaCl, pH 8.4, to remove unreacted periodate. This buffer is ideal for the subsequent coupling reaction. Chromatographic purification using a column of Sephadex G-50 also can be done. The periodate-oxidized liposomes may be used immediately to couple with superantigen molecules or they may be stored in a lyophilized state in the presence of sorbitol (Friede et al., 1993) for latter use.
5. Add a superantigen to the periodate oxidized liposome solution to obtain a 1 mg/ml concentration.
6. In a fume hood, add 20 microliters of 5 M sodium cyanoborohydride solution in 1 M NaOH (Aldrich) to each ml of the superantigen solution.
7. The reaction is mixed gently and incubated at room temperature for 6 hours.
8. Excess superantigen and cyanoborohydride are removed by size exclusion chromatography on a column of Sephadex G-50 or by dialysis using a membrane with a molecular weight cutoff of 100,000 daltons.
9. Ganglioside antigens isolated by the method described previously may be incorporated into the superantigen-containing liposomes by detergent dialysis. Add an amount of ganglioside representing twice the amount of phosphatidyl glycerol (on a molar basis) originally added to form the liposome (prior to periodate oxidation). To this solution add concentrated sodium deoxycholate to obtain a final concentration of 0.7% (w/w). Mix thoroughly using a vortex mixer. Finally, dialyze the liposome suspension against PBS, pH 7.5.

Conjugation of Glycoprotein Tumor Antigens to Superantigen Molecules

Glycoprotein antigens associated with tumor cells may be isolated and conjugated to superantigen molecules using chemical cross-linking methods that couple through both proteins' functional groups. Conjugation strategies useful in this regard are similar to those described for coupling peptide antigens to superantigen molecules (described elsewhere). Two methods are presented here, but they are not meant to represent an exhaustive treatment of all possible conjugation strategies. Other cross-linking methods may be successfully used to form similar complexes that fall within the scope of this invention.

Conjugation Using Dextran as a Carrier

1. Dissolve or buffer-exchange the periodate-oxidized dextran in 0.1 M sodium phosphate, 0.15 M NaCl, pH 7.2, at a concentration of 10–25 mg/ml. Other buffers having a pH range of 7–10 may be used with success as long as they do not contain competing amines (such as Tris). A reaction environment of pH 8–9 (in 0.1 M sodium bicarbonate) will give the greatest yield of reductive amination coupling.
2. Add 1–10 mg of superantigen (e.g., SEB) and an equivalent mass of glycoprotein antigen to each ml of the dextran solution. Mix to dissolve.
3. In a fume hood, add 0.2 ml of 1 M sodium cyanoborohydride (Aldrich) to each ml of the SEB/glycoprotein/dextran solution. Mix well. Alternatively, to avoid the toxicity problems of cyanoborohydride, an equivalent molar quantity of sodium borohydride may be added as reductant. If borohydride is used, a reaction pH of 9.0 in 0.1 M sodium bicarbonate buffer is appropriate.
4. React for at least 6 hours at room temperature. Overnight reactions also may be done.
5. To block excess aldehydes, add 0.2 ml of 1 M Tris, pH 8, to each ml of the reaction. If sodium borohydride was used as the reductant, this blocking step is unnecessary, because any remaining aldehydes would be reduced to hydroxyls.
6. If blocking agent is used, react for an additional 2 hours at room temperature.
7. Purify the conjugate from unconjugated SEB and glycoprotein by gel filtration using a column of Sephacryl S-200 or S-300. Removal of excess SEB and glycoprotein also may be done from a dextran conjugate by dialysis using a membrane with a molecular weight cut-off larger than that of the glycoprotein antigen or superantigen monomers.

Conjugation of Superantigen and Glycoprotein Antigens Using Heterobifunctional Cross-Linkers The heterobifunctional cross-linker Sulfo-SMCC may be used to directly attach superantigen molecules to glycoprotein tumor antigens. One end of the cross-linker is an NHS ester which reacts with amines on one protein to form amide bond derivatives terminating in maleimide groups. The maleimide intermediate then may be reacted with a second protein containing sulfhydryls to couple through a thioether bond. To use this type of cross-linker with a superantigen and glycoprotein, one of the molecules must first be modified to possess free thiol groups. Thiolation reagents such as 2-iminothiolane or SATA (Pierce) may be used for this purpose. The following protocol describes this conjugation approach.

1. Dissolve the glycoprotein to be thiolated at a concentration of 10 mg/ml in a non-amine containing buffer at pH 8.0 (e.g. 50 mM sodium phosphate, 0.15 M NaCl, pH 8.0, or 0.1 M sodium borate, pH 8.0 may be used).
2. Dissolve Traut's reagent (2-iminothiolane; Pierce) in water at a concentration of 2 mg/ml (makes a 14.5 mM stock solution). The solution should be used immediately. Add 50–100 µl of this stock solution to each ml of the glycoprotein solution.
3. React for 1 hour at room temperature.
4. Purify the thiolated protein from unreacted Traut's reagent by dialysis or gel filtration using 20 mM sodium phosphate, 0.15 M NaCl, 5 mM EDTA, pH 7.2. The addition of EDTA to this buffer helps to prevent oxidation of the sulfhydryl groups and resultant disulfide formation. Use the thiolated glycoprotein immediately.
5. Dissolve the superantigen of choice (e.g., SEB) at a concentration of 10 mg/ml in 0.1 M sodium phosphate, 0.15 M NaCl, pH 7.2.
6. Dissolve sulfo-SMCC (Pierce) at a concentration of 10 mg/ml in water. Immediately transfer 300 µl of this solution to each ml of the superantigen solution. Mix well.
7. React for 1 hour at room temperature.
8. Immediately purify the activated protein by gel filtration using a volume of Sephadex G-25 equal to 15 times the volume of the activation reaction. To perform the chromatography use 0.1 M sodium phosphate, 0.15 M NaCl, 0.01 M EDTA, pH 7.2 (conjugation buffer). The EDTA is present to prevent metal-catalyzed sulfhydryl oxidation to disulfides. Apply the reaction mixture to the column while collecting 0.5–1.0 ml fractions. Pool the fractions containing the activated superantigen (the first peak to elute from the column), and discard the fractions containing excess sulfo-SMCC (the second peak). Concentrate the activated superantigen to about 10 mg/ml using centrifugal concentrators with a molecular weight cut-off of 10,000 (Amicon). The activated protein should be used immediately or freeze-dried to maintain maleimide stability.
9. Dissolve the sulfhydryl-containing glycoprotein to be conjugated (prepared as described in steps 1–4) at a concentration of 10 mg/ml in the conjugation buffer containing the activated superantigen.
10. Allow the conjugation reaction to proceed for at least 2 hours at room temperature.
11. Remove excess glycoprotein or superantigen monomers from the conjugate by dialysis or gel filtration.

Example 4

Immunizing Constructs: Fusion Proteins

Fusion proteins consisting of peptides, superantigens, class I and class II molecules will be prepared by well defined methods.

Example 5

Immunizing Constructs: Preparation of Tumor Cells Transfected with Superantigen Genes and α-Gal Genes A. Tumor Cells Transfected with Superantigen Genes Tumor cells may be transfected with superantigen genes and a fusion gene of a tumor specific peptide and superantigen with or without MHC class II genes and/or accessory molecules such as B-7 and integrins to create a molecular construct expressing tumor specific antigen, superantigen, class II molecules, and accessory molecules on the cell surface to provide potent T cell stimulatory signals. The tumor cells are cotransfected with MART- I and HLA-A1 in order to increase their intrinsic immunogenicity.

The method of treatment involves binding of these superantigen-TAA conjugates or fusion proteins to class I positive antigen presenting cells. Once bound they would then be presented to a T cell population. Tumor cells transfected with superantigens would also serve as potent antigen presenting cells to the responder T cell population.

B. Transfection of Superantigen, HLA-class II and HLA-A1 Genes into Tumor Cells

This may be accomplished with the use of the enterotoxin or other superantigen plasmids, HLA-class II and HLA-A1 DNA transfected into various tumor cells by several well known techniques. These include calcium phosphate precipitation, electroporation and DEAE dextran transfection.

C. Methods of Anchoring The Transfected Superantigen to the Tumor Cell Membrane for Enhanced Expression DNA from SEB or other enterotoxins may be extracted from the original plasmid and converted to cDNA. An MHC class II gene may be used as a leader gene and placed upstream from the cDNA for SEB in order to anchor the SEB to the tumor cell membrane. A CMV expression vector may be inserted at the 5'end. MMTV DNA may also be used to carry the superantigen to the tumor cell surface. This construct inserted into tumor cells will anchor the superantigen to the tumor cell surface and prevent secretion of the enterotoxins by the tumor cells.

D. Viral Superantigen Transfection of Tumor Cells

Various vSAG expression plasmids are generated by cloning gene fragments from mammary tumor viruses into the puromycin plasmid. The vSAG transfectants are generated using 10 µg of appropriate plasmid with 15 µl Lipo-Fectamine (Life Technologies, Grand Island N.Y.) for 4 hour in serum-free medium, followed by incubation in complete medium overnite. The cells are plated at $1 \times 10^4$ cells/well in 24-well culture plates for 24 hours before the addition of G-418 (1 mg/ml; Life Technologist). Viable cells are analyzed and cloned by limiting dilution followed by selection with 25 µg/ml of puromycin (Sigma). Cotransfection with class I or class II plasmids will follow the same procedure.

E. Transfection of α-Gal Genes into Tumor Cells

Xenoreactive natural Abs recognize Galα1-3Galβ1-4GlcNAc(galactose α1-3-galactose-β1-4-N-acetylglucosamine) abbreviated as α-Gal. This antigen is expressed in the tissues of pigs, guinea pigs, rodents, dogs and cows but has not been detected in human tissues. It is expressed in endothelial cells and is thought to be a major antigenic target for hyperacute organ rejection in xenografts. Anti-Gal in a naturally occurring IgM antibody recently found to be present in large amounts in human serum. It binds to pig endothelial cells which express the α-Gal epitope. A triad of glycoproteins of molecular mass, 115, 125 and 135 kDa have been identified as the major targets of the surface of pig endothelial cells. After interaction with naturally occurring IgM antibodies xenografts undergo hyperacute rejection by a complement dependent mechanism within a few minutes. Surface expression of the ax-Gal epitope may be achieved by transfection of a cDNA clone encoding the α 1-3 galactosyl transferase (which transfers a terminal galactose residue with a α-1-3 linkage to a subterminal galactose and is missing in human and certain primate cells) into a human malignant tumor cell line such as melanoma or adenocarcinoma which does not express this epitope. The resulting transformed tumor cells with α-Gal expressed on their surface should be rapidly rejected by circulating α-Gal specific IgM antibodies in humans. The methodology of production of the gene is given below.

A cDNA clone, encoding the mouse α1-3-galactosyltransferase is produced by using the known sequence of this transferase and the PCR technique. Two oligonucleotides are synthesized:

αGT-1:
5'-GAATTCAAGCTTATGATCACTATGCTTCAAG-3' (SEQ ID NO:67), which is the sense oligonucleotide encoding the first 6 amino acids of the mature α1-3-galactosyltransferase and contains a HindIII restriction site; and αGT-2:
5'-GAATTCCTGCAGTCAGACATTATTCTAAC-3' (SEQ ID NO:68), which is the antisense oligonucleotide encoding the last 5 amino acids of the premature α1-3-galactosyltransferase and contains the in-phase termination codon and a PstI restriction site. The oligonucleotides are used to amplify a 1185-bp fragment from a C57BL/6 spleen cell cDNA library, which is subsequently purified, digested with HindIII and Pst I (Pharmacia LKB)restriction endonucleases, and directionally cloned into HindIII/Pst I-digested CDM8 vector. A plasmid (pαGT-3) is selected for further studies, sequenced to confirm the correct DNA sequence, and used for COS cells transfection. The IB4 lectin of *Griffonia simplicifolia* is obtained from Sigma.

Transfection of human tumor cells with the above transferase DNA is carried out by electroporation or other suitable transfection methods given herein. The resulting tumor cells become strongly reactive with human serum. The α-Gal transfected tumor cells may then induce rejection after implantation into SCID mice which have been reconstituted with human T and B cells and transfused with normal human plasma containing the naturally occurring human IgM antibodies specific for the α-Gal epitope. Similarly transfection of the transferase gene into tumors indigenous to humans or species such as Old World monkeys which do not synthesize the α-Gal determinant but do have naturally occurring circulating antibodies to α-Gal results in rejection of tumor compared to untransfected control tumors which are unaffected by the treatment. The animals show in vitro evidence of cytotoxicity against untransfected tumor cells after the rejection process is completed. Pretreatment with $10^5$–$10^7$ transfected tumor cells subcutaneously followed by implantation of untransfected tumor cells prevents the outgrowth of untransfected malignant tumor cells. Hence, the transfected tumor cells may function as a vaccine. Finally, transfected cells implanted into animals after untransfected tumors are established will induce rejection an established untransfected tumor. While the transferees gene is used as a model for expressing the α-Gal antigen on tumor cells, other genes which produce α-Gal expression on the tumor cell surface including but not limited to the α-Gal gene itself may be used to produce the same result.

The transferase gene will be co-transfected into tumor cells together with DNA coding for bacterial superantigens or mammary tumor viral (MMTV) superantigenic DNA. Alternatively, the two genes may be transfected sequentially. The transferase gene is ligated to the MMTV or enterotoxin gene and transfected into tumor cells by methods given below. The tumor cell will then express both superantigenic and α-Gal determinants on its surface. The cotransfected or dual transfected tumor cells may be used as a vaccine to prevent untransfected tumor growth or to combat the growth of established untransfected tumors by methods given above and well described in the art. Using B16 melanoma, A20 lymphoma or other models given in Example 20, $10^5$–$10^7$ transfected tumor cells may be implanted subcutaneously and 1–6 months later untransfected tumor cells will be implanted. Transfected tumor cells, $10^5$–$10^7$ may be given 3–10 days after the appearance of established tumors. Tumor growth will be arrested in both groups compared to untreated controls.

F. Preparation of Xenograft Antigen-Tumor Cell Complexes for Ex Vivo or In Vivo Immunization The xenograft antigen Gal(α1-3)Gal determinant also can be conjugated to intact tumor cells for production of a potent immunogen able to elicit an initial acute-phase hyperimmune response followed by protective immunity against unmodified tumor cells. This complex can be augmented with superantigen molecules, such as SEB, to further promote T cell activation and help create long-term protective immunity against the tumor cell line. The complex is formed ex vivo by covalently coupling the xenograft antigen carbohydrate to amine groups on proteins present on isolated tumor cells, creating an artificial xenograft antigen presentation on the outer cell membranes. The optional presence of a superantigen molecule in this preparation provides additional immune modulation beyond that possible from the presence of the carbohydrate antigen alone. Upon administration of these modified tumor cells into patients, antibodies and critical cells of the immune system will rapidly respond, resulting in a powerful response generated against the tumor immunogens. Subsequent initiation of the protective immunity against unmodified tumor cells then may occur days or weeks after modified tumor cell administration has been discontinued and the immunogen cells cleared from the body. Superantigen may be used to aid in this process either by being conjugated directly to the tumor cells prior to in vivo administration or by separate ex vivo or in vivo stimulation of T cell populations according to the methods outlined in this invention.

Xenograft antigen carbohydrate determinants can be conjugated to the surfaces of isolated tumor cells by methods known to those skilled in the art of bioconjugation. For instance, the purified carbohydrate containing the Gal alpha (1,3)Gal sequence can be directly coupled to the tumor cells by a reductive amination process using the reducing end of the polysaccharide, as already described elsewhere in this document for coupling the antigen to superantigen molecules. In this reaction scheme, a secondary amine linkage is formed between the reducing end of the carbohydrate and the amine groups on the cell surface. Alternatively, the carbohydrate antigen may be coupled to the cells through the use of another molecule able to react or bind to the cell surface and form a stable complex. In one such approach, a monoclonal antibody, specific for the tumor cell, is modified with the xenograft antigen and utilized as a targeting agent for binding to the cell surfaces and displaying the carbohydrate. The preparation of a xenograft antigen-antibody conjugate is described previously in this disclosure. In a second approach, the strong interaction between avidin (or streptavidin) and biotin is used to form a bridge linking the tumor cell surface to the xenograft polysaccharide,. In this case, the cell surface can be biotinylated using one of a number of reactive biotinylation reagents available commercially. For instance, NHS-LC -biotin (Pierce Chemical) can be reacted with the cells in a physiological PBS buffer at 50 mM concentration for 30 minutes at room temperature to effectively biotinylate amine groups on cell surface protein. Removal of excess biotin reagent is accomplished simply by washing the cells with PBS several times. The xenograft antigen carbohydrate then is covalently coupled to either avidin or streptavidin according to the methods previously outlined for modifying superantigens or antibodies with this molecule. Incubation of the biotinylated tumor cells with this avidin or streptavidin conjugate will result in the xenograft antigen coating the surface of the cells through the interaction of the avidin or streptavidin component with the sites of biotin modification.

Another option for this conjugation is the use of heterobifunctional cross-linkers which are able to react with functional groups on the tumor surfaces and also couple to the xenograft polysaccharide. An example of this strategy is to use the reagent $M_2C_2H$ [4-(N-maleimidomethyl) cyclohexane-I-carboxyl-hydrazide], a sulfhydryl-and carbonyl reactive cross-linker. The maleimide group of this reagent can form stable thioether linkages with sulfhydryl groups on proteins and other molecules. The hydrazide end of the cross-linker can react with carbonyl groups, such as aldehydes, to form hydrazone bonds. The hydrazones may be stabilized by reduction with sodium cyanoborohydride to create non-reversible linkages.

Use of $M_2C_2H$ to couple xenograft polysaccharide to tumor cell surfaces may be accomplished first by thiolating the cell surface to create available sulfhydryl groups. Reaction of cell surface proteins with Traut's reagent will yield free sulfhydryl groups (see the section titled "Conjugation of Superantigen and Glycoprotein Antigens Using Heterobifunctional Cross-Linkers". These sulfhydryl groups then are reacted with $M_2C_2H$ in PBS buffer (pH 7.2) to create cell surface modifications terminating in reactive hydrazide groups. The xenograft carbohydrate antigen then is reacted with the hydrazide group in the presence of sodium cyanoborohydride to create a covalent linkage. All of these reactions can be accomplished while maintaining tumor cell viability or by utilizing inactivated tumor cells. If inactivated cells are used, they must not be fixed with an amine-reactive chemical (e.g. formalin), as the functional groups necessary for the conjugation will be blocked. Inactivation by fixation may be done, however, after the conjugates have been produced.

G. Preparation of Xenograft Antigen or Superantigen or Xenograft Antigen-Superantigen Complexes Conjugated to Monoclonal Antibodies Directed Against Tumor Antigens for In Vivo or In Vitro Targeting The superantigen conjugation scheme relates to the production of a trimeric complex consisting of the glycolipid antigen involved in the hyperacute rejection process in xenotransplantation, the Gal alpha (1,3)Gal determinant making up the terminal region of the complex carbohydrate present on the cell surfaces of porcine tissues, plus a targeting component (such as a monoclonal antibody) and a superantigen molecule, such as SEB. The antibody would provide the specificity necessary for directing the conjugate to the surface of tumor cells in vitro or in vivo. The xenoantigen or superantigen alone may also be coupled to the monoclonal tumor specific antibody and the compound used for in vitro or in vivo targeting to tumor cells. The docking of these complexes on tumor cells would create a highly antigenic surface wherein the carbohydrate involved in the hyperacute rejection process would now be coating the surfaces of the tumor A superantigen molecule may also be present for additive T cell stimulation. There engineered cells may be employed in vivo to vaccinate the host against tumor or it may be used after tumors have been established. The same cells may be employed for in vitro stimulation of T cells as given in examples 11 and 12. The result would be a dramatic anti-tumor immune response, essentially destroying tumor cells as rapidly as xenotransplanted organs are destroyed in the hyperacute rejection process. The host may, be preimmunized to the α-Gal moiety by methods well known in the art. Six days to 6 months later than α-Gal-tumor cell conjugates may be administered either parenterally or intratumorally.

The xenograft antigen Gal alpha(1,3)Gal determinant is conjugated to superantigen according to the previously-described protocol. This complex can be subsequently conjugated with a targeting molecule, such as a monoclonal antibody or a recombinantly-designed peptide binding molecule directed against a tumor antigenic determinant, by cross-linking methods commonly known to those skilled in the art. The resulting trimeric complex is able to specifically bind to tumor cell surfaces in vivo, creating an artificial xenograft antigen presentation on the outer cell membranes. The presence of a superantigen molecule in the conjugate provides additional immune modulation beyond that possible from the carbohydrate antigen alone. Thus, T cell activation combined with a hyperacute rejection response is generated against the tumor, resulting in cell death and tumor necrosis. Such a trimeric conjugate can provide powerful cytotoxic effects directed against solid tumors and metastases. It also may initiate continued immunity against tumor cells, even after conjugate administration has been discontinued and the complex cleared from the body.

H. Conjugation of Xenograft Antigen or Superantigen or Xenograft Antigen-Superantigen Conjugate to an Antibody Using Heterobifunctional Cross-Linkers Sulfo-SMCC, a heterobifunctional cross-linker containing an amine-reactive NHS ester on one end and a sulfhydryl-reactive maleimide group on the other end, may be used to directly attach the xenograft antigen or superantigen or xenograft antigen-superantigen conjugate to antibody molecules directed against tumor antigens. The NHS ester end is first reacted with amines on one of the two components to form amide bond derivatives terminating in maleimide groups. The maleimide-activated intermediate then may be reacted with the second protein containing sulfhydryls to couple through a thioether bond. To use this type of cross-linker with the superantigen conjugate and an antibody, one of the molecules must first be modified to possess free thiol groups. Thiolation reagents such as 2-iminothiolane or SATA (Pierce) may be used for this purpose. The following protocol describes this conjugation approach by modifying first the xenograft antigen-superantigen complex with 2-iminothilane to create sulfhydryl groups. The antibody is then reacted with Sulfo-SMCC to create a maleimide-activated intermediate. The two derivatives then are reacted together to form the final conjugate.

1. Dissolve the xenograft antigen-superantigen to be thiolated at a concentration of 10 mg/ml in a non-amine containing buffer at pH 8.0 (e.g. 50 mM sodium phosphate, 0.15 M NaCl, pH 8.0, or 0.1 M sodium borate, pH 8.0 may be used).
2. Dissolve Traut's reagent (2-iminothiolane; Pierce) in water at a concentration of 2 mg/ml (makes a 14.5 mM stock solution). The solution should be used immediately. Add 50–100 μl of this stock solution to each ml of the xenograft antigen-superantigen conjugate solution.
3. React for 1 hour at room temperature.
4. Purify the thiolated protein from unreacted Traut's reagent by dialysis or gel filtration using 20 mM sodium phosphate, 0.15 M NaCl, 5 mM EDTA, pH 7.2. The addition of EDTA to this buffer helps to prevent oxidation of the sulthydryl groups and resultant disulfide formation. Use the thiolated xenograft antigen-superantigen conjugate immediately.
5. Dissolve the antibody of choice (e.g., a monoclonal antibody directed against a tumor antigen) at a concentration of 10 mg/ml in 0.1 M sodium phosphate, 0.15 M NaCl, pH 7.2.
6. Dissolve sulfo-SMCC (Pierce) at a concentration of 10 mg/ml in water. Immediately transfer 300 μl of this solution to each ml of the antibody solution. Mix well.

7. React for 1 hour at room temperature.
8. immediately purify the activated antibody by gel filtration using a volume of Sephadex G-25 equal to 15 times the volume of the activation reaction. To perform the chromatography use 0.1 M sodium phosphate, 0.15 M NaCl, 0.01 M EDTA, pH 7.2 (conjugation buffer). The EDTA is present to prevent metal-catalyzed sulfhydryl oxidation to disulfides. Apply the reaction mixture to the column while collecting 0.5–1.0 ml fractions. Pool the fractions containing the activated antibody (the first peak to elute from the column), and discard the fractions containing excess sulfo-SMCC (the second peak). Concentrate the activated antibody to about 10 mg/ml using centrifugal concentrators with a molecular weight cut-off of 10,000 (Amicon). The activated antibody should be used immediately or freeze-dried to maintain maleimide stability.
9. Dissolve the sulfhydryl-containing xenograft antigen-superantigen conjugate (prepared as described in steps 1–4) at a concentration of 10 mg/ml in the conjugation buffer containing the activated antibody.
10. Allow the conjugation reaction to proceed for at least 2 hours at room temperature.

Similar procedures may be used for conjugating superantigen or xenograft antigen alone to the tumor specific monoclonal antibody. To limit the amount of superantigen in the final trimeric complex(and thus its potential toxicity in vivo), the xenograft antigen carbohydrate may be first conjugated to the antibody as described in the previous method for conjugating this antigen with superantigen. A superantigen molecule then can be thiolated and the antibody-carbohydrate conjugate activated with Sulfo-SMCC as described above. Mixing these two intermediates in ratios designed to limit the amount of superantigen in the final complex (a low ratio of superantigen:antibody conjugate) will result in a preparation having fewer molecules of superantigen in the therapeutic preparation. Upon in vivo administration, the degree of toxicity can be thus controlled by modulating the amount of superantigen in the trimeric complex.

I. DNA Transfer

The experimental introduction of DNA into cells is accomplished by methods that (1) form DNA precipitates that can be internalized by the target cell; (2) create DNA-containing complexes whose charge characteristics are compatible with DNA uptake by the target cell; or (3) result in the transient formation of pores in the plasma membrane of a cell exposed to an electric pulse, pores of sufficient size to allow DNA to enter the target cell. The factors that determine which method one selects are (1) the duration of expression required i.e., transient vs. stable expression, and (2) the type of cell to be transfected. The specific details of each procedure are described here. Transfections may be carried out by well established methods including electroporation, calcium phosphate precipitations and DEAE Dextran.

1. Transfection Methods A. Calcium Phosphate Transfection Method

The most commonly used method to transfer DNA into recipient cells is the co-precipitation of the DNA of interest with calcium phosphate, after which the precipitate is added to the cells. With this technique, DNA entering the cell is taken up into phagocytic vesicles. Sufficient quantities of DNA enter the nucleus of the treated cells to allow relatively high frequencies of genetic transformation. This procedure has been shown to be appropriate for the transfer into a variety of cell lines of single-copy genes present in the total genomic DNA derived from a donor cell or tissue sample. Using a variety of cell types, transfection efficiencies of up to $10^{-3}$ have been obtained. This is the method of choice for the generation of stable transfectants.

Variations of the basic technique have been developed. If the experiment involves the transfer of plasmid DNA, one may choose to include high-molecular-weight genomic DNA isolated from a defined cell or tissue source. The addition of such DNA, called carrier DNA, often serves to increase the efficiency of transformation by the plasmid DNA. Upon arrival of the plasmid DNA/carrier DNA calcium phosphate co-precipitate to the nucleus of the treated cell, the plasmid DNA appears to integrate into the carrier DNA, often in the tandem array, and this assembly of plasmid and carrier DNA, called a transgenome, subsequently integrates into the chromosome of the host cell.

Another procedural option is the addition of a chemical shock step to the transfection protocol. Either dimethylsulfoxide or glycerol are appropriate. The optimal concentrations and lengths of treatment vary from cell line to cell line. The use of these agents can dramatically affect cell viability.

Chen and Okayama (1987) carefully optimized this transfer technique. They reported that incubation of the cells and the co-precipitate is optimal at 35□ C. in 2–4% $CO_2$ for 15–24 hours; that circular DNA is far more active than linear DNA, and that an optimal, finer precipitate is obtained when the DNA concentration is between 20–30 mg/ml in the precipitation mix. If the protocol presented here does not yield the desired result, it may be wise to alter the incubator temperature, $CO_2$ concentration, and DNA concentration to those just cited. However, those temperature and $CO_2$ concentrations are not optimal for cell growth and should be maintained only temporarily.

Method

Day 1: Seed $1.3 \times 10^6$ cells per 100-mm dish. Cells should be about 75% confluent when used to seed the dishes.

Day 2: Prepare a large calcium phosphate cocktail mixture to transfect many plates simultaneously. Protocol is given for 1 ml (or 1×100-mm dish equivalent) of solution. Scale up the amounts as necessary, and allow for an appropriate amount of sample-transfer errors. Adherence to sterile technique is critical. Use sterile reagents, tips, and tubes.

1. Add 1–20 g DNA (1 mg/ml in sterile TE, pH 7.05) to 0.45 ml sterile $H_2O$. Note: First "sterilize" DNA by ethanol precipitation with NaCl (0.1 M final aqueous concentration) and 2×volume 200% ethanol.
2. Add 0.5 ml 2×HBS. Mix well.
3. Add 50 1 of 2.5 M $CaCl_2$ vortex immediately.
4. Allow the DNA mixture to sit undisturbed for 15–30 minutes at room temperature.
5. Add 1 ml of the DNA transfection cocktail directly to the medium in the 100-mm dish (plated with cells on day 1).
6. Incubate the dishes containing the DNA precipitate for 16 hours at 37□ C. Remove the media containing the precipitate and add fresh complete growth media.
7. Allow the cells to incubate for 24 hours. Post incubation, the cultures may be split into selective media. Split cultures 1:5; however, to isolate individual colonies for further analysis, split cultures 1:10 and 1:100.

B. DEAE Dextran Transfection Method

DEAE dextran transfection is the method of choice for transient transfection of cells in culture. This is due to the relative ease of preparation of the DNA/DEAE dextran mixture for transfection as well as the high efficiency of transient gene transfer and expression that can be accomplished with this technique. DEAE dextran mixture is prepared, and the DNA sample of interest is added, mixed, and then transferred to the cells in culture. This method yields transfection efficiencies of as high as 80 percent. DNA introduced into cells with this method appears to undergo mutations at a higher rate than that observed with calcium-phosphate-mediated transfection.

Day 1: 1. Seed cells at a concentration of $2\times10^4$ cells/cm$^2$ in a total volume of 2 ml/well ($1.92\times10^5$) cells/well of a six-well cluster dish. Cells should be about 75% confluent when used to seed the dishes.

Day 2: 1. Resuspend 0.5 ml DEAE Dextran (in TBS). Final DEAE Dextran concentration should be about 0.04%.
2. Observe cell monolayers microscopically. Cells should appear about 60–70% confluent and well distributed. Bring all reagents to room temperature.
3. Aspirate off growth media and wash monolayer once with 3 ml of PBS followed by one wash with 3 ml of TBS.
4. Aspirate off TBS solution and add 100–125 ml of the appropriate DNA/DEAE-Dextran/TBS mixture to the wells.
5. Incubate dishes at room temperature inside a laminar flow hood. Rock the dishes every 5 minutes for 1 hour, making sure the DNA solution covers the cells.
6. After the 1-hour incubation period, aspirate off the DNA solution and wash once with 3 ml of TBS followed by 3 ml of PBS.
7. Remove the PBS solution by aspiration and replace with 2 ml of complete growth media containing 100 M chloroquine. Incubate the dishes in an incubator set at 37□ C.+5% $CO_2$ for 4 hours.
8. Remove the media containing chloroquine and replace with 2–3 ml of complete growth media (no chloroquine).
9. Incubate the transfected cells for 1–3 days, after which the cells will be ready for experimental analysis. The exact incubation period will depend on the intent of the experiment. We find that optimal expression of transfected cytokine genes and cell-surface proteins occurs at 3 days post transfection.

C. Electroporation

Electroporation is a process whereby cells in suspension are mixed with the DNA to be transferred. This cell/DNA mixture is subsequently exposed to a high-voltage electric field. This creates pores in the membranes of treated cells that are large enough to allow the passage of macromolecules such as DNA into the cells. Such DNA molecules are ultimately transported to the nucleus and a subset of these molecules are integrated into the host chromosome. The redosing of the membrane pores is both time-and temperature-dependent and thus is delayed by incubation at 0□C., thereby increasing the probability that the molecule of interest will enter the cell.

Electroporation appears to work on virtually every cell type. With this technique, the efficiency of gene transfer is high for both transient transfection and stable transformation. One important technical difference between electroporation and other competing technologies is that the number of input cells required for electroporation is considerably higher.

Method
1. Harvest, by trypsinization, and pellet exponentially growing cells, then wash twice with electroporation buffer.
2. Resuspend cells in electroporation buffer at a concentration of $2-20\times10^6$ cells/ml in an electroporation cuvette.
3. Add 5–25 mg of DNA that has been linearized to the cell suspension.
4. Insert or connect the electroporation electrode according to the manufacturer's instructions and subject cell/DNA mixture to an electric field (pulse).
5. Return cell/DNA mixture to ice and incubate for 5 minutes.
6. Plate cells in non-selective medium. Biochemical selection may be carried out 24–48 hours later.

Example 6

Immunizing Constructs: Pharmaceutical Compositions and their Manufacture

The pharmaceutical composition of the invention comprises formulations that as such are known within the field but now containing our novel conjugate. Thus, the compositions may be in the form of a lyophilized particulate material, a sterile or aseptically produced solution, a tablet, an ampoule etc. Vehicles such as water (preferably buffered to a physiologically pH-value such as PBS) or other inert solid or liquid material may be present. In general terms, the compositions are prepared by mixing the conjugate dissolving it in or binding it to or otherwise combining it with one or more water-insoluble or water-soluble aqueous or non-aqueous vehicles, if necessary together with suitable additives and adjuvants. It is imperative that the vehicles and conditions shall not adversely affect the activity of the conjugate. Water as such is comprised within the expression vehicles.

Example 7

Immunizing Constructs: Administration and Methods of use

Normally the conjugates will be sold and administered in predispensed dosages, each one containing an effective amount of the conjugate that, based on the result now presented, is believed to be within the range 1 ng–100 mg. The exact dosage varies from case to case and depends on patient's weight and age, administration route, type of cancer and superantigen. The administration route is as commonly known within the field, i.e. a target cell lysing effective amount or a therapeutically effective amount of a conjugate according to the invention is contacted with the target cells. For the indications specified above this mostly means parenteral administration, such as injection or infusion (subcutaneously, intravenously, intra-arterial, intramuscularly) to a mammal, such as a human being. The conjugate may be administered locally or systemically to the individual to be treated. By "target cell activating amount" is contemplated that the amount is effective in activating and directing CTLs to destroy the target cell.

Example 8

Effector Cells: Preparation of Effector Cells with Tumor Specificity

Immunization Procedures: in vivo Immunization Methodology

The initial step will involve immunization of the host with irradiated tumor cells or TAA attached to class I cells and will be given subcutaneously in close proximity to the regional lymph nodes with or without a bacterial adjuvant such as BCG or Corynebacterium parvum. Alternatively, irradiated tumor cells transfected with TAA and HLA-A 1 genes may be used as an in vivo immunogen. The lymph node cells are harvested 10 days later and tissue cultured for further in vitro immunization with peptides and superantigens as given below. The basic in vivo method for immunization is given herein.

A. Tumor Vaccination. Patients will have cryopreserved autologous tumor cells for subsequent tumor vaccination and IVS culture. Fresh resected tumors will be dissociated under sterile conditions into single cell suspensions by mechanically mincing tumor into 5-mm$^3$ pieces followed by enzymatic digestion. Generally, 1 g of tumor will be digested in a minimum volume of 40 ml of an enzyme mixture consisting of HBSS containing 2.5 units/ml of hyaluronidase type V, 0.5 mg/ml of collagenase type IV, and 0.05 mg/ml of deoxyribonuclease type I (all from Sigma Chemical Co., ST. Louis Mo.). The digestion will be performed at room temperature with constant stirring in a trypsinizing flask for 2 to 6 h. The resulting cell suspension will be filtered through a layer of No. 100 nylon mesh (Nytek: TETKO, Inc., Briarcliff Manor, N.Y.) and cryopreserved in 90% human AB serum (GIBCO, Grand Island, N.Y.) plus 10% dimethyl sulfoxide (Sigma) as −178□ C. in liquid nitrogen for subsequent immunization and culture.

For immunization, cryopreserved tumor cells will be thawed and washed twice in HBSS, Viable tumor cells will be irradiated to a dose of 25 Gy, counted by trypan blue exclusion, and resuspended so that a volume of 0.2 to 0.4 ml contained 1 to $2 \times 10^7$ viable tumor cells and $10^7$ colony-forming units of fresh-frozen Tice BCG (supplied by M. G. Hanna, Bionetics Research, Inc., Rockville, Md.). Patients will be vaccinated i.d. at two sites approximately 10 cm from superficial inguinal, or if necessary, axillary LN. Lymph node regions with previous dissections or clinical evidence of tumor will be avoided.

Methods for Obtaining and Purifying Tumor Specific Effector Cells:

A. Immunization in vitro of PBL, TIL, Eluted T Cells from Immobilized Antibody Columns or Tumor Vaccine Primed Lymph Node Cells with Tumor Peptides plus Selected Superantigens or Mutant Superantigen (if Vβ clonality is identified).

Regional lymph node cells draining tumor sites or lymphoid cells obtained after tumor vaccine priming or peripheral blood T cells or TIL may be used as a source of T cells. T cells may also be obtained from TIL either before or after tumor vaccine immunization in vivo by methods given below.

B. Isolation and Culture of Tumor Draining Lymph Node Cells

Approximately 10 days after in vivo immunization, enlarged draining LN will be removed for culture. A single cell suspension of LN cells will be obtained by mechanical dissociation. Briefly, LN will be minced into 2-mm3 pieces in cold HBSS with a scalpel. The fragments will be then pressed through a stainless steel mesh with a glass syringe plunger. The resultant cell suspension will be filtered through nylon mesh and washed in HBSS. Cultures will be established in 300-ml culture bags (Livecell Flasks: Fenwal, Deerfield, Ill.) with 200 to 250 ml of CM containing 1 to $2 \times 10^5$ LN cells/ml and 1 to $4 \times 10^5$ irradiated (60 Gy) tumor cells/ml. After 24 hours staphylococcal enterotoxin B (SEB) will be added at a concentration of 1 picogram/ml to 20 µg/ml for 2 days. CM consisted of RPMI 1640 with 10% human AB serum, 2 mm fresh L-glutamine, 1 mM sodium pyruvate, 100 mg/ml of streptomycin, and 50 mg/ml of gentamicin (all from GIBCO. Grand Island, N.Y.). IL-2 (Cetus, Emeryville, Calif.: provided by Cancer Treatment Evaluation Program, National Cancer Institute) was added at the initiation of the cultures at a concentration of 600 IU/ml (1 Cetus unit=6 IU of IL-2). Culture bags will be incubated at 37 in humidified 5% $CO_2$. Cell counts from aliquot obtained from random bags will be followed to observe for lymphoid cell proliferation. LN cells will be harvested when cells reached maximal density usually after a total of 5–7 days in culture followed by IL-2 at 24 IU/µl for 3 days. The cells will be washed once at the end of SEB incubation and before the addition of IL-2.

For comparative analysis, PBL, will be obtained from patients the same day as the LN harvest. PBL will be isolated by Ficoll-Hypaque gradients from 60 ml of heparinized blood samples. The PBL will be placed in culture utilizing 24-well tissue culture plates at the same cell density as LN cells. PBL will be harvested at maximal cell density and characterized by phenotype analysis and cytotoxicity.

C. Isolation of PBL

PBL were separated by Ficoll/Hypaque sedimentation. Cells will be recovered from the interface, washed in PBS, and pelleted for RNA extraction.

D. Isolation of TIL and Tumor Cells

TIL will be isolated from fresh surgical biopsies as described earlier with minor modifications. Briefly, tumor tissues were minced into 1 -mm3 pieces, which are then dissociated into single cell suspensions in Dulbecco's modified minimum essential medium (Gibco, Grand Island, N.Y.) supplemented with 10% heat-inactivated human AB serum (NABI, Miami, Fla.), 0.05% collagenase (type 4; Sigma Chemical Co., St.. Louis, Mo.) and 0.002% DNase (type 1; Sigma) on a magnetic stirrer for 1 h. Subsequently, the tissue digests are washed and passed through a nylon mesh and TIL and tumor cells are separated on discontinuous (75%/100%) Ficoll/Hypaque gradients. Lymph node lymphocytes will be obtained by mechanical dissociation of tissues, followed by washing in medium and centrifugation on Ficoll/Hypaque gradient (Newell, K. A., et al., *Proc. Nat'l. Acad. Sci.,* 88, 1074, 1991)).

E. TIL Culture

Cryopreserved suspensions of tumor cells/TIL will be defrosted, washed, and separated by allowing tumor cells to adhere to the surface of plastic wells. The recovered non-adherent TIL are transferred to wells of 6-well plates and cultured in serum-free AJM-V medium (Gibco) supplemented with 6000 (U/ml of IL-2 (Cetus-Chiron, Emeryville. Calif.) for 8 days. Tumor cells are cultured as adherent monolayers in Dulbecco's modified Eagle's medium (Gibco) supplemented with 10% (v/v) of fetal calf serum.

F. Immobilized Antibody Columns for Isolation of T Cells with Vβ Specificity from Blood and Tissues Antibodies to various Vβ subsets will be immobilized on inert solid supports and incubated with blood cells and/or tissue cells to include bone marrow and cells and TIL. The bound T cells will be eluted with various buffers. Biocompatible inert supports will include polystyrene, polyacrylamide, nylon, silica and charcoal as well as others known in the art. They will be derivatized for covalent binding of antibodies with well known agents in the art including Heterobifunctional compounds, carbodiimide and glutaraldehyde. The enriched population of Vβ bearing T cells will then be further expanded in IL2 and used for in vitro immunization or anergization with the appropriate superantigens, peptides and superantigen-peptide conjugates.

Example 9

Effector Cells: General Procedures for in vitro Immunization Using Tumor Associated Peptides (TAA) and Superantigens, Superantigen-Peptide Conjugates and Tumor Cell Transfectants to Produce Tumor Specific Effector Cells A. Stimulator Constructs PBMC to serve as source of HLA-A1 for peptide binding will be separated from peripheral blood of HLA-A2+ patients and healthy donors by centrifugation of Ficoll-Hypaque gradients and used as fresh or cryopreserved samples. Cryopreserved groups of autologous PBMC will be thawed, washed twice in PBS, resuspended at 5 to $8 \times 10^6$ cells/ml in CM and pulsed with 1 mg/ml peptide in 15-ml conical tubes (5 ml/tube) for 3 h. at 37□ C. These PBMC (stimulators) will then be irradiated at 3000 rads, washed once in PBS, and added to the responder cells at responder stimulator ratios ranging between 1:3 and 1:19.

B. Effector T Cells

Effector T cells will be derived from PBMC, bone marrow, lymph nodes, TIL or eluates obtained from immobilized antibody columns from patients and healthy donors by centrifugation on Ficoll-Hypaque gradients and used as fresh cryopreserved samples. To generate responder T cells from TIL cultures, the dissociated tumor suspension will be cultured for 1 to 2 days in 10% FCS RPMI 1640 medium to allow tumor cell adherence. The lymphocytes, recovered from the non-adherent fraction will be used for the induction of peptide-specific CTL as described below.

Sequential in vitro Immunization with Peptide and Superantigen

Effector lymphocytes will be stimulated with peptide bound to irradiated PBMC (stimulator cells) for 1–3 days. Dendritic cells, macrophages or other class I bearing cells may be used. The T cells will then be analyzed for Vβ profile. A superantigen such as enterotoxin A or B will then be added to the culture (1 picogram to 10 microgram). If a given Vβ predominance is noted after peptide stimulation, then a superantigen known for its ability to specifically stimulate that Vβ subset will be selected. Culture will proceed for 1–3 days. The Vβ profile of stimulated T cells will then be rechecked. IL-2, 12–25 IU, will be added for an additional 3 days and the cells will be harvested for use. The optimal timing of superantigen introduction after peptide stimulation is between 3 and 14 days. APCs of all kinds such as dendritic cells, B cells or macrophages with appropriate class II binding sites for superantigens may be used or the superantigens may be presented alone or in immobilized form without APCs Before IL-2 administration effector cells may be restimulated weekly by washing and replating in 24 well plates at a concentration of $2.5 \times 10^5$ cells/ml in CM. This may be continued for 3–10 cycles until enough cells are available for IL-2 expansion. T cells may be cloned 7 days after the several cycles of stimulation in 96 well round bottom plates at 0.3 cells/well with $5 \times 10^4$ stimulator peptide-PBMC, superantigen and 25–50 U recombinant IL-2 in a volume of 200 ml.

For long term growth, clones will be transferred to 24 well plates and $1 \times 10^6$ cells/well and stimulated weekly with superantigen plus $5 \times 10^5$ peptide-PBMC and 25–50 U/ml of IL-2. After clones grow to greater than $2 \times 10^6$ cells, they will be maintained by culturing with superantigen only for 48 hours washing to remove superantigen and replating in fresh media for 5–7 days with 25–50 U/ml IL-2. The initial incubation will be with MART-1 for 1–3 days with the latter reagents followed by Vβ profiling and restimulation with superantigen by methods given above. The MART-1 will be presented attached to HLA-A1+ cells of PBMC. Cytotoxic activity will be tested after the first and/or second rounds of sequential stimulation with peptide and superantigen given below.

Alternatively, stimulants such as peptide-superantigen conjugates or fusion proteins or tumor cell transfectants expressing α-Gal, superantigens, class II and/or class I molecules will be used. The initial incubation will be 1–3 days with the latter reagents followed by Vβ profiling and restimulation by methods given above. The peptide-superantigen conjugates and fusion proteins will be presented attached to HLA-A1+ class II positive APCs of multiple types including but not limited to peripheral blood, dendritic cells, macrophages or B cells.

Tumor specific hybridomas may also be generated by immunization in vitro of human T cells with peptide and superantigen given simultaneously or sequentially (in either order) or an immunotherapeutic superantigen-peptide conjugate or tumor cell transfectants expressing superantigens, class II and /or class I molecules for 1 to 6 days followed by further expansion in IL-2 (~650 U/ml) for 1–6 days. The expanded T cells may then be fused to a thymoma and cloned by limiting dilution or other methods well known in the art. Cells may be cultured for example in complete tumor medium composed of Eagle's MEM supplemented with 10 μM 2-mercaptoethanol, 10% fetal calf serum, 10% Mishell-Dutton Nutrient cocktail, 100 U/ml penicillin G and 200 μg/ml streptomycin sulfate but other known culture media well known in the art may be used.

For superantigen immunization in vitro, various antigen presenting cells may be used including class II positive T cells. Purified class II molecules alone or in immobilized form may substitute for APCs. Moreover, T cells may be activated by some superantigens without APCs when presented to T cells in immobilized form or in the presence of various cytokines such as IL-1, IL-2, IL-4 or IL-6. Various adhesion molecules such as ICAM-1 and VCAM-1 may be used together with superantigens and class II positive APCs or immobilized class II peptides to augment the T cell response. Peptide immunization may also involve the binding of peptides to class I bearing APCs of multiple origins. Various cytokines including but not limited to IL-1, IL-2, IL-4, IL-12 may be used in vitro or in vivo to expand the antigen specific clone of T cells and avert the development of T cell anergy.

In addition, the Fas ligand (FasL) has been identified as a type II transmembrane protein that belongs to the TNF family of proteins. It has been shown that these two related receptor-ligand molecular systems signal apoptosis through closely related but distinct pathways. T cell phenotypes which have diminished expression of Fas or FasL show delayed anergy induction and shortened non-reactivity kinetics compared to Fas expressing cells. Activation cell death induced by superantigens (AICD) in vitro or in vivo may be averted using T cells which are Fas deficient, which are downregulated for Fas or FasL receptors, or which have the Fas receptor blocked. The addition of Fas-IgG fusion protein during the superantigen activation phase will also prevent AICD or anergy induction. Measures including but not limited to the above which protect the T cells from anergy induction or AICD will demonstrate prolonged survival and enhanced tumoricidal properties in vivo after activation by tumor peptide and superantigen or tumor peptide-superantigen conjugates in vitro.

D. Prevention of Anergy and Apoptosis in T Cells Stimulated in Vitro with Peptides and Superantigens or Peptide-Superantigen Conjugates Apoptosis of T cells or anergy induction may occur after in vivo activation of T cells or T cell hybridomas with superantigens. Exposure of T lymphocytes to superantigens such as SEB induces a strong proliferative response. However, prolonged exposure with subsequent re-stimulation of the responding T cell population with SEB leads to the apoptotic events of activation-induced cell death (AICD). In contrast, T cells derived from either Fas deficient 1 pr or Fas ligand deficient gld autoimmune mouse strains fail to undergo AICD and, instead, mount a vigorous proliferative response. Hence, the decision of whether a lymphocyte will mount a beneficial (anti-tumor, antiparasite) or an auto- aggressive response may depend on the functional state of its anti-apoptotic machinery. For effective anti-cancer therapy it is necessary to devise methods that prevent superantigen induced apoptosis in order to sustain tumoricidal function of the T cells that are infused into tumor bearing hosts.

A small number of genes have been shown to be essential for mediating programmed cell death after activation of the TCR/CD3 complex. Superantigens mediate apoptosis in T cells via similar signaling and molecular networks. Blocking the expression of essential genes will rescue cells from superantigen-induced apoptosis. The tumor suppressor gene or p53 and protooncogene c-myc are essential in some forms of T cell death. c-Myc acts as bivalent regulator determining either cell proliferation or apoptosis depending on whether free movement around the cell cycle is supported by growth factors or is limited by growth factor deprivation or treatment with other cycle blocking agents. The oncosuppressor gene p53 may initiate apoptosis by causing $G_1/S$ arrest in cells expressing c-myc. p53 exerts its effect at the initiation of apoptosis and is induced by agents that cause DNA strand breakage such ionizing radiation or etoposide. A second class of genes appear to offer protection and rescue cells from superantigen-induced T cell death. The best characterized are Bcl-2 and ras. Indeed, proto-oncogenes and oncosuppressor genes including Bcl-2 which inhibit apoptosis and myc and p53 which enhance apoptosis operate at different points along the apoptosis pathway.

Superantigen induced apoptosis is mediated via activation of the Fas and Fas ligand receptors. The resulting tyrosine phosphorylation of multiple cellular proteins temporarily linked to Fas ligation is required for the development of apoptosis. Moreover, Fas ligation, protease activation and cyclin dependent kinase function may act in series to mediate superantigen driven apoptosis. An increase in intracellular calcium and activation of protein kinase C are essential for superantigen mediated apoptosis. Apoptosis at the level of T cell receptor signaling is mediated by Nur77.

Mutations of genes involved in apoptosis including Fas, Fas ligand and hematopoietic cell phosphatase (Hcph) have been identified in animal models of autoimmune disease. A defect in Fas is encoded by the 1 mutation of certain autoimmunity-prone mouse strains and overexpression of the anti-apoptotic proto-oncogene Bcl-2 gene produces autoimmune symptoms. Mutation of the Nur 77 gene results in potent anti-apoptotic effects.

Superantigen mediated stimulation results in $Ca^{++}$ dependent, endonuclease-mediated cell killing depending on the activation status of protein kinase C (PKC). These nucleases may be present constitutively or they may be inducible. Phorbol esters prevent $Ca^{++}$ dependent apoptosis in response to superantigen stimulation suggesting that activation of protein kinase C abrogates cell suicide. Protective effects of PKC occur after activation by IL-1 which raises intracellular diacylglycerol a PKC stimulator.

Superantigens may induce AICD via the TCR/CD3 signaling pathways and activate similar genetic and metabolic sequences. Hence, anti-apoptotic strategies aimed at inhibiting the TCR/CD3 signaling and activation pathways would be applicable to superantigens as well.

Pro-apoptotic molecules induced by superantigen stimulation of T cells including but not limited to the myc, Nur 77, p53, Hcph phosphatase, Fas and ras may be inhibited by the addition of corresponding anti-sense molecules or intracellular neutralizing antibodies using oligonucleotides or transfected DNA that are specific for the genes or gene products given above. These antisense molecules and antibodies may interfere with all aspects of AICD without affecting lymphokine production. Additional anti-apoptotic molecules include endonucleases and various proteases which are capable of degrading the above pro-apoptotic genes or gene products. In addition, downregulation of genes and gene products for the various pro-apoptotic molecules also be desirable to avert apoptosis.

Additional anti-apoptotic molecules are NFκα transcription factors. Proteases which hydrolyze INFκα, the inhibitor of NFκα, produce additional anti-apoptotic effects. In addition, overexpression in the cell of NFκα would serve as an anti-apoptotic stimulus. Moreover, inducers of NFκα such as adriamycin and ionizing radiation would also serve as anti-apoptotic molecules. During superantigen stimulation of T cells it would be desirable to take steps to upregulate the activity of NFκα in order to avert apoptosis.

Anti-apoptotic strategies following superantigen activation of T cells may involve selective pharmacologic interference with tyrosine phosphorylation by drugs which include but are not limited to Herbimycin, Genistein and Spaurosporin. Cyclosporin A which blocks nuclear gene transcription may be used to inhibit apoptosis. Dexamethasone will inhibit superantigen induced apoptosis via interference with protein kinase C activation. Protein kinase inhibitors such as H-7 or H-8 will also inhibit superantigen mediated apoptosis. Superantigen mediated apoptosis which involves $Ca^{++}$ influx and macromolecular synthesis may be prevented by the addition of EGTA, cycloheximide, actinomycin D and zinc. The addition of Fas-IgG or Fas-Fc to the media in the course of superantigen stimulation may also inhibit surface activation of Fas. An additional anti- apoptotic strategy would be to add cytokines which include but are not limited to IL-4, IL-10 alone or together with LPS and TGFβ to the media. TGFβ is desirable since it promotes TH-1 cell production and differentiation after superantigen exposure.

Additional mechanisms for downregulating the expression of the pro-apoptotic molecules induced after superantigen stimulation would include creating deletions or mutation of the coding sequences for these molecules. Overexpression of coding sequences for anti-apoptotic molecules and interference with protein factors that bind to ribosomal DNA strands essential in pro-apoptotic gene regulation would also downregulate pro-apoptotic molecular expression. Genetic methods for producing overexpression of an anti-apoptotic stimulus include but are not limited to translocation of a promoter gene to a position near a strong enhancer on the other side of a chromosomal breakpoint which may result in an appropriate activation or overexpression of a coding sequence. Interference with the process of the readout of genetic information by a transcriptional protein and coding gene could prevent the production of pro-apoptotic molecules. Anti-apoptotic effects could also be produced by interference with pro-apoptotic gene synthesis or end product function by inhibiting the capping at the 5' end which is responsible for increasing the efficiency of translation from RNA to proteins and interfering with key signaling points which control production of molecules such as the Ras super family of monomeric GTPases containing Rho, Race and Rab. If Ras is inhibited, cellular differentiation or proliferation which is normally induced by activated receptor tyrosine kinases is interdicted. Regulatory protein systems which activate tyrosine kinases or inhibit them, focus on the major systems of activation such as Ras or Myc or Jun. Inhibition of the activator sequences required in apoptosis would promote anti-apoptotic effects. Anti-apoptotic effects could also be induced by interference with the splicing events in which introns are trimmed out of the genetic sequence of the proapoptotic genes.

Superantigen induced apoptosis is characterized by cell and chromatin condensation followed by nuclear and DNA fragmentation consistent with the activation of an endogenous nuclease which cleaves at internucleosomal sites. Interference with endonucleases which produce DNA fragmentation and are inducible during superantigen-mediated apoptosis would be desirable to avert apoptosis. These endonucleases are anionic proteins of molecular weight greater than 110 kd with a pH optimum of 7.5 and a double stranded cleavage preference. They are inhibitable with various protease inhibitors which may be activated or transfected into the cell. Inhibition of protease activity which may be responsible for activation of cyclin-dependent kinases during apoptosis and interference with degradation of an intracellular protease substrate which is normally cleared during Fas induced apoptosis might also be desirable to produce anti-apoptotic effects. Hence, activation of intracellular proteases by protease inhibitors may promote resistance to apoptosis. Moreover, pertussis toxin (PTX) may also be used to interfere with superantigen-induced apoptosis. PTX interferes with G1-protein dependent signal transduction from cell surface receptors. The S1 subunit of PTX ribosylates sensitive Gα subunits resulting in ligand induced exchange of GCP for GTP and blockade of the Gα subunit.

An additional anti-apoptosis strategy would be to use antibody to CTLA-4 to prevent apoptosis after superantigenic stimulation of T cells in vitro or in vivo. The anti CTLA-4 may be added to the media coordinate with superantigen or it may be given at repeated intervals of 1 to 4 days after T cell stimulation in vitro. It may also be given coordinate with superantigen-peptide conjugates in vivo or at repeated intervals of 1 to 4 days after tumor implantation or tumor appearance in the animal tumor models given in example 20. In patients with existing human cancer it may be given parenterally in doses of 1 $\mu$g to 500 mg at intervals of 1 to 4 days after parenteral administration of peptide-superantigen conjugates or after vaccination with peptide-superantigen conjugates in patients whose tumors have been removed.

1.Protocols for Prevention of T Cell Apoptosis after Stimulation with Superantigens and Peptides, Peptide-Superantigen Conjugates and Tumor Cell Transfectants Anti-apoptotic gene regulation of effector T cells will be performed before stimulation with peptide superantigens, peptide-superantigen conjugates or tumor cells transfected with superantigen, class I, class II, B-7 or $\alpha$-Gal genes. The addition of antisense oligonucleotides, intracellular antibodies, anti-apoptotic endonucleases, kinase and phosphorylation inhibitors as well as protease inhibitors to effector cells is carried out at appropriate intervals with respect to in vitro activation with superantigens, peptides and peptide-superantigen conjugates or tumor cell transfectants. The addition of cytokines or soluble Fas-Fc or Fas-IgG to the media may occur throughout the period of in vitro incubation of effector T cells with peptides, superantigens, peptide-superantigen conjugates or tumor cell transfectants.

E. In vitro T Cell Immunization with Superantigens and Cytokines with or without Antigen Presenting Cells Purified lymph node T cells ($4 \times 10^5$ cells/well) are cultured with SEB in the presence or absence of IL-1 (100 U/ml), IL-2 (1000 U/ml), IL-4 (1000 U/ml), IL-6 (1000 U/ml), IFN-$\gamma$ (1000 U/ml), IL-5 (1000 U/ml), TNF$\alpha$ (1000 U/ml), or syngeneic accessory cells ($8 \times 10^5$ cells/well). T cell Proliferation is quantitated after 48 hr by [$^3$H]TdR incorporation.

F. In vitro T Cell Immunization with Superantigens Immobilized on Solid Support

Silica beads (diameter 10 $\mu$m) carrying SCN-groups on a 17 spacer were the gift of Dr. K. Unger Institute of Anorganic Chemistry, University of Mainz. Proteins are covalently attached via amino groups in 50 mM borate buffer. pH 8.0.

Ten million derivatized silica particles are coupled with 50 $\mu$g ETA, SEB, or BMA030. After 48 h incubation at 4□ C. the remaining reactive groups are blocked by incubation with 0.1 M Tris/HCl pH 8.3. The beads are then washed extensively before they are added to the assay. $5 \times 10^4$ purified resting T cells are incubated in round bottom wells with $10^5$ silica beads coupled with the ligands indicated in the presence or absence of 25 U/ml rIL-2. Results are given as mean cpm $^3$H-TdR incorporation. Soluble ETA is used at 10 ng/ml.

G. Induction, Enrichment and Expansion of Tumor Specific TH-1 or Cytotoxic T Cell Clones for Tumor Therapy by Immunization with DNA or Heat Shock Protein Transfected Tumor Cells in vivo followed by Superantigen Activation of Sensitized T Cells in vitro Previous studies showed that presensitized tumor draining lymph node cells when further stimulated with superantigens in vitro produced tumor specific effector cells capable of secreting IFN$\gamma$ and killing tumor in vivo. These cells appeared to be the major effectors of the tumoricidal response. An additional modality for induction of TH-1 or cytotoxic T cells is to immunize the host intradermally or intramuscularly (a gene gun may be used) with a plasmid encoding DNA for a tumor peptide known to induce rejection. Examples of such peptides include the MAGE-1 and MART-1 peptides from human melanoma. Genes and cDNA from these and other tumor associated peptides have been isolated and they may be readily employed for host immunization. Heat shock protein conjugated to tumor associated peptide cDNA may be used to chaperone tumor associated DNA into tumor cells. These transfected tumor cells will readily express class I molecules as well as the transfected tumor peptides and activate cytotoxic T cells. Shortly after cDNA injection in vivo, regional lymph nodes or host immunocytes will be extracted or removed and placed in tissue culture. Pure T cell cultures obtained in this fashion will be enriched in TH-1 T cells. They will then be incubated with superantigens for up to 72 hours (with or without transforming growth factor) and then with IL-2 to further expand the TH-1 population. Heat shock protein-tumor antigen transfected tumor cells may be used in vivo as the initial immunization step followed by the superantigen-IL-2 stimulation steps in vitro as given above. The HSP-tumor antigen transfected tumor cells may be used for in vitro stimulation of T cells followed by superantigen-IL-2 expansion after in vivo cDNA immunization with a tumor associated plasmid. These treatments will result in an enriched and expanded TH-1 and/or a cytotoxic T cell population. Such expanded T cells will then be harvested and infused into tumor bearing hosts used for tumor immunotherapy as given in the protocols described in latter sections.

H. Immunization or Intratumoral Injection with Naked or Plasmid Superantigen or $\alpha$-Gal Superantigen-$\alpha$-Gal DNA or Superantigen-Tumor-Peptide or $\alpha$-Gal-Tumor-Peptide Naked or Plasmid DNA Superantigen or $\alpha$-Gal or superantigen-$\alpha$-Gal DNA in naked or plasmid form may be injected intramuscularly into tumor bearing hosts as a means of activating T cells and initiating an antitumor response. These agents may also be used as vaccines. Moreover, naked or plasmid superantigen or $\alpha$-Gal or superantigen-$\alpha$-Gal DNA may be injected directly into tumors to initiate tumor specific antitumor response and tumor regression. Naked or pDNA from a superantigen-tumor peptide fusion gene or $\alpha$-Gal-tumor peptide gene may be injected intramuscularly or inoculated directly into established tumors to initiate a tumor specific immune response and tumor regression. The DNA may be pre-processed ex vivo in muscle cells before selective delivery into host tumor tissue. Cationic liposomes may be used as carriers for these DNA constructs.

Injections of naked or pDNA may be made with a gene gun using a 1 ml syringe and a 28 gauge needle and administered intradermally or intramuscularly in a total volume of 100 $\mu$l. A tyne applicator may be used to deliver doses of 1–1000 $\mu$g of DNA at 3× weekly intervals. Tumor models and human protocols for assessment are given in Examples 19 and 20.

I. Dose Variations of Peptides and/or Superantigens to Produce Anergy or Sensitization of Effector T Cells for Autoimmune, Neoplastic or Infectious Disease The dose of peptide and superantigen will be adjusted in order to produce anergy or sensitization of T cells as might be desired for the particular peptide and disease. Peptides, in general, may be used in a broad dose spectrum to produce initial sensitization of a T cell clone. Each superantigen has its own dose spectrum in which it produces sensitization or anergy as desired in the T cell clone. In vitro sensitization with peptide or polymerized peptide alone may be the first step to create memory cells which may then be more effectively boosted with superantigen or superantigen-peptide conjugate.

In vivo immunizing schedules may involve the coadministration of peptides and superantigens parenterally in relatively low doses of each. The prior administration of the peptide as an adjuvant several days before parenteral administration of the superantigen may result in sensitization. Coadministration of antigen or peptide with superantigen will avert the development of anergy as will IL-1. In contrast, anergy may be produced by preimmunization with peptide in solution followed within 6–30 days by superantigen given parenterally. Coadministration of IL-10 in vivo may serve to maintain superantigen induced anergy.

J. Enhancement of Antitumor Effects of Peptide-Superantigen Activated T Cells by Interleukin 18 (IL-18)

IL-18 has now been shown to enhance IFNγ production by T lymphocytes in vivo. IFNγ is a major mediator of the antitumor effects produced by superantigenic activated T cells. Hence, IL-18 may be added to the media coordinate with superantigen and peptide or superantigen-peptide conjugate and/or added at 1 to 3 days after superantigens at the time of T cell harvesting and reinfusion. The IL-18 may also be given parenterally with T cells which are activated by superantigen and peptides or superantigen-peptide conjugates. The IL-18 may be given as a bolus or as a continuous infusion for 1–3 days after T cell infusion.

K Protocols for Anergy Induction

Anergy can be induced in vitro by direct TCR-mediated inactivation of certain functional responses in the absence of suppressor cells or inhibitor cytokines. Long lived anergy has been demonstrated in vivo after tolerogenic administration of superantigen or peptide. Anergy may be induced by TCR:CD3 engagement in the absence of costimulation that is normally provided by APCs. Costimulation allows activation of IL-2 production and is mediated by the interaction of CD28 on the T cell with B7 molecules on the APC.

a. Protocols for Anergy Induction in vivo

Acute parenteral injection of superantigen in doses of 0.001 nanogram to 1 mg will lead to cytotoxic anergy in T cell clones specific for that superantigen. Chronic exposure to superantigen parenterally with various doses of superantigen (0.001 ng to 1 mg) every other day for 3 to 30 days will also produce in vivo tolerance. Superantigens may also be administered in various adjuvants or vaccines to induce anergy using the dosage range of 0.001 ng to 1 mg. Anergy may be maintained by parenteral administration of IL-10. The optimal tolerizing or energizing dose will need to be determined for each host. In animals, maximum anergy with SEA is obtained with 1 to 10 nanograms.

b. Protocols for Anergy Induction in vitro

Anergy induction by superantigens in vitro may be produced by incubating superantigens with T cells in the absence of costimulatory signals or MHC class II molecules.

c. Functional Assays

Anergy is induced by incubation of T cells ($10^6$/ml) with peptides (up to 100 μg/ml) or SEB (up to 100 μg/ml) for 16 h at 37° C. Cells are thoroughly washed and then challenged with an immunogenic concentration of peptide or SEB in the presence of irradiated (6,000 rad) LNAT APC. Experiments with peptide are pulsed with 1 μCi of [$^3$H]thymidine (Amersham International, Amersham, Bucks, UK) for the last 16 h of a 72 h culture Proliferation is then measured by [$^3$H]thymidine incorporation for the last 8 h of culture.

d. In vitro Assays of Sensitization or Anergy

Proliferation Assays: Proliferation assays are performed using standard techniques. Briefly 40,000 purified CD4+ T cells/microtiter well are cultures in 96-well tissue culture clusters with flat bottom wells (Costar) for 3 d in culture medium (RPMI 1640 [Hazleton Biologics Inc., Lenexa, Kans.] supplemented with 20 mM glutamine [Hazleton Biologics, Inc.],. 10% heat inactivated FCS [Biofluids, Rockville, Md.] and 100 IU/ml of penicillin, 100 μg/ml streptomycin) under various conditions and pulsed (25 μl/well) with a [3H]thymidine solution (5 mCi/ml, 2 mCi/mmol specific activity; New England Nuclear, Boston, Mass.) during the last 8 h before being harvested on glass fiber filters. Incorporation of radioactive label is measured by liquid scintillation counting. Results are expressed as the arithmetic mean cpm of triplicate cultures. Due to the low precursor frequency of SEA-reactive CD4+ T cells, the cell number in the superantigen experiments is increased to 80,000/well, and cells from DR1-positive healthy donors are used to avoid any possible alloresponse. For studying ELAM-1-induced proliferation, we use 976-well Nunc-Immunoplate MaxiSorp F96 Flat-bottomed wells Nunc #4394564; (PGC Scientific, Gaithersburg, Md.) pretreated with ethanol for sterility, these plates allow optimal immobilization of ELAM-1 protein. Monocyte-independent CD4+ T cell proliferation is obtained by the combination of PMA (10 ng/ml) and PHA 1/200 dilution) (Gibco Laboratories).

The purified proteins DR1, ICAM-1, VCAM-1, and the CD3 mAb OKT3 are immobilized on the plastic well bottom, by dilution in PBS and overnight incubation at 4□ C., where after wells are washed with PBS.

e. Cytokine Analysis.

To obtain culture supernatant for cytokine analysis CD4+ T cells were cultured in culture medium (see above) ($10^6$/ml, final volume 2 ml) in 24-well flat bottom tissue culture plates (#3524; Costar). The proteins are preimmobilized in the wells as described for 96-well plates, but added in 10-fold higher amounts to adjust for the increased well-surface of 24-well plates. The culture supernatants are harvested after 24 h and 48 h of culture. Proliferation is measured in parallel cultures with 40,000 cell/well in 96-well plates as described before. IL-2 activity is defined in a bioassay using the CTLL-2 indicator cell line (American Type Culture Collection). IL-4 and GM-CSF levels are determined in ELISA assays (sensitivity of the assays are >24 pg/ml for IL-4 and >0.4 ng/ml for GM-CSF).

K. Assessment of Antigen Recognition by CTL $^{51}$Cr release cytotoxic assays and cytokine release assays will be performed to detect antitumor CTL reactivity. All assays will be performed by using CTL lines at 4 to 7 wk of culture. To analyze peptide recognition, T cell lines will be preincubated for 2 h at 37□ C. with 1 μg/ml peptide, washed, and used as target cells in a 51Cr release cytotoxic assay or as stimulators for cytokine release by CTL. Lytic units are calculated as the number of effectors/$10^6$ cells required to obtain 30% target lysis, with 5000 labeled target cells being used in the assay. GM-CSF, TNF-α, and IFN-γ levels will be determined by ELISA (R&D Systems, Minneapolis, Minn., for GM-CSF and TNF-α; and Endogen Inc., Cambridge, Mass., for IFN-g). CD4+ and CD8+ subpopulations will be obtained by positive selection with anti-CD4 and anti-CD8 Ab-coated culture flasks (Applied Immune Science, Inc., Santa Clara, Calif.). Melanoma lines (624-, 501-, and 397-mels) are established, 624-mel clones (624–38, HLA-A2+, and 624–28, HLA-A2-) are obtained by limiting dilution. Cultured melanocytes (NHEM530 and 680) are purchased from Clonetics (San Diego, Calif.). Melanoma lines A375 and HS695 and the breast cancer lines MCF7 and MDA231 will be obtained from American Tissue Culture Collection (Rockville, Md.). Uncultured melanomas will be obtained by enzymatic digestion of tumor lesions and used as cryopreserved samples. For cytotoxicity, target cells will be labeled with $^{51}$Cr and centrifuged on a Ficoll-Hypaque gradient to eliminate dead cells. Only samples with at least 60% viability and 70% tumor cells by morphologic analysis will be used as targets. Spontaneous release should never exceed 30% of the maximum $^{51}$Cr uptake. If Vβ clonality is observed in regional lymph node cells after sensitization or in TIL obtained before or after peptide stimulation these cells will be further stimulated with selected superantigen or superantigen mutants specific for the predominant Vβ phenotype.

Example 10

Preparation of Effector T Cells with Tumor Specificity: Reconstitution of Deleted T Cell Clones with Tumor Specificity and Production of Tumor Specific T Cell Hybridomas The T cell clones with tumor specificity developed and expanded with tumor peptides and superantigen and other immunogens as given previously will be immortalized by fusing these clones with human thymoma cells. The methodology for the establishment of these tumor specific T cell hybridomas is given below. In the course of life or tumor growth, T cells with selective Vβ phenotypes may be deleted or anergized. Hence, the host may be incapable of mounting an adequate immune response to a given tumor when it appears in situ. Moreover, the host immune response to tumor during progressive growth may also be attenuated due to the development of anergy or tolerance of tumor specific clones. Recent studies have suggested that wild mice are deleted of certain T cells with Vβ phenotypes during life probably as a result of intercurrent infections throughout life. Moreover, aging is associated with certain T cell deletions as well. This phenomenon provides a parallel in the mature life with the same process of tolerance induction to "self antigens" which occurs in fetal life. Recent studies have shown that the antitumor response of mice to a metastatic fibrosarcoma resides in a clone of T cells which is identified by a given Vβ phenotype. Deletion of this phenotype resulted in abrogation of the antitumor effect. Similar T cell anergy or deletion may also occur during life or in the course of tumor growth which may require reconstitution of the specifically deleted clone. The deleted clone may be replaced by transfecting uncommitted cells to include but not limited to hybridoma cells or embryonal totipotent stem cells with genes expressing the deleted Vβ phenotype. The genes may also be obtained from clonal T cells which are selectively expanded in peripheral blood or TIL after in vivo or in vitro immunization with tumor peptides and/or superantigens or tumor cells transfected with superantigens or α-Gal genes. Growth in tissue culture may be aided by the addition of IL-3, IL-6 or anti-CD3. Alternatively, growth may be specifically stimulated by the addition of a selected enterotoxin or mutant enterotoxin with specificity for the newly expressed Vβ in the embryonal T cell clone. The addition of a specific antigenic stimulus and/or IL-1 may be used as well and may also serve to prevent the development of anergy in the embryonal clone.

Hence, a tumor specific T cell clone or hybridoma is created comprising the deleted Vβ phenotype and having the property tumor specificity. This clone would be capable of stimulation by additional TAA or by superantigen or superantigen mutants specific for selected Vβ phenotypes. Methodology for creation of T cell hybridoma with tumor specificity expressing selected Vβ clonality is given below.

Propagation of the Embryonal Stem Cells

Execution of this protocol will serve to ensure the preservation of healthy undifferentiated ES cells. The classical method, for the maintenance of ES cells requires the preparation of STO feeder monolayers. An alternative is ESERO produced by the AMRAD Corporation Ltd. (Level 2, 17–27 Cotham Road, Kew, Victoria 3101, Australia. Tel: 61+3 853 0022. Fas: 61+3 853 0202) which is recombinant murine leukemia inhibitory factor (LIF). LIF is a simple, suitable alternative to STO monolayers and is highly efficient at inhibiting the spontaneous differentiation of ES cells in culture.

Materials
1. Medium: Dulbecco's modified Eagle's medium (DMEM high-glucose Irvine Scientific, cat. #9024)
2. L-glutamine (200 mM; 29.2 mg/ml; Irvine Scientific, cat. #9317). Add to DMEM for a final concentration of 2 mM.
3. Phosphate buffered saline (PBS), $Ca^{++}$-and $Mg^{++}$-free (Sigma, Cat. #D5527).
4. Trypsin-EDTA solution (0.5 g/L Trypsin, 0.2 g/L EDTA; Irvine Scientific, cat. #9341).
5. Serum: This is the most critical reagent in the propagation of stem cells. The feeder cells, STO (thioguanine-resistant, ouabain-resistant SIM mouse fibroblasts) require newborn calf serum (NCS: Gibco, cat. @ 200-6010AJ: Flow, cat. #29-121-54), and ES cells require fetal calf serum (FCS) (Hyclone cat. #A-1115-L).
6. Non-essential amino acids (NAA: 100X, Gibco, cat. @ 320-1140AG: 100X, Flow, cat. #16-810-49).
7. 2-mercaptoethanol (β-mercaptoethanol, BME; Sigma, cat. #M7522). This stock is at 14.4 M. Working stock is made fresh by adding 35 ml to 50.0 ml of PBS and sterilizing by filtration.
8. Gelatin: 0.2% (w/v) in water (Sigma, Swine skin, type I; Sigma, cat. #G 1890). Sterilize by autoclaving.
9. Mitomycin C: Dissolve 2 mg mitomycin C (Sigma, cat. #M0503) by adding 2 ml of sterile water or sterile PBS to the injection vial. The drug should be stored in the dark at 4☐ C. and used for no more than one week. This is a 100X stock. Penicillin/streptomycin (PEN/STREP) (100X; Irvine Scientific, cat. #9366)

| Media Formulations | |
| --- | --- |
| DMEM + 10% NCS STO feeder cells | DMEM + 15% FCS ES cells |
| 450 ml DMEM | 425 ml DMEM |
| 50 ml NCS | 75 ml FCS |
| 5 ml L-glutamine | 5 ml L-glutamine |
| 5 ml PEN/STREP | 5 ml PEN/STREP |
| | 5 ml NAA |
| | 5 ml BME working solution (10 mm) |

Method

STO fibroblasts (Ware and Axelrad, 1972) that have been mitotically inactivated by treatment with mitomycin C are used as feeder cells for ES cells. Feeder layer is made from STO cultures that retain their ability to be contact-inhibited; thus any culture that reaches a cell density greater than $8 \times 10^6$/100-mm dish should be discarded and replaced with cells that were frozen earlier.
1. When STO cells reach confluence (6–$8 \times 10^6$ cells/100-mm dish), aspirate the media, and wash the monolayer once with 5 ml of PBS.
2. Add 1.0 ml of trypsin-EDTA to the monolayer and incubate at 37☐ C. for about 5 minutes.
3. Inactivate the trypsin by adding 9.0 ml DMEM, 10% NCS to the monolayer. Repeatedly pipette forcibly to produce a single-cell suspension.
4. Seed 1.0 ml of the cell suspension per 100-mm dish with 10.0 ml media. Incubate at 37☐ C. from 4–5 days until cells reach confluence and passage again.

Preparation of Feeder Cell Layers
1. Treat freshly confluent 100-mm dishes of STO cells with inactivation media (10.0 ml of DMEM, 10% NCS, supplemented with mitomycin C to a final concentration of 10.0 mg/ml) for 2 hours at 37☐ C. Use a mitomycin C stock that is less than one week old and prepare the inactivation media fresh.
2. While the STO cells are being treated, incubate the appropriate number of new 60-mm petri dishes with enough sterile 0.1% gelatin to cover the bottoms of the dishes, and incubate for one hour at room temperature. Aspirate the gelatin solution.
3. Aspirate the mitomycin-C-supplemented media and wash the monolayers three times with 5–10 ml of PBS.
4. Incubate the monolayers with 1.0 ml of trypsin for 5 minutes at 37☐ C.
5. Suspend the trypsinized cells in 14 ml of media and centrifuge at 250×g for 5 minutes. Aspirate the media, resuspend the cells in 10 ml of media, and count in a hemocytometer.

6. Seed 9×10⁵ cells in 60-mm dish that has been gelatin-treated. The final volume of the dish should be 4.0 ml.
7. Incubate the feeder plates at 37□ C. If the monolayer is not confluent the next day, more mitomycin-C-treated cells can be added.
8. These feeder layers are useful for about 7–10 days.

A. Propagation of Embryonal Stem Cells. ES cells should be passaged every 3–4 days on feeder layers. Once an ES line has been established, many frozen vials should be generated to ensure that low-passage-number cultures can be used for experimentation. ES cell cultures should be split just as they reach confluence, and they are fed with fresh media a few hours before subculture.

1. Thawing of Frozen ES Cells
   1. Remove an ampule of ES cells from the freezer and thaw at 37□ C. until ice crystals disappear.
   2. Sterilize the outside of the tube with ethanol.
   3. Pipette the contents of the ampule into a 15-ml centrifuge tube and add 5 ml of fresh complete media with constant, gentle agitation.
   4. Pellet the cells at 250×g.
   5. Aspirate off the media, resuspend the pellet in fresh media, and add the ES cells to an STO monolayer.
   6. One day after plating, remove media and replace with fresh media. If the thawing procedure has been carried out properly, expect approximately 90 percent viability.

2. Continuous Culture of ES Cells
   1. Aspirate off the media, and rinse the ES/STO culture with 5.0 ml PBS.
   2. Add 0.5 ml of trypsin to the 60-mm culture dish and incubate at 37□ C. for 4–5 minutes.
   3. Add 1.0 ml of DMEM, 15% FCS, and repeatedly pipette the cells with a cotton-plugged 9.0 inch sterile Pasteur pipette until the cell suspension is free of clumps.
   4. Resuspend the cells in a total volume of 15 ml of complete media and centrifuge for 5 minutes at 1,000 rpm.
   5. Aspirate the media, resuspend the cells in 10 ml of complete media and count. A typical 60-mm dish will contain about 2×10⁷ ES cells and 9×10⁵ STO cells. Therefore, the contribution of the STO cells to the total cell suspension is negligible.
   6. Seed 1.0×10⁶ cells in 4 ml of complete media into a 60-mm dish with an STO feeder layer. Incubate.
   7. Subculture again in 3–4 days.

Methods of Harvesting and Culturing Totipotent Stem Cells for Transfection of TCR Vβ Genes and Genes with Tumor Specificity, Immunization with Tumor Specific Antigens, Production of T Cell Hybridoma and T Cell Clones for Reconstitution of Tumor Specific Immunity Human fetal BM from 14–24 week gestation fetuses is obtained from Advanced Bioscience Resources, Inc. (Alameda, Calif.). Single-cell suspensions of fetal BM are prepared by flushing the BM cells out of the humeri and femurs using a syringe and a 22-gauge needle into phosphate-buffered saline (PBS) containing 1% wt/vol bovine serum albumin (BSA). The low-density mononuclear cell fraction of BM is obtained by centrifuging the cell suspension over a Ficoll step gradient (density, 1.077 g/mL) and collecting the buoyant cell fraction. The yield of mononuclear cells from each fetal sample ranges from 1×10⁶ to 100×10⁶ cells from two femurs. For cell sorting, cell suspensions are stained with saturating concentrations of the following monoclonal antibodies (mAbs): (1) CD34-allophycocyanine (APC), CD38-phycoerythrin (PE), and HLA-DR-fluorescein isothiocyanate (FITC); (2) CD34-APC, CD38-PE plus HLA-DR-PE, and CD50-FITC, or (3) CD34-APC, CD38-PE, and HLA-DR-FITC plus CD50-FTC. Single cells are sorted into the individual well of a 96-well tissue culture plate containing cell culture media using a FACS Vantage cell sorter (Becton Dickinson Immunocytometry Systems, San Jose, Calif.) equipped with an automatic cell deposition unit (ACDU), a Coherent Enterprise laser tuned at 488 nm (100 mW), and a Coherent Spectrum laser tuned at 647 nm (100 mW). For cell analysis, 1×10⁶ cells were stained first with CD3, CD10, CD19, CD13, CD 14, CD15, CD36 (GPIIIb), CD43, CD49b, CD49d, CD49e, CD50 (intercellular adhesion molecule-3 [ICAM-3], CD54 (ICAM-1), CD62E (E-selectin), CD90w (Thy-1), CD105 (Endoglin), or CD106 (vascular cell adhesion molecule-1 (VCAM-1)), followed by a washing step and staining with preconjugated goat-antimouse Ig antisera (Jackson Research Laboratories, West Grove, Pa.). After a wash step, normal mouse serum was added for 10 minutes, followed by staining with CD34 perdinin chlorophyll protein, CD38-APC, and HLA-DR-FITC. Cell analysis is performed on a modified FACScan. The flow cytometer is equipped with a 12-mW argon ion laser (488 nm), a 30-mW YAG laser (532 nm), and a 10-mW HeNe laser (633 nm). PE was excited with the YAG laser, which results in a six-fold increase in sensitivity as compared with excitation at 488 nm. Data analysis is performed with the Paint-A-GatePLUS software program (BDIS).

1. Tissue culture. Tissue culture media consists of the Terry Fox long-term myeloid media (TF) supplemented with one of three combinations of growth factors: medium 1: 10 ng/mL insulin growth factor-1 (IGF-1) and 2.5 ng/mL basic fibroblast growth factor (βFGF); medium 2: a mixture of hematopoietic growth factors consisting of 10 ng/mL interleukin (IL)-3, 500 U/mL IL-6, 10 ng/mL granulocyte-macrophage colony stimulating factor (GM-CSF), 2.5 U/mL erythropoietin (EPO: AMGEN, Thousand Oaks, Calif.). 50 ng/mL stem cell factor (SCF: Genzyme, Cambridge, Mass.), plus 10 ng/mL IGF-1 and 2.5 ng/mL βFGF: or medium 3: TF supplemented with different combinations of IGF-1, βFGF, 10 ng/mL platelet-derived growth factor (PDGF), and 10 ng/mL epidermal growth factor (EGF). Growth factors are obtained from Collaborative Research (Bedford, Mass.). In unfractionated BM, stromal cell growth is determined in serum-free medium supplemented with IGF-1 or bFGF (GIBCO 15A and GIBCO 16A; provided by GIBCO). Tissue culture plates are kept at 37□ C. in a 5% vol/vol CO₂ humidified atmosphere. Single cells with CD34+, CD39−, HLA-DR−, CD34+, DC38−, HLA-DR+, and CD34+, CD38−, CD50−, HLA-DR− phenotypes are deposited into individual well of a 96-well tissue culture plate.

Each well contains either 200 mL of cell culture media containing TF+βFGF+IGF-1 (medium 1), or the same media supplemented with the mixture of hematopoietic growth factors described above (IL-3, IL-6, EPO, GM-CSF, and SF; medium 2). The growth of the sorted cell in each well is determined by visual inspection after 3,7,14,and 21 days of culture. Wells are scored as positive when they contained more than 50 cells after 14 to 21 days of culture. The culture media of established cultures of hematopoietic and stromal cells are refreshed every 2 weeks by removing half of the culture media and replacing it with fresh media. Stromal cell cultures are replated by mechanically disaggregating the adherent cell monolayer on the more complex structures and replating the dispersed cells into new tissue culture wells containing fresh media every 2–3 weeks. Nonadherent cells are removed from the stromal cell layers or stromal cell structures using a micropipette and an inverted microscope.

2. Immunophenotyping of cultured cells. Cytospins are prepared from the nonadherent cell populations derived from cultured single cells. Single-cell suspensions obtained from the cultured cells are centrifuged at 1,000 rpm for 5 minutes and then resuspended in PBS plus BSA at a concentration of $2 \times 10^4$ cells/ml, and $5 \times 10^4$ cells are deposited onto a glass slide by centrifugation in a Shannon II cytocentrifuge (Shannon Inc, Pittsburgh, Pa.). The cells are allowed to dry in air and then stained with Wright-Giemsa or fixed by a brief immersion in acetone. Fixed slides are then immunophenotyped using a biotin-streptavidin technique. In brief, slides are sequentially incubated with 3% vol/vol $H_2O_2$ in PBS, incubated with an unlabeled mouse primary antibody, incubated with a diluted biotin-goat antimouse sera, and incubated with the appropriate dilution of streptavidin-conjugated horseradish peroxidase (Jackson Research Laboratories). Each incubation is followed by washing the slides in PBS. The presence of bound primary antibody is shown by developing the peroxidase reaction with 3% diaminobenzidine, and then the slides were lightly counterstained with methylene blue. The primary antibodies used for this study were CD45RB, CD49b, CD10, CD13, CD3, CD43, and CD50.

3. FACS analysis of cultured cells. Nonadherent round cells that developed from cultured stromal cells are analyzed on the experimental flow cytometer described above. Cell suspensions containing $0.5 \times 10^6$ to $1 \times 10^6$ cells in 100 mL PBS plus BSA are incubated with 20 mL of each diluted mAb that had been directly conjugated to a fluorochrome. The following antibodies are used: CD11c-APC, CD13-PE, CD14-FITC, CD19-PE, CD34-APC, CD43-PE, CD45-FITC, CD49b-APC, HLA-DR-PerCP, CD50-FITC, and CD68-APC. Scatter gates are set to exclude debris with very low forward scatter or very high side scatter, and 30,000 gated events are collected for each sample.

Preparation of T Cell Hybridomas

1. Parent T Cell Tumor Lines for Fusions. Four related parental T cell tumor lines are used. The first two are derived from the Con A-inducible T cell hybridoma, FS6-14.13. FS6-14.13 cells are grown in $10^{-4}$ M AG. Most of the hybrid cells die within the next few days, but over a period of weeks the cultures are overgrown by surviving cells resistant to the drug. These cells are cloned at limiting dilution and the resultant clones are tested both for sensitivity to HAT and for IL-2 production after Con A stimulation. One clone, FS6-14.13.AG2, is selected for use in fusions. In one case, a subclone of FS6-14.13.AG2, which was selected for resistance to both AzaG and $10^{-3}$ M Oua, is used as the tumor parent. This subclone is called FS6-14.13.AG2.OU8 Parental Antigen Specific T Cells for Fusions. A population of normal T cell blasts highly enriched in antigen-specific cells is prepared by the method of Schrier et al. Briefly, lymph node cells are taken from humans and cultured at $4 \times 10^8$/ml for 4 d with specific antigen (125 $\mu$g/ml MART-1 or other tumor specific antigens, 10 $\mu$g/ml KLH, or 50 $\mu$g/ml apo cyto c 1–65 peptide). These cultures contain a high concentration of T cell blasts. Viable cells are isolated on Ficoll-Hypaque gradients and are recultured for 3–4 d at an initial concentration of $10^6$ cells/ml in medium containing 50% IL-2 SN. The viable T cell blasts are then reisolated and used in fusions. Previous experiments showed that this procedure resulted in a T cell preparation 100-fold enriched over the initial lymph node cells in specific T cell helper activity or proliferative ability.

2. Fusion Protocol. Cells are fused essentially by the method of Kontiainen et al. Both PEG-1540 and PEG-6000 are used. In these experiments, $4 \times 10^7$ T cell blasts are fused to $1-2 \times 10^7$ FS6-14.13.AG2 or FS6-14.13.AG2.OU8, cells. Cells are plated in –300–400 microculture well 0.1 ml of medium. HAT is added at 24 h and the medium is changed about every 5 d. Hybrid growth is first apparent at about 10 d and the last wells are scored positive for growth at about 3 wk. Hybrids are transferred to larger vessels to obtain enough cells for testing and are eventually "weaned" off HAT in HT-containing medium.

3. Cloning of Hybrid Cells. Hybridomas are cloned at limiting dilution of four 96-well microculture plates containing, on the average, 0.125, 0.25, 0.5, and 1.0 cells/well. When possible, functional clones are selected from the plate having the fewest clones. At no time are clones selected from a plate containing more than 20 clones (2.4% chance of more than one clone/well).

4. Additional T Cell Clones and Hybridomas. T Cell lines such as the TRT3T3.5 (a Jurkat cell mutant) which is CD3 TCR negative and MHC class II negative may be used for transfection with V$\beta$ genes and subsequent stimulation with peptide and superantigens. T cell hybridomas may be prepared from such cells and used for V$\beta$ gene transfection and as targets for stimulation by peptides and superantigens. Various TH-1 and TH-2 clones which bear specific V$\beta$ receptors are well known and T cell hybridomas bearing specific V$\beta$ receptors have been established. Hybridomas which bear V$\beta$ 8 alleles include the BDK 23.1 and the 22.D11. Both the uncommitted T cell clones, receptor negative T cell clones and hybridomas may be used for transfection with V$\beta$ genes and stimulation with peptides and superantigens. Receptor negative T cell lines may be stimulated with peptide and superantigen before or after conversion to hybridomas.

5. Cloning of TCR $\alpha$ and $\beta$ Chain cDNA. T cell clones are purified free of APC and stimulated for 6 h with 1 $\mu$g/ml phytohemagglutinin-P (Sigma Chemical Co.) and 10 ng/ml PMA (Sigma Chemical Co.) to increase TCR $\alpha$ and $\beta$ chain mRNA expression (19). RNA is purified from $5 \times 10^6$ cells by the guanidine isothiocyanate-acid phenol method. cDNA is synthesized by a standard oligo-dT primed method. cDNAs encoding the HA1.7 TCR $\alpha$ and $\beta$ chains are then amplified using the anchored PCR (AnPCR) as modified by Dr. P. Marche and Dr. O. Acuto (Institut Pasteur, Paris, France). For amplification of TCR $\alpha$ chain cDNA, an antisense primer is designed to include part of the C region, (bold type), and EcoRI, and BglII sites: 5'-GCGAATTCAGATCTTAGGCAGACAGACTTGT CACTGG-3' (SEQ ID NO:69); the sense primer for the TCR $\alpha$ chain contains a dC anchor, XhoI, NotI, and SalI sites: 5'-CACTC-GAGCGGCCGCGTCGACCCCCCCCCC-3' (SEQ ID NO:70). The antisense primer used to amplify the TCR $\beta$ chain contains part of the C region (bold type), KpnI, SalI, and ClaI sites: 5'-GGTACCGTCGACATCGATCCACCAGCTCAGCT CCACGTGGTCG-3' (SEQ ID NO:71). The sense primer for the TCR $\beta$ chain includes a dC anchor, SphI, NotI, and SacII sites: 5'-GCATGCGCGCGGCCGCGGAGGCCCCCCCCCC CCCC-3' (SEQ ID NO:72). 25 cycles of AnPCR were performed, each cycle consisting of 1 min at 94☐ C., 2 min at 55☐ C., 3 min at 72☐ C., and a single final extension of 6 min at 72☐. AnPCR products are isolated, cloned, and sequenced by standard methods. Full $\alpha$ and $\beta$ coding sequences are constructed using constant region cDNAs derived from the Jurkat TCR $\alpha$ and $\beta$ chains.

6. Tumor Specific T Cells for Use in Preparing Tumor Specific T Cell Hybridomas The tumor antigen specific T cell population is derived from peptide and superantigen stimulated T cells or T cells stimulated with superantigen-tumor peptide conjugates or tumor cells transfected with superantigen and/or α-Gal genes as outlined in examples given herein. T cells sensitized to tumor in vivo and further stimulated in vitro with superantigen alone may also be used. Uncommitted stem cells transfected with naked DNA or plasmid DNA from superantigen stimulated tumor specific effector cells may also be used to create T cell hybridomas. The methods of fusion of the tumor antigen specific T cells with the T cell tumor lines to produce stable and high producing T cell hybridomas for therapeutic infusion are well described in the art. It should be noted that superantigen stimulated specific T effector cells may contain Vβ overexpression clones and that tumor specific cDNA from these cells may contain gene sequences expressing this Vβ bias together with other components of the T cell receptor variable region gene family. The Vβ DNA containing the genes for tumor specificity may be used for transfection into embryonic stem cells to create tumor specific T cell hybridomas as given above. A fusion gene consisting of tumor specific DNA and Vβ DNA with or without other variable region nucleotides from superantigen stimulated tumor specific effector T cells may also be prepared which may be used for preparation of tumor specific T cell hybridomas or for transfection into embryonic stem cells.

The basic method for generation of T cell hybridomas involves immortalizing T cells by fusing them with a pre-existing cell line (the fusion partner) to form a T cell hybridoma. Fusion-partner cells (a pre-existing cell line appropriate for the studies to be done) are mixed with activated T cells to be immortalized and the cell mixture is then exposed to polyethylene glycol (PEG) to bring about fusion. The fusion is stopped by addition of medium and the cells are cultured prior to selection. T cells immortalized should be maximally activated and proliferating to ensure better fusion efficiency. Hybridoma selection may utilize fusion-partner T cells that have a normal complement of DNA- salvage-pathway enzymes (HGPRT) in which selection is made either on the basis of a selectable surface marker or because the fusion partner has been depleted of ribosomes by emetine and actinomycin D. The second involves fusion partner T cells that are deficient in DNA-salvage-pathway enzyme (HGPRT) and are selected in HAT medium (which kills unfused HGPRT-deficient cells). HAT selection can be used in conjunction with ouabain selection to ensure non-survival of unfused normal T cells.

Receptor Transfection: Transfection of Deleted Vβ Chain Gene into Embryonal T Cells, T Cell Hybridoma or Uncommitted T cells A. Transfection Procedures 1. The truncated β-chain construct is transfected into the mouse thymoma EL4 which is used as the T cell recipient. However, various hybridomas or uncommitted T cell clones (receptor negative) may be used as well. The subline of EL4 used expresses CD3 and TCR on one cell surface, as shown by staining with 2C11 (anti-CD3e), 500A.2 (antiCD3e), and H57-597 (anti-αβ TCR). The mouse myeloma J5581 is used as the B cell recipient. However, various T hybridomas uncommitted T cell clones (receptor negative) may be used as well. This line is a heavy chain loss mutant of J558 that makes and secretes α 1-chain. Cells are transfected by electroporation and selected for expression of the neomycin-resistance gene with G418 (Geneticin, GIBCO) (0.5 mg/ml of active drug). Resistant cells are screened initially for expressions of the β-chain by Northern analysis. Positive genes are then tested by immunoprecipitation. We utilize a line from a single colony of the T or B cell transfectants.

2. The transfection system is one in which the products of human Vβ genes are introduced into human TCR expressed on the surface of a human T cell hybridoma. The specificity of this receptor is then be determined by the ability of the transfectants to produce interleukin-2 (IL-2) when stimulated with various toxins presented by cells bearing class II MHC molecules. Initially, transfectants are produced with receptors bearing either human (h) Vβ13.1 or Vβ13.2. Representative clones with good TCR surface expression are tested for reactivity to toxins presented either by class II+ B-cell lymphoma, or by splenic class II+ non-T cells of various HLA haplotypes. Immobilized anti-Vβ antibody (that is, an antibody to the TCR β-chain constant residues) is used as a positive control to measure maximal TCR-mediated stimulation.

Production of T Cell Clones with Selected Vβ Phenotypes: Transfection of Specific Vβ-Chain Genes into Uncommitted Embryonal T Cells or Hybridoma A. Preparation of Truncated β-chain Gene for Transfection (Gascoigne, N. R. *J Biol. Chemistry* 256:9296, 1990)

Truncation of the β-chain Gene—To accomplish this, the codons for the first 2 amino acids of the $C\beta_2$ exon plus a serine residue and chain termination codon are added to the end of the $C\beta_1$ exon, as follows. The $C\beta_1$ exon [derived from the 3'-most Cβgene] encoding the external globular domain of Cβ is subcloned as an EcoR1 to Sac1 fragment in pGEM3. RNA is made from this template using the Sp6 RNA polymerase promoter. To perform the mutation, an oligonucleotide primer 5'-GGATCCGGATCCTATGAACAGTCTGCTCGGCC CCAGGCCTCTGC-3' (SEQ ID NO:73) is used. This has a region of complementarity of 22 nucleotides with the RNA but with extra sequences present to delete the $C\beta_1$-$C\beta_2$ splice signal and to add the $C\beta_2$-encoded amino acids Asp-Cys followed by Ser-Stop and two BamHI recognition sequences. A first strand cDNA is made with this primer using avian myeloblastosis virus reverse transcriptase. The second strand cDNA is made using a primer specific for the 22-nucleotide region immediately 5' of the BglII site 496 base pairs upstream from the start of $C\beta_2$ using the Klenow fragment of DNA polymerase I. The resulting double stranded cDNA is cut to completion with BamHI plus BglII, gel purified, and cloned into pGEM3 cut with BglII plus BamHI. This construct is sequenced to ensure that only the predicted mutation is obtained. A plasmid containing the immunoglobulin heavy chain enhancer ($E_H$), the promoter, and signal peptide exon from the MPC-11 k-chain gene, and the rearranged VDJβ exon from the T cell 2B4 (Vβ2B4) in the 5.7-kilobase EcoRI to BamHI fragment of pHβAPr-1-neo is prepared. This fragment of the vector contains a neomycin resistance gene and the 3'-untransfected region and poly(A) addition site from SV40. Vβ2B4 consists of $V\beta_3,D\beta_2$ and $J\beta_{2.5}$. 2B4 is a well characterized T cell hybridoma that recognizes a pigeon cytochrome c peptide with I-$E^k$. The mutated Cβ exon is cloned as a BglII to BanmHI fragment into the BamHI site of this plasmid, resulting in a gene consisting of Lκ, Vβ, and mutated coding sequences. This construct permits replacement of the Vβ exon at the SalI site. For example, Vβ2B4 is excised with SalI and replaced with the VβD10 exon. D10 is a cloned T helper cell responsive to conalbumin plus 1Ak. The V region exon consists of $V\beta_{B2}$, $D\beta_2$, and $J\beta_{2.1}$ and was kindly provided by Drs. J. Kaye and S. Hedrick. A region from of EcoRI site between the leader and V region exon to the KpnI site downstream of Jβ2.2 is subcloned twice into pUC19 so as to flank it with SalI sites.

B. Cloning of T Cell Receptor DNA for Transfection

The Vγ9 chains from T cell clones, 9A and IX, are cloned by RT-PCR using primers that spanned the entire molecule Vγ9LA-oligo, GAGCTCGAGGTCTAACGCTTCTC (SEQ ID NO:74), and Cγ4-oligo, GCGATCGATCGAGATCT-TATTACGGAAAAACACAC (SEQ ID NO:75). The products are digested with SacII and XhoI cloned into Bluescript and sequenced. The γ-chain from hybridoma Hy11 is amplified and cloned in a similar way with a different V region primer, Vγ3L-oligo, GAGCTCGAGGATCTTCTGCTC-CTC (SEQ ID NO:76). The chains are subcloned into the pHβApr-1 vector without any selection marker or into pREP4a (a gift of Dr. Mark Tykocinski, Case Western Reserve University, Cleveland, Ohio) expressing hygromycin resistance. The δ-chains are cloned by RT-PCR of RNA from the γδ T cells. The Vδ regions are amplified with primers that begin 5' of the AUG translational start signal, Vδ1Lx-oligo: TACTCGAGCTGCCCCTGAGTGAGC-CATGCTGTTCTCCAGCCTGC (SEQ ID NO:77), or vδ2L TACTCGAGCTGCCCCTGAGTGAGCCATGC (SEQ ID NO:78), and a C region primer Cδ3-oligo GAGATGA-CAATAGCAGGATCAAACTC (SEQ ID NO:79). After RT-PCR, the product is digested with the restriction enzymes XhoI and EcoRI then cloned into Bluescript (Stratagene, San Diego, Calif.) and sequenced. This fragment is combined with previously characterized EcoRI-BamHI C region fragment (19;and E. Loh, unpublished data) that retains the first C region intron, contains the entire 3' untranslated region to the second polyadenylation site, and includes a poly (A) stretch, approximately 70 bp long from the original cDNA. This δ-chain is cloned into the multiple cloning site in the β-actin vector, pHβApr-1-neo, which allows selection with the antibiotic, G418. A second vector, pREP9, also expressing neo resistance is used for the expression of β-chain in some experiments. While the above methods is given for cloning Vγ chains from T cell clones, similar methodology is well known in the art for cloning other components of the T cell receptor from T cell clones to include Vβ, Vα and CDR structures.

C. Transfection and Selection of Positive Clones

The electroporation is performed with a Bio-Rad Gene-Pulser using 250 V/0.4 cm and 960 mF. The two expression plasmids are linearized with PvuI and were cotransfected using 10 mg of the δ construct and 100 mg of the γ construct DNA. Two days after electroporation the cells are transferred to medium containing 1.0 mg/ml of G418 (GIBCO BRL, Grand Island, N.Y.). The successful transfectants obtained after approximately 3 wk of selection are analyzed for expression of the TCR/CD3 complex by OKT3, TCR-d1, dTCs, BB3 and TigA mAbs. The Vγ9/Vd1 transfectants with the γ and δ gene segments under Rous sarcoma virus (RVS) promoter (pREP) contained less than 20% TCR/CD3+ cells, whereas those with cDNA segments expressed under β-actin promoter (pHb-Apr-1-neo) had on average 30% positive cells. Cultures are enriched for TCR expression by sorting for OKT3 or TCR-d1 reactive transfectants on Epics Elite flow cytometer followed by cloning by limiting dilution and selection of transfectants for a high level of TCR/CD3 expression. Transfectants that survived the antibiotic selection but did not express the cell surface TCR-γδ are chosen as negative controls for some of the experiments.

Construction of plasmid pTBF-neo: The cDNA fragment specific for the β-chain is subcloned into vector pFP502EB511, downstream from the SFFV-LTR, to create plasmid YT35. pTBF-neo is constructed and then transfected into *Escherichia Coli* strain DH1. The bacteria are cultured, converted into protoplasts and fused to J.RT3-T3.5. Cells are plated at a concentration of $10^5$ cells per ml in 24-well culture plates and incubated for 48 h. Geneticin is added (2mg/ml$^{-1}$) to select for transfected clones.

Cloning of Vβ cDNA from T cell Lines

The β-chain cDNA is cloned by PCR according to the manufacturer's instructions (Perkin Elmer Corp., Norwalk, Conn.) from a T cell clone containing the appropriate sequence using the appropriate primers. The β-chain cDNA was isolated by reverse transcriptase reaction using Rnase H-reverse transcriptase (Bethesda Research Laboratories, Gaithersburg, Md.) followed by PCR using RNA derived from T cells as a template and primers from the T195 genomic sequence and the primer from the published sequence of β-chain. Both of these PCR constructs were subsequently digested at the BamHI sites designed into the PCR primers. For the second transfectant, the β-chain cDNA is ligated into the BamHI site in the polylinker of the vector pHβ-Apr-1-neo (25) downstream of the promoter and first intron of the human β-actin gene and upstream of the polyadenylation signal. For a third transfectant, the analogous vector pHβ-Apr-1-gpt is used for the TCR β-chain construct.

Transfection and Selection of Positive Clones

The vectors are linearized with PvuI and transfected by electroporation into $10^7$ recipient cells per cuvette using a Bio-Rad Gene Pulser (Bio-Rad Laboratories, McLean, Va.) apparatus with phosphate buffered sucrose (272 mM sucrose, 1 mM MgCl$_2$, 7 mM potassium phosphate, pH=7.4) at 25 μfd and 350–420 V. After electroporation, the cells are plated at $10^5$ cells/well in 96-well plates and selected with Geneticin G418 (GIBCO, Grand Island, N.Y.) after 2 to 4 days. For selection of T cells, G418 is used at 0.05–1 mg/ml (effective concentration). After selection and screening, the transfectants are maintained in G418 at 2.0 mg/ml. Positive colonies are screened by flow cytometry using the appropriate mAb.

Immunization and Transfection of Embryonal T Cells for Expression of Deleted Vβ chains with Tumor Specificity and Immortalization as T Cell Hybridomas The same embryonal T cells and thymoma cells transfected above with the deleted Vβ chain gene will be transfected with DNA or genes from T cell clones showing tumor specificity or T cell clones representing tumor specific effector cells following superantigen stimulation. The T cells will be expanded and ultimately immortalized as T cell hybridomas. Alternatively the embryonal T cells will be immunized with the MART-1 antigen nonapeptide or other tumor antigens in vitro using in vitro methods described by Rosenberg et al (1995). Class 1 positive cells e.g. HLA-A1+ cells will be needed for attachment of the nonapeptide in order to confer appropriate immunogenicity to the peptide. The appropriate superantigen will be used to further augment the tumor antigen specific T cell response in tissue culture and to induce expression of the appropriate Vβ phenotype in the embryonal or thymoma population. Alternatively, the genes for appropriate cytokine induction in particular interferon γ will be transfected and linked to activation in TH1 cells by appropriate Vβ surface triggering by superantigen. Similarly, the tumor specific and cytotoxic genetic material from immune cells will also be transfected into the embryonal T cells or uncommitted thymoma.

Example 11

Procedures for Analysis of Tumor Draining Lymph Node Cells, PBL and Tumor Infiltrating Lymphocytes (TIL) and Eluted T Cells from Immobilized Antibody Columns, Receptor Transfected Stem Cells and Hybridomas for Vβ Gene Expression A. Phenotypic Analysis of Cultured Cells. Two-color direct immunofluorescence analysis will be performed using a FACScan flow cytometer (Becton-Dickinson Immunocytometry Systems, Mountain View, Calif.) interfaced to a Hewlett Packard Model 310 computer, and data analysis will be performed using logarithmic amplification on 10,000 viable cells as determined by forward and right angle scatter patterns. All of the antibodies used in this study will be purchased from Becton-Dickinson and included CD3 (leu-4), CD4 (Leu-3a), CD8 (Leu-2a), CD56 (Leu-19). CD25 (IL-2 receptor), and HLA-DR. Each sample analyzed will contain 1–6 cells. Cells will be stained after centrifugation, resuspended in 15 ml of appropriate antibody, and incubated on ice for 45 min. The sample will then be washed with 3 ml of phosphate-buffered saline containing 0.2% fetal bovine serum (GIBCO) and 0.1% sodium azide, centrifuged, and fixed in 1.0 ml of 1% paraformaldehyde, Analysis of cells will be performed within 3 days after fixation.

B. Cytotoxicity Assay. The 4-h $^{51}$Cr release assay will be used to determine the cytotoxic reactivity of IVS-LN and IVS-PBL cells. Tumor targets utilized will be cryopreserved fresh tumor cells which were thawed and washed for labeling. Tumor cells ($10^7$) will be labeled with $^{51}$Cr (Na$^{51}$Cr) 4100 mCi: New England Nuclear, Boston, Mass.) at 37□ C. for 1 h and washed 3 times in CM. Target cells will be incubated with various numbers of effector cells at 37□ C. in a volume of 0.2 ml of CM for 4 h. The supernatant will be collected (Titertek Collecting System: Flow Laboratories, McLean, Va.), and the samples will be counted in a gamma counter. The calculation is as follows:

$$\% \text{ of lysis} = \frac{\text{experimental cpm} - \text{spontaneous cpm}}{\text{maximal cpm} - \text{spontaneous cpm}} \times 100$$

A lytic unit is defined as the number of effector cells needed to mediate 20% lysis of $10^4$ target cells. The number of lytic units per $10^7$ effector cells is then calculated for each tumor target.

C. PCR and Quantitation of Vβ Gene Expression. In order to quantify Vβ gene expression, a method described previously by Choi et al (Yasumura, S., et al., Cancer Res., 53, 1461, (1993)) is used. The 22 Vβ primers specific for 20 TCR-Vβ families as well a 1 C primer for Vβ amplification and 3' and 5' Ca primers are used as standards for quantitation. The primers are synthesized according to sequences previously described. For the PCR reaction, a solution consisting of 1.3 mM MgSO4, 50 mM KCl, 10 mM Tris-HCl, 0.2 mM concentrations each of deoxynucleotide triphosphate, 0.4 mm concentrations of the Ca and the Cβ primers, about 10 cpm of 5'-32 P-end labeled 3' Ca and 3' Cβ primers pet tube, cDNA from 2 mg of total RNA, and 2.5 units of ampimpliTaq polymerase (Perkins-Elmer-Cetus)/ amplification tube are added into each of 22 tubes containing 20 pmol of one of the Vβ primers. The final volume is 50 ml/tube. To exclude contamination reagent controls are performed. The amplification schedule was the following: 30s melting at 95° C., 25s annealing at 55° C. and 45s extending at 72° C. No more than 30 PCR performed. Twenty-five ml of the amplification products are separated on 3.5% polyacrylamide gels. The gels are dried and scanned on an Ambis radioanalytic image system which allows for calculation of the cpm for each band. For calculation of the percentages of the different Vβ regions expressed, a ratio of Vβ cpm and Ca cpm for each Vβ region is calculated and the percentage of a singular region is computed in relation to the total of all 22 ratios as $$\% \text{ of Va (s)} = \frac{\text{cpm V}\beta \text{ (s)/cpm Ca}}{\sum (\text{cpm V}\beta / \text{cpm Ca})} \times 100$$

in which s is sample.

D. Sequencing Analysis. The amplified products of the PCR obtained from the Vb13.1 cDNA in a responding tumor lesion will be ligated into pBluescript SK vectors (Stratagene, La Jolla Calif.) which is subsequently used to transform XL-1 blue *Escherichia coli* (Stratagene). Plasmid DNA is isolated, denatured, and sequenced by the dideoxy chain termination procedure using the sequence 2.0 sequencing kit (United States Biochemicals. Cleveland, Ohio) according to the instructions provided by the company.

E. Staining and Flow Cytometry. Cultured PBL, TIL, or IVS cells will be stained with fluorescein or phycoerythrin-labeled monoclonal antibodies, including anti-CD3, CD8, CD4, IL2 receptor or IL receptor , CD56, and HLA-DR (Becton Dickinson, San Jose, Calif.) and examined by two-color flow cytometry isotype control antibodies. PBS controls will be included in all experiments.

F. Purification of RNA and cDNA Synthesis. RNA will be extracted using the RNAzol B method (Biotex Laboratories, Inc., Houston, Tex.). Briefly, cells are washed in PBS and subsequently treated with 0.2 ml. of the RNAzol B solution and 0.02 ml. of chloroform/$10^6$ cells. After vigorous shaking and cooling on ice for 5 min., the samples are centrifuged at 12,000×g at 4□ C. for 15 min. The aqueous RNA containing phase is removed and the RNA is precipitated with an equal volume of isopropyl alcohol for 15 min on ice and then sedimented and washed with 75% ethanol. cDNA will be synthesized from 2 mg of total RNA using a commercially available RNA PCR kit (Perkins-Elmer-Cetus, Norwalk, Conn.). The reaction is performed for 15 min using the following reagents: 50 mM KCl 10 mM Tris-HCI-5 mM MgCl$_2$.1 mM concentrations of deoxynucleotide triphosphate, 2.5 mm oligodeoxythymidylic acid primers, 1 unit/ml RNase inhibitor, and 2.5 units/ml Moloney murine leukemia virus reverse transcriptase-in a total volume of 40 ml. The reaction is stopped by heating the sample to 99° C. for 5 min.

Example 12

Treatment Protocol with Effector Cells

Overall Treatment Plan of Tumor Bearing Patients with Tumor Specific Effector Cells Eligible patients will be treated with irradiated autologous tumor cells at approximately 10 centimeters from a draining lymph node site. Ten days post vaccination vaccine draining lymph nodes will be obtained in a limited surgical procedure at the site draining the vaccination. The vaccine draining lymph nodes will be made into a single cell suspension of lymphocytes and these will be incubated with SEB followed by IL-2 as described below. These SEB stimulated vaccine draining lymph node lymphocytes will be then adoptively transferred to the patient who will also receive recombinant human IL-2 at a dose of 30,000 $\mu$/kg every 8 hours IV bolus×7 days. The patient will be followed at 4 and 8 weeks for clinical response and for the development of delayed type hypersensitivity reaction to autologous tumor. If sufficient autologous tumor cells are available, a second cycle will be pursued at 8 weeks for patients with stable or diminishing disease. The end point is disease response.

Adoptive Transfer and IL-2 Therapy

Cultures will be harvested by centrifugation at 500×g for 15 min and pooling the cell pellets. After washing the cells in HBSS, the cells will be resuspended in 200 ml of saline containing 5% human serum albumin and 450,000 IU of IL-2 for transfer. Cells will be infused through a subclavian central venous catheter over a 30-min interval. IL-2 administration i.v. will be commenced immediately after completion of cell infusion at a dose and schedule of 180,000 µU/ml every 8 h. for 5 days. All patients will receive indomethacin (50 mg p.o.) every 8 h, acetaminophen (650 mg p.o.) every 6 h. and ranitidine (150 mg p.o.) every 12 h while receiving IL-2 in order to reduce febrile and gastric side effects. Patients tolerating this IL-2 regimen will often be administered extra doses over an additional day.

A cohort of patients will be treated with tumor vaccination and IL-2 only. These will be patients who have similar tumor burdens as the other group of insufficient amounts of cryopreserved tumor for IVS culture. These patients will be treated with the identical vaccination procedure followed by IL-2 therapy 10 days later without LN excision. Patients will be followed every 4 wk for 2 mo. with repeat radiological examinations. All patients deemed to have stable or regressing disease by the end of that interval will be treated with a booster vaccination consisting of 1 to $2 \times 10^7$ irradiated (25 Gy) autologous tumor cells without BCG in two sites followed 10 days later by IL-2 therapy. A partial response was defined as a reduction of all measurable disease by 50% of the sum of the product of the two greatest perpendicular diameters without the appearance of new lesions. A minor response is defined as >25% but <50% reduction in all measurable lesions.

B. Treatment Plan for Reinfusing CTL from Peripheral Blood Mononuclear Cells or TILs or Eluted T cells from Immobilized Antibody Columns After Stimulation with Peptides Plus Superantigens or Peptide-Superantigen Conjugates or Tumor Cell-Superantigen Transfectants Clones of tumor specific cytotoxic T lymphocytes will be administered to each recipient intravenously over 30 minutes in four escalating doses (33 million, 100 million, 330 million and 1 billion cells per square meter of body surface area, each given one week apart. The patients will be followed for clinical response for 4 to 8 weeks. If sufficient T cells remain, a second cycle of treatment will be given at 8 weeks in patients with stable or diminishing disease.

C. Measurement of Effect

Grading and management of toxicity and dose modification are given in the attached clinical protocol.

D. Treatment Plan for Reinfusing Clonally Restricted TIL After Superantigen Therapy Following treatment with superantigen stimulated vaccine draining lymph nodes (SSVDL) measurable tumor sites will be carefully followed. In five cases, a regressing tumor nodule will be removed surgically. Tumor infiltrating lymphocytes (TIL) will be isolated from fresh surgical tissue and cultured. The cultured TIL will be classified with flow cytometry and Vβ gene expression quantitated. Should definitive Vβ clonality of infiltrating T cells be observed, these cells will be further cultured and expanded with SEB and IL-2. Care will be taken to avoid anergy of T cells. When sufficient numbers are obtained they will be reinfused into the patient. Each treatment will consist of infusion of $10^8$ cloned T cells given intravenously over 30 minutes, each given one week apart for a total of 4 treatments. The patients will be followed for clinical response for 4 to 8 weeks. If sufficient TIL remain, a second cycle of treatment will be given at 8 weeks in patients with stable or diminishing disease. Optimally IL-1, IL-4, IL-10 or IL-12 may be infused individually or together to prevent apoptosis and to sustain the antitumor activity of the infused cells.

Example 13

Variations of In Vitro Immunization

Variations of in vitro immunization utilize peptide bound to HLA-A1 or peptides plus superantigen plus class II molecules added sequentially. Alternatively, one may use conjugates or fusion proteins consisting of superantigens and peptides and —HLA-A1. An additional variation consists of using tumor cells transfected with superantigen and peptide genes or cotransfected with HLA class II genes to create a potent tumor cell vaccine.

Example 14

Enrichment and Deletion by Superantigens of Suppressor Populations in Autoimmune Disease and Cancer to Promote Therapeutic Efficacy In the MCA 205/207 tumor model, deletion of clone 3.0 with monoclonal antibodies attached to magnetic beads following ex vivo stimulation of tumor draining lymph node cells with SEB and IL-2 resulted in an augmentation of the tumor killing effects compared to the total T cell population. Deletion of other Vβ subsets (Vβ2 and Vβ6) produced the same result. Hence, the superantigens specific for the suppressor clones appeared to be removed which allowed for augmentation of antitumor effects. Hence, the superantigens will be used to delete these clones by anergizing them or by physically extracting them when they are bound to magnetic beads or other solid supports. The remaining T cell population devoid of the suppressor population will be expanded in IL-2 and reinfused into the host. In autoimmune disease, the superantigens may be used to delete the disease producing clone of T cells but may also be used to enrich the suppressor population of T cells which may help control the disease. The suppressor population may be extracted with immobilized superantigen and the eluted T cell population expanded in vitro with the same superantigen and then reinfused.

Example 15

Conjugation of Metal Chelating Groups to Superantigen for Therapeutic and Imaging Applications Superantigen molecules also may be modified with certain organic compounds able to form coordination complexes with metal atoms. Such chelating agents can be used to sequester radioactive or non-radioactive isotopes of metallic elements, particularly the Lanthanide series, to provide therapeutic or imaging capabilities. Examples of isotopes found useful for radiotherapy include iodine-131, iodine-125, bismuth-212, yttrium-90, yttrium-88, technetium-99m, copper-67, rhenium-188, rhenium-186, gallium-66, gallium-67, indium-111, indium-114m, indium-115, and boron -10.There are several methods commonly used to label proteins with radionuclides. In a direct labeling process, a radioactive atom is attached to functionalities on the polypeptide chain without the use of an intervening chemical group. For instance, radioiodination can be done through modification of tyrosine side chains on superantigen molecules using established techniques and reagents. Another direct method uses indigenous sulfhydryl groups or those formed through disulfide reduction to covalently couple certain metal nuclides (Holmberg and Meurling, 1993; Ranadive et al., 1993). Thiolation reagents also can be used in this regard to create the requisite—SH groups by modification of other protein functionalities (Joiris et al., 1991). Indirect methods of protein labeling with radiolabels utilize organic compounds able to chelate metal ions in a coordination complex. Bifunctional chelating agents (BCAs), as they are called, contain a chemical-reactive group for coupling to proteins or other molecules and a strong metal-chelating group for complexing certain radioactive metals. Their extensive use with monoclonal antibodies that are able to target specific cellular antigens has resulted in important radiopharmaceutical applications for the diagnosis and treatment of cancer (Meares, 1986; Otsuka and Welch, 1987; Liu and Wu, 1991; Hnatowich, 1990; Subramanian and Meares, 1991; Wessels and Rogus, 1984). The BCAs may be loaded with the radioactive metal before or after their conjugation with a protein (Frytak et al., 1991). If they are loaded with radionuclides prior to modifying the protein, the BCA-metal pair is called a preformed complex (Kasina et al., 1991). In one embodiment of the present invention, a superantigen is modified with one or more chelating agents and complexed with a radioactive metal for use in detecting its transport and distribution in vivo. In another embodiment, the superantigen-chelating complex is charged with a radioactive metal to enhance cell death at tumor sites in vivo. The superantigen-chelating complex may be further conjugated with a targeting component, such as an antibody or specific binding peptide, to facilitate its directed binding at tumor cells. Thus, this type of conjugate may contain several components synergistically working together to effect tumor cell death through specific targeting, immune modulation, and radiative cytotoxicity. Examples of some BCAs useful in modifying superantigen molecules include, but are not limited to, the following: DTPA (diethylenetriaminepentaacetic anhydride) (Hnatowich et al., 1982); DOTA (1,4,7,10-tetraazacyclododecane-N,N'N", N'"-tetraacetic acid) (Cox et al., 1990); NOTA (1,4,7-triazacyclononane-N,N',N"-triacetic acid) (Cox et al., 1990) 4) TETA (1,4,8,11-tetraazacyclotetradecane-N,N',N",N'"-tetraacetic acid) (Brechbiel et al., 1993); DTTA (N1-(p-isothiocyanatobenzyl)-diethylenetriaamine-N1,N2,N3,N3-tetraacetic acid) (Hemmila, 1988)6) DFA or desferoxamine (N'-[5-4[[4-[[5-(acetylhydroxyamino)pentyl]amino]-1,4-dioxobutyl]hydroxyamino]pentyl]-N-(5-aminopentyl)-N-hydroxybutanediamide), a naturally-occurring product isolated from *Streptomyces pilosus.* (Motta-Hennessy et al., 1985). Porphyrins (nitrogenous, cyclic molecules found as prosthetic groups of some proteins)8) Expanded Porphyrins or Texaphyrins (synthetic molecules that are similar to the porphyrin structure, but exist at larger cyclic systems) In addition, superantigen-chelating complexes may contain metals such as gadolinium and lutetium, which can produce an enhanced MRI signal for imaging applications or act as a radiation sensitizer or photosensitizer able to absorb x-ray or light energy and emit other forms of energy capable of discrete destruction of target tissue. The presence of a superantigen in such a complex can markedly enhance the immune response to the targeted cells, while the metal chelate provides the imaging or cytotoxic effects.

Example 16

Protocol #1

Anti-Tumor Effects of Infused Peptide-Superantigen Conjugates or Superantigen-Chelating Agents in Human Patients All patients treated have histologically confirmed malignant disease including carcinomas, sarcomas, melanomas, lymphomas and leukemia and have failed conventional therapy. Patients may be diagnosed as having any stage of metastatic disease involving any organ system. Staging describes both tumor and host, including organ of origin of the tumor, histologic type, histologic grade, extent of tumor size, site of metastases and functional status of the patient. A general classification includes the known ranges of Stage 1 (localized disease) to Stage 4 (widespread metastases). Patient history if obtained and physical examination performed along with conventional tests of cardiovascular and pulmonary function and appropriate radiologic procedures. Histopathology is obtained to verify malignant disease.

Treatment Procedure

1. Doses of the peptide-superantigen conjugates are determined as described above using, inter alia, appropriate animal models of tumors. Several types of therapeutic compositions are administered:
2. Peptide-superantigen conjugates prepared by direct cross-linking of a peptide antigen to a superantigen molecule using a homobifunctional or heterobifunctional cross-linking agent, comprising substantially 100% conjugates, and having a ratio of peptide-to-superantigen molecules of between 1:1 and 40:1. Peptide-superantigen conjugates prepared by direct cross-linking of a peptide antigen to a superantigen molecule using a zero-length cross-linking process (such as carbodiimide-mediated or reductive amination), comprising substantially 100% conjugates and having a ratio of peptide-to-superantigen molecules of between 1:1 and 10,000:1.
3. Peptide-superantigen conjugates prepared through covalent attachment to polymeric carriers, consisting of substantially 100% conjugates, and having ratios of peptide-to-superantigen that vary from equivalence (1:1) to as high as $10^6$:1 or even $10^8$:1 or as low as $10^{-6}$:1 or even $10^{-8}$:1
4. Peptide-superantigen conjugates prepared through covalent attachment of peptide and superantigen molecules to a carrier with subsequent non-covalent association of such modified carrier molecules to form large constructs containing ratios of peptide-to-superantigen that vary from equivalence (1:1) to as high as $10^6$:1 or even $10^8$:1 or as low as $10^{-6}$:1 or even $10^{-8}$:1. Such non-covalently-associated conjugates can consist of, for example, liposomal vesicles or large complexes formed through the interaction of biotin with avidin or streptavidin or similar biotin-binding proteins.

Treatment protocol uses peptide and superantigen doses of 1,100 or 100 mg polymer or peptide-superantigen as given in the human treatment protocol. Treatments are given 3×/week for a total of 12 treatments. Patients with stable or regressing disease are treated beyond the 12th treatment. Treatment is given on either an outpatient or inpatient basis as needed.

Patient Evaluation

Assessment of response of the tumor to the therapy is made once per week during therapy and 30 days thereafter. Depending on the response to treatment, side effects, and the health status of the patient, treatment is terminated or prolonged from the standard protocol given above. Tumor response criteria are those established by the International Union Against Cancer and are listed below.

| RESPONSE | DEFINITION |
|---|---|
| Complete remission (CR) | Disappearance of all evidence of disease |
| Partial remission (PR) | ≧50% decrease in the product of the two greatest perpendicular tumor diameters; no new lesions |
| Less than partial remission (<PR) | 25%–50% decrease in tumor size, stable for at least 1 month |
| Stable disease | <25% reduction in tumor size; no progression or new lesions |
| Progression | ≧25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements can be evaluated separately.

Results

One hundred and fit patients are treated. The results are summarized in Table 11. Positive tumor responses are observed in 80% of the patients as follows:

TABLE 11

| All Patients | Response | No. | % |
|---|---|---|---|
| | PR | 10 | 66% |
| | <PR | 20 | 33% |
| By Tumor Type: | Response | % of patients | |
| Breast Adenocarcinoma | PR+<PR | 80% | |
| Gastrointestinal Carcinoma | PR+<PR | 75% | |
| Lung carcinoma | PR+<PR | 75% | |
| Prostate Carcinoma | PR+<PR | 75% | |
| Lymphoma leukemia | PR+<PR | 75% | |
| Head and Neck Cancer | PR+<PR | 75% | |
| Renal and Bladder Cancer | PR+<PR | 75% | |
| Melanoma | PR+<PR | 75% | |

Toxicity

Toxicity is essentially the same as that observed in the RA patients described Above.

Protocol #2

Antitumor Effects of PBMC, TIL, Tumor Vaccine Primed Lymph Node Cells, Eluted T Cell from Immobilized Antibody Columns Activated in vitro by Tumor Associated Peptides and Superantigens, Peptide-Superantigen Conjugates or Superantigen Tumor Cell Transfectants Patient population, selection staging, pretreatment inclusion and exclusion criteria are identical to protocol #1 Treatment and Evaluation Methods.

Example 17

Attenuation of In vivo Toxicity by Preinfusion of Class II Binding Molecules The parenteral administration of toxins may result in attachment of the toxins to MHC class II binding sites in non-tumorous cells and hence divert the toxin from binding sites on the tumor cells. To avert this problem, the host will be preinfused with an MHC class II binding peptide which will block the class II sites on non tumor cells so that the subsequent infusion of toxin will target to the tumor. Such non-toxic class II binding molecules consist of peptides of enterotoxins which are known to bind to the $\alpha$ and $\beta$ chains of class II molecules. The enterotoxins have been shown to bind to regress on the MHC class II molecule which are distinct from the peptide binding groove. Mutagenesis studies identified portions of N-terminal domain that mediated binding to MHC class II. The N-terminal domain of SEB bound to the HLA-DR $\alpha$ chain. A C-terminal fragment of SEA which exhibited class II MHC binding and an N-terminal MHC class II binding epitope in SEB have been identified.

Hence, candidate molecules for class II blocking would be N-terminal and C-terminal conserved sequences of SEA that are known to bind to $\alpha$ and $\beta$ chains on two separate MHC class II molecules. The fragments may be of medium affinity as at the C-terminal site (Kd>>10 mM) and/or low affinity as at the N-terminal site (Kd>>10 mM).

Example 18

Therapeutic Usage of Peptide-Superantigen Conjugates and Activated T Cell Populations in Experimental Models and Human Autoimmune Diseases Peptide-Superantigen conjugates are tested and activated T cells are used for therapy in several well known models of arthritis and autoimmune disease in rodents. These include adjuvant, streptococcal cell wall, mycoplasma arthritides and collagen-induced arthritis) see, for example, Pearson, C. M., *Proc. Soc. Exp. Bio. Med.* 91:95 (1956); Cromartie, W. J. et al., *J. Exp. Med.* 146:1585 (1977); Trentham, D. E. et al., *J. Exp. Med.* 146:857 (1977); Chang, Y. H. et al., *Arthritis Rheum.* 23:62 (1980). For each of the models described above, treatment is started 6–14 days after the injection of the inducing agents (or in the case of MRL mice beginning at 4 weeks of age). Doses vary from 10 ng to 1 mg of peptide-superantigen polymers and are given I.V. at 1 week intervals for 4 weeks. Outcomes are assessed as described. For all arthritis models outcome measures include: (a) a quantitative measurement and grading of joint swelling erythema or deformity, and (b) assessment of histopathology of joints using a quantitative grading system. T cells obtained from regional lymph nodes of animals with active arthritis will be anergized in vitro with appropriate peptide and superantigen or superantigen mutants in order to inactivate the predominant V$\beta$ T cell clone. The T cell clone deleted of that T cell subset will then be administered parenterally into mice. T cell doses will range from $10^6$ to $10^8$ cells per treatment. Cells will be given weekly for 6 weeks. The effect in the arthritic process will be assessed using the criteria described for each model.

I. Streptococcal Cell Wall Arthritis Model (See Schwab, J. H. et al., J. Immunol. 150,4151–4159 (1993))

Induction and Measurements of Arthritis

Female Lewis rats weighing about 175 g are injected intraarticularly (i.a.) under ether anesthesia above the calcaneus through the Achilles tendon into the tibiotalar (ankle) joint on day 0 with 2.0 mg of rhamnose equivalents (approximately 6.0 mg dry weight) of 100 p peptidoglycan-polysaccharide from cell wall of group A Streptococci (PG-APS) suspended in 10 ml of pyrogen-free saline, as described previously (Esser, R. L., et al., Arthritis Rheum. 28:1402 (1985); Stimpson, S. A., et al., In: Pharmacological Methods in the Control of Inflammation, J. Chang et al., Eds. Alan R. Liss, Inc., New Your, P. 381 (1989)). Right or left joints are injected with PG-APS in alternate animals, and contralateral joints are injected with 10 ml of pyrogen-free saline. The lateral diameter of the ankle joint is measured with a Fowler Ultra-Cal II digital caliper (Lux Scientific Instrument Corp., New York, N.Y.). The average of three measurements for each joint is recorded. Results are presented as the mean±SE of the increase in joint diameter (difference between pre-and postreactivation).

Histopathology

Rats are sacrificed and the ankle joints are removed, skinned, fixed in formalin, decalcified, embedded in paraffin, sectioned sagitally, and stained with hematoxylin eosin. The significance of differences between groups is assessed by Student's two tail t-test.

Adjuvant Arthritis (AA) Model (See Chang et al., supra)

Male Lewis rats weighting 235–250 gm are used. Freund's complete adjuvant is either purchased commercially or prepared by grinding powdered *Mycobacterium butyricum* (10 mg; Difco Laboratories) with mineral oil (1.01 ml; Primol 355, Hampden Color Chemical Company). Adjuvant arthritis is produced by a single intradermal injection of the adjuvant into the tail or one hindpaw. The dose is about 0.5 mg heat killed Mycobacterium tuberculosis (Mt) suspended in 100 ml IFA. The volume of the uninjected hind paw is measured by the method of Winter et al., Proc. Soc. Exp. Biol. Med. 111,544 (1962) on day 0 and 16 (with respect to the injection of adjuvant). The increase in the volume of the uninjected hind paw serves as a measure of arthritis.

To determine the effect of a therapeutic composition, rats are treated with either saline or the composition each day from day-1 to day -15 (with respect to adjuvant injection). The initial paw volume (VI) is measured on the day of adjuvant injection. Sixteen days later, the volume (VF) of the uninjected hindpaw is measured. Percent inhibition is calculated according to the following equation:

$$\% \text{ inhibition} = 1 - \frac{\text{VF drug} - \text{VI drug}}{\text{VF control} - \text{VI control}} \times 100$$

Alternatively, severity of arthritis is assessed by scoring each paw from 0 to 4 based on degree of swelling, erythema, and deformity of the joints. Thus the maximum possible arthritis score is 16.

Collagen Type II Arthritis (CIA) Model (see Trentham et al., supra)

Sensitization Procedures. Collagen is dissolved in 0.1M acetic acid at a concentration of 1 mg/ml. Equal volumes of collagen solution and CFA or ICFA are mixed and emulsified. One ml of the cold emulsion is immediately injected intradermally in four to six sites on the backs of the rats. Small ulcers frequently form at the injection site, but these heal without sequelae in 7–10 days. Control injections consist of (a) acetic acid emulsified in CFA or ICFA or (b) human or chick type II collagen dissolved in acetic acid and injected intradermally without adjuvant. As an additional control, 1.0 ml of MgCl2-extractable cartilage proteoglycans containing approximately 200 mg uronate per ml is mixed with 0.5 ml of CFA or ICFA, emulsified, and injected as with collagens. Unless otherwise specified, booster doses consisting of 0.5 mg collagen dissolved in 0.5 ml 0.1M acetic acid are given i.p. without adjuvant 21 days after primary immunization. One ml of the $MgCl_2$ extract is given i.p. after an identical interval to the proteoglycan control animals. Adjuvant arthritis is induced by intradermal injection of 0.1 ml CFAH37 at the base of the tail.

Arthritis Evaluation. Animals are observed daily for the onset of arthritis, and an arthritic index is derived by grading the severity of involvement of each paw from 0 to 4. Scoring is based on the degree of periarticular erythema and edema as well as deformity of the joints (Wood, F. D., et al., Int. Arch. Allergy Appl. Immunol 35,456 (1969)). Swelling of hindpaws is also quantitated by measuring the thickness of the ankle from medial to lateral malleolus with a constant tension caliper (B. C. Ames Co., Waltham, Mass.). Results can be reproducibly expressed to the nearest 0.1 mm.

Histopathology. Animals are sacrificed, and involved paws are amputated on the day of onset of arthritis or at later periods ranging up to 6 mo. after onset. After immersion in 10% neutral formalin, the joints are decalcified, embedded in paraffin, sectioned, and stained with hematoxylin and eosin.

IV. Autoimmune Model MRL/lpr Mice (See: Kim, C. et al., J. Exp. Med. 174,1431–1437 (1991)). MRL/Mp-1pr mice (4–6 wk. old) are purchased from the Jackson Laboratory (Bar Harbor, Me.).

ELISA for Anti-DNA Antibodies and Circulating Immune Complexes

Polystyrene microtiter wells are coated with double-stranded DNA (ds-DNA) or goat C1q. Blood obtained from individual mice before the biweekly injections is pooled according to treatment group. Sera are diluted in 0.05% Tween-20 in PBS at a 1:500 dilution and allowed to incubate in the plates for 60 min at room temperature. The plates are then washed three times with PBS-Tween, and 50 ml of 1/1000 dilutions of goat anti-mouse IgG and IgM antibodies conjugated to urease (Sigma Chemical Co.) are added to the plates. After incubation for 30 min., the plates are then incubated with the urease substrate solution. The urease substrate solution is made according to manufacturer's instructions (Sigma). In short, 8 mg of bromcresol purple is dissolved in 1.48 ml of 0.01M NaOH and then diluted to 100 ml with water. 100 mg of urea and 3.7 mg of EDTA are dissolved, and the pH is adjusted to 4.8 by the addition of 0.01N NaOH. Colorimetric change is quantified by measuring absorbance at 590 nm using a microplate reader.

Proteinuria and Physical Symptoms

Urine (from at least 4 mice per group) is pooled according to treatment group. Protein concentration and the presence of blood in urine is measured semiquantitatively by commercial reagent strips for urinalysis. Physical symptoms are visually scored as: 0, no symptoms; 0.5, trace; 1–4, when visible symptoms are observed, with 4 being the most severe (physical symptoms include lymphadenomegaly, immune complex vasculitis, and necrosis of the ears). Scores representing physical symptoms are calculated by determining the total score for each group and then dividing by the number of animals alive in that group when the measurement is taken.

For each of the models described above, treatment is started 6–14 days after the injection of the inducing agents (or in the case of MRL mice beginning at 4 weeks of age). Doses vary from 10 ng to 1 mg of peptide-superantigen polymers or polymer conjugates and are given iv at 1 week intervals for 4 weeks. Outcomes are assessed as described. For all arthritis models outcome measures include: (a) a quantitative measurement and grading of joint swelling erythema or deformity, and (b) assessment of histopathology of joints using a quantitative grading system.

Example 19

Therapy of Rheumatoid Arthritis in Humans (See: McCarty, D. J., Arthritis and Allied Conditions—A Textbook of Rheumatology, 11th ed., Lea & Fibiger, Philadelphia 1989)

Treatment Procedure

Doses of the peptide-superantigen conjugates are determined as described above using, inter alia, appropriate animal models of autoimmune disease. Two types of therapeutic compositions are administered:

(1) Peptide-superantigen conjugates ranging in size from 64 kDa to 1000 kDa, comprising substantially 100% (w/w) polymers;

(2) Peptide-superantigen conjugates ranging in size from 1000 kDA to 10,000 kDa, comprising substantially 100% (w/w) polymers. A treatment consists of injecting the patient with 1 mg, 100 mg or 1000 mg peptide-superantigen conjugates intravenously in 200 ml of normal saline over a one hour period twice weekly at three day intervals for six weeks.

T cells are obtained from regional lymph nodes or PBMC and anergized in vitro with peptide and superantigen given sequentially or as peptide-superantigen conjugates. T cells will be harvested and given in doses of 108 to 1011 I.V. over 60 minutes as described in Example 8.12. The infusion will be given 3x/week for six weeks while parameters of arthritis are evaluated quantitatively on a weekly basis. Clinical responses are assessed by the criteria described below. Treatments are continued in patients with stable or exacerbating disease. Treatment is generally given on an outpatient basis.

Clinical Outcome Measures

Outcome measures used to assess treatment efficacy in RA should detect the smallest clinically important change and, at the same time, be reliable and valid with respect to capturing the dimensionality of the clinical and pathophysiologic responses. To avoid bias, both patients and assessors preferably are blinded during testing. The methods most commonly used are based on quantitation of cardinal features: pain, swelling, heat and redness. Laboratory tests may also be used in assessment, though a treatment that only reduces a laboratory measure without, for example, relieving joint pain is of less interest. No single ideal method is known to accurately reflect disease activity in arthritis. As a result, it is useful to aggregate end points into a composite index. Composite indices are constructed by statistical or judgmental procedures that allow aggregation of scores assigned to different end points.

Objective and sensitive measurements are preferred to subjective ones. One sensitive parameter to change with antirheumatic drug therapy in RA is the patient's subjective assessment of pain relief. Objective measurements include radionuclide joint uptake. Others are the 50-foot walking time and assessment of functional disability (the second most important symptom in osteoarthritis). Examples of useful outcome measures appear in Table 10, below.

Because pain is the major complaint of the rheumatic sufferer, measurement of pain relief is important in assessing clinical response to the therapeutic composition or method of this invention. Adjectival scales may be used with numeric values given to the adjectival scale, for example: 0=no pain, 1-slight pain, 2=moderate pain, 3=severe pain, and 4=extremely severe or agonizing pain. Such a scale is known to discriminate between nonsteroidal anti-inflammatory anaglesics and placebo in short-term trials (Lee, P., J. Rheumatol. 3:283–294 (1976)). Other methods of measuring pain include assessment of pain threshold and pain tolerance (Huskisson, E. C., Clin. Rheum. Dis. 2,37–49 (1976)).

TABLE 10

Outcome Measures for Clinical Trials in Arthritis
Altman, R. D. et al., Clin. Rheum. Dis. 9: 681–693 (1983)

| FDA Guidelines (1977) | Bellamy and Buchanan Clin. Rheumatol. 3: 293–305 (1984) |
|---|---|
| Joint swelling | Pain |
| Joint redness | Patient global assessment |
| Tenderness on pressure | Range of movement |
| Pain at rest or on motion | Physician global assessment |
| Range of motion | Joint stiffness |
| 50-foot walking time | Qualitative aspects of sleep |
| Clinician's global assessment | Walking time |
| Patient's global assessment | Activities of daily living |
|  | Joint tenderness |
| Altman et al. (supra) | Analgesic compound |
| Pain (using visual analogue scales) | Joint swelling |
| Tenderness on pressure/motion | Signal joints |
| Clinician's global assessment of current status and degree of change in status | Ascent time |
| Patient's global assessment of current status and degree of change in status | Muscle power |
| 50-foot walking time (for patients with hip and/or knee involvement) | Hand function |
| Grip strength (for patients with hand involvement) | Radiology |
|  | Joint temperature |

To score joint tenderness, firm digital pressure is applied to the joint margins and the degree of tenderness is graded by the patients response. Lansbury's Articular Index (Lansbury, J., Arthritis Rheum. 1,505–522 (1958)) is useful in assessing progress. A simple count of clinically active joints, as determined by pain on passive motion, tenderness on pressure, or inflammatory joint swelling is used (Cooperat. Clin. Comm. Amer. Rheum. Assoc., Clin. Pharmacol. Ther. 8,11–38 (1967)). Scoring a few selected "signal" joints may permit better assessment of therapeutic effect than a total joint count. A standardized soloimeter tested against the Lansbury indices is highly reproducible. The Ritchie Articular Index (RAI) is based on summation of joint responses after firm digital pressure. The responses are recorded as 0=no tenderness, +1=patient says it is tender, +2=patient says it is tender and winces, and +3=patient says it is tender, winces and withdraws limb. The sum of this Index is 78 and reflects exacerbations of disease and improvement induced by antirheumatic drugs. This index correlates with the patients assessment of pain, in the upper limbs with grip strength, and in the lower limbs with the time to walk 50 feet.

Various instruments are available to measure grip strength which is determined by the strength of the muscles in the forearm and hand, and the pain and degree of joint destruction in the wrist, hand, and finger joints; grip strength correlates with the RAI.

The range of motion of peripheral joints in normal subjects is known, and these measures have been assessed in studies of ankylosing spondylitis. Spinal movement is measured by several methods including the Dunham spondylometer (Hart, F. D. et al., Ann. Rheum. Dis. 14,77–89 (1955); Anderson, J. A. D., Clin. Rheum. Dis. 8,631–653 (1982)), skin distraction (Moll, J. M. H. et al., Rheum. Phys. Med. 11,293–312 (1972)), an inclinometer (Domjan, L. et al., Hung. Rheum., 28 (Suppl.): 71–76 (1987)).

Timing of certain movements or set maneuvers related to activities of daily living, are useful, in particular the time to walk 50 feet (Lee, supra; Grace, E. M. et al., Br. J. Rheumatol. 27,372–374 (1988)).

Increase in warmth of overlying skin is a cardinal feature of inflammation and can be measured in various ways (Bacon, P. A. et al., Clin. Rheum. Dis. 2,51–65 (1976)). Infrared quantitative thermography shows reproducible changes in disease activity and is useful in assessing efficacy of treatment composition or method (Ingpen, M. L., Ann. Phys. Med. 9,322–327 (1968)). Thermography provides a noninvasive, reproducible, sensitive, and quantifiable method of assessing improvement in joint inflammation.

Laboratory Tests

Certain laboratory tests reflect the severity of joint inflammation and may be used to monitor the efficacy of the therapeutic compositions and methods of this invention. The most frequently used test is the erythrocyte sedimentation rate (ESR). Other measures used include evaluation of various acute-phase reactants, such as C-reactive protein, haptoglobin, fibrinogen, a-2 macroglobulin, and plasma viscosity (McConkey, B. et al., Q.J. Med., New Series 41,115 (1972); McConkey, B. et al., Q.J. Med., New Series 42, 785 (1973); Constable, T. J. et al., Lancet 1,1176 (1975); Crook, L. Et al., Ann. Clin. Lab. Sci. 10,368 (1980); Dixon, J. A. et al., Scand. J. Rheumatol. 13,39 (1984); Cockel, R. et al., Ann. Rheum. Dis. 30,166 (1971)); titer of IgM rheumatoid factor or of immune complexes (Pope, R. M. et al., Ann. Rheum. Dis. 45, 183 (1986); Reeback J. S. et al., Ann. Rheum. Dis. 44,79 (1986); Reynolds, W. J. et al., J. Rheumatol. 13,700 (1986); tests of lymphocyte function (Reynolds, W. J. et al., J. Rheumatol. 13,700 (1986); Alepa, F. P. et al., Arthritis Rheum. 13,754 (1970); Swanson, M. A. et al., N. Engl. J. Med. 277,163 (1967); displacement of L-tryptophan from serum albumin; serum iron concentration (Cockel, supra), eosinophilia, thrombocytosis (Hutchinson, R. M. et al., Ann. Rheum. Dis. 35,138 (1976)); serum concentrations of sulfhydryl groups (Lorber, A. et al., Metabolism 20,446 (1971); serum copper concentrations (Brown, D. H. et al., Ann. Rheum. Dis. 38,174 (1979)); serum propeptide levels (Horsley-Petersen et al., Rheum. 29,592 (1986)); synovial fluid analysis (Hall, S. H. et al., Ann. Rheum. Dis. 37,351 (1978)).

Various methods are used to score radiologic changes in rheumatoid arthritis, the most useful of which are count erosions and assessment of joint space narrowing. Radionuclides are used to quantify joint inflammation (Dick, W. C., Semin. Arthritis Rheum. 1,301 (1972); Dick, W. C. et al., Clin. Rheum. Dis. 2,67 (1976); Wallace, D. J. et al., Arthritis Rheum. 11,172 (1981)). These are administered intra-articularly and the rate of clearance from the joint determined or, alternatively, they are administered iv and the rate of accumulation over a joint (or joints) measured. The clearance of $133_{Xe}$ after intra-articular injection provides an indirect measurement of synovial blood flow. $99_{mTcO4}$ is also used. Radionuclide joint uptake in both large and small joints is reduced with successful anti-rheumatic therapeutics such as NSAIDs, corticosteroids, gold or D-penicillamine.

Results

Three hundred patients with RA are treated. According to the 8 measures listed under "FDA Guidelines" in Table 10, above, greater than 80% of the treated patients show significant cumulative improvement across all measures.

Toxicity

The incidence of side effects (as % of total treatments) are as follows: chills-10; fever-10; pain-5; nausea-5; respiratory-3; headache-3; tachycardia-2; vomiting-2; hypertension-2; hypotension-2; joint pain-2; rash-2; flushing-1; diarrhea-1; itching/hives-1; bloody nose-1; dizziness-<1; cramps-<1; fatigue-<1; feeling faint-<1; twitching-<1; blurred vision-<1; gastritis-<1; redness on hand-<1. Fever and chills are the most common side effects observed. Side effects are somewhat less frequent in patients treated with SpA polymers compared with SpA-SEB polymers. Side effects are less prevalent with the 1 mg and 100 mg SpA-SEB polymer infusions but this is not statistically different from the group receiving 1000 mg infusions. Other minor changes observed are clinically insignificant.

Example 20

Antitumor Effects of Peptide-Superantigen Conjugates in Animal Models of Human Tumors The peptide-superantigen conjugates are tested for therapeutic efficacy in several well established rodent models which are considered to be highly representative of a broad spectrum of human tumors. These approaches are described in detail in Geran, R. I. et al., "Protocols for Screening Chemical Agents and Natural Products Against Animal Tumors and Other Biological Systems (Third Edition)", Canc. Chemother. Reports, Part 3, 3:1–112, which is hereby incorporated by reference in its entirety.

Treatment of Tumor Models with Effector T Cells

Effector T cells will be generated from regional lymph nodes of mice bearing 3–7 day old tumors implanted in close proximity to the lymph nodes. The cells will be incubated with peptide and superantigen sequentially for 2 and 3 days respectively after which they will be harvested and infused into tumor bearing mice. Peptide-superantigen conjugates or fusion proteins and tumor cells transfected with superantigen genes may be similarly cultured with lymph node cells for 3 days after which the cells are harvested and reinfused into animals bearing the tumor under study. T cells may be given parenterally in doses of $10^6$–$10^8$ cells weekly. Assessment is carried out as given below for each model.

Protocol for Immunization of Hosts with Tumor Cells Transfected with Superantigens and/or α-Gal A. Use of Transfectants as a Vaccine or to Treat Established Tumors The tumor cells transfected with superantigens, class II, class I, B-7 and α-Gal genes are tested for therapeutic efficacy in several well established rodent models which are given in Example 20. They are considered to be highly representative of a broad spectrum of human tumors. Transfected tumor cells ($10^5$–$10^7$) will be given 30 days to 6 months before implantation of the native tumor ($10^5$–$10^7$ tumor cells). Tumor growth and/or survival of the treated group is statistically superior to that of untreated tumor bearing controls. Transfected cells may also be given after tumors are established after implantation and are palpable. Tumor growth is aborted and/or survival is prolonged in treated animals compared to untreated tumor bearing controls in a statistically significant fashion.

B. In Vitro Immunization

Tumor cells transfected with superantigen, class II, class I, B-7 genes or α-Gal genes may be used to immunize T cells in vitro. T cells to be immunized are obtained from sources including but not limited to peripheral blood, tumor draining lymph nodes and spleen. Tumor cell transfectants $10^5$ cells/ml are incubated with T cells for 24–72 hours. The tumor transfectants are then removed and the T cells are further expanded with IL-2 over the next 72 hours. The T cells are harvested and then reinfused into hosts bearing established tumors. Infusions will be given I.V. every 6–12 days in doses of $10^6$–$10^7$ cells treatment. Tumor size and survival in treated animals show substantial antitumor effects compared to the untreated controls.

General Test Evaluation Procedures

A. Calculation of Mean Survival Time

Mean survival time is calculated according to the following formula:

$$\text{Mean survival time (days)} = \frac{SS + AS(A-1) - (B+1)NT}{S(A-1) - NT}$$

Definitions

Day: Day on which deaths are no longer considered due to drug toxicity. Example: With treatment starting on Day 1 for survival systems (such as L1210, P388, B16, 3LL, and W256): Day A: Day 6.

Day B: Day beyond which control group survivors are considered "no-takes." Example: With treatment starting on Day 1 for survival systems (such as L1210, P388, and W256), Day B=Day 18. For B16, transplanted AKR, and 3LL survival systems, Day B is to be established.

SS: If there are "no-takes" in the treated group, SS is the sum from Day A through Day B. If there are "no takes" in the treated group, SS is the sum of daily survivors from Day A onward. S(A-1): Number of survivors at the end of Day (A-1). NT: Number of "no-takes".

B. T/C Computed for All Treated Groups

T/C is the ratio (expressed as a percent) of the mean survival time of the treated group divided by the mean survival time of the control group. Treated group animals surviving beyond Day B, according to the chart below are eliminated from calculations:

| Percent of small tumors in treated group | Percent of "no-takes" in control group | Action |
| --- | --- | --- |
| ≦17 | Any percent | no-take; not used in calculations |
| 18–39 | <10 | drug inhibition; use in calculations |
|  | ≧10 | no-takes; not used in calculations |
| ≧40 | <15 | drug inhibition; use in calculations |
|  | ≧15 | Code all nontoxic tests "33" |

Positive control compounds are not considered to have "no-takes" regardless of the number of "no-takes" in the control group. Thus, all survivors on Day B are used in the calculation of T/C for the positive control. Surviving animals are evaluated and recorded on the day of evaluation as "cures" or "no-takes."

Calculation of Median Survival Time

Median Survival Time is defined as the median day of death for a test or control group. If deaths are arranged in chronological order of occurrence (assigning to survivors, on the final day of observation, a "day of death" equal to that day), the median day of death is a day selected so that one half of the animals died earlier and the other half died later or survived.

If the total number of animals is odd, the median day of death is the day that the middle animal in the chronologic arrangement died. If the total number of animals is even, the median is the arithmetical mean of the two middle values. Median survival time is computed on the basis of the entire population and there are no deletion of early deaths or survivors with the following exception:

C. Computation of Median Survival Time from Survivors

If the total number of animals including survivors (N) is even, the median survival time (days) (X+Y)/2, where X is the earlier day when the number of survivors is <(N/2)−1. If N is odd, the median survival time (days) is X.

D. Computation of Median Survival Time from Mortality Distribution

If the total number of animals including survivors (N) is even, the median survival time (days) (X+Y)/2, where X is the earliest day when the cumulative number of deaths is >(N/2, and Y is the earliest day when the cumulative number of deaths is (N/2)+1. If N is odd, the median survival time (days) is X.

Cures and "No-Takes": "Cures" and "no-takes" in the systems evaluated by median survival time are based upon the day of evaluation. On the day of evaluation any survivor not considered a "no-take" is recorded as a "cure". Survivors on day of evaluation are recorded as "cures" or "no-takes", but not eliminated from the calculation of the median survival time.

E. Calculation of Approximate Tumor Weight from Measurement of Tumor Diameters with Vernier Calipers The use of diameter measurements (with Vernier calipers) for estimating treatment effectiveness on local tumor size permits retention of the animals for lifespan observations. When the tumor is implanted sc, tumor weight is estimated from tumor diameter measurements as follows. The resultant local tumor is considered a prolate ellipsoid with one long axis and two short axes. The two short axes are assumed to be equal. The longest diameter (length) and the shortest diameter (width) are measured with Vernier calipers. Assuming specific gravity is approximately 1.0, and II is about 3, the mass (in mg) is calculated by multiplying the length of the tumor by the width squared and dividing the product by two.

$$\text{Tumor weight (mg)} = \frac{\text{length (mm)} \times (\text{width [mm]})^2}{2} \text{ or } \frac{L \times (W)^2}{2}$$

The reporting of tumor weights calculated in this way is acceptable inasmuch as the assumptions result in as much accuracy as the experimental method warrants.

F. Calculation of Tumor Diameters

The effects of a drug on the local tumor diameter may be reported directly as tumor diameters without conversion to tumor weight. To assess tumor inhibition by comparing the tumor diameters of treated animals with the tumor diameters of control animals, the three diameters of a tumor are averaged (the long axis and the two short axes). A tumor diameter T/C of 75% or less indicates activity and a T/C of 75% is approximately equivalent to a tumor weight T/C of 42%.

G. Calculation of Mean Tumor Weight from Individual Excised Tumors

The mean tumor weight is defined as the sum of the weights of individual excised tumors divided by the number of tumors. This calculation is modified according to the rules listed below regarding "no-takes." Small tumors weighing 39 mg or less in control mice or 99 mg or less in control rats, are regarded as "no-takes" and eliminated from the computations. In treated groups, such tumors are defined as "no-takes" or as true drug inhibitions according to the following rules:

| Percent of small tumors in treated group | Percent of "no-takes" in control group | Action |
| --- | --- | --- |
| ≦17 | Any percent | no-take; not used in calculations |
| 18–39 | <10 | drug inhibition; use in calculations |
| | ≧10 | no-takes; not used in calculations |
| ≧40 | <15 | drug inhibition; use in calculations |
| | ≧15 | Code all nontoxic tests "33" |

Positive control compounds are not considered to have "no-takes" regardless of the number of "no-takes" in the control group. Thus, the tumor weights of all surviving animals are used in the calculation of T/C for the positive control. T/C are computed for all treated groups having more than 65% survivors. The T/C is the ratio (expressed as a percent) of the mean tumor weight for treated animals divided by the mean tumor weight for control animals. SDs of the mean control tumor weight are computed the factors in a table designed to estimate SD using the estimating factor for SD given the range (difference between highest and lowest observation). Biometrik Tables for Statisticians (Pearson E S, and Hartley H G, eds.) Cambridge Press, Vol. 1, table 22, p. 165.

II. Specific Tumor Models

A. Lymphoid Leukemia L1210

Summary: Ascitic fluid from donor mouse is transferred into recipient BDF1 or CDF1 mice. Treatment begins 24 hours after implant. Results are expressed as a percentage of control survival time. Under normal conditions, the inoculum site for primary screening is i.p., the peptide-superantigen polymeric composition is administered i.p., and the parameter is mean survival time. Origin of tumor line: induced in 1948 in spleen and lymph nodes of mice by painting skin with MCA. J. Natl. Cancer Inst. 13:1328, 1953.

Animals

Propagation: DBA/2 mice (or BDF1 or CDF1 for one generation).

Testing: BDF1 (D57BL/6×DBA/2) or CDF1 (BALB/c× DBA/2) mice.

Weight: Within a 3-g weight range, with a minimum weight of 18 g for males and 17 g for females.

Sex: One sex used for all test and control animals in one experiment.

Experiment Size: Six animals per test group.

Control Groups: Number of animals varies according to number of test groups.

Tumor Transfer

Inject i.p., 0.1 ml of diluted ascitic fluid containing 105 cells. Time of Transfer for propagation: Day 6 or 7. Time of Transfer for Testing: Day 6 or 7.

Testing Schedule

Day 0: Implant tumor. Prepare materials. Run positive control in every odd-numbered experiment. Record survivors daily.

Day 1: Weigh and randomize animals. Begin treatment with therapeutic composition. Typically, mice receive 1 mg of peptide-superantigen polymer or polymer conjugate in 0.5 ml saline. Controls receive saline alone. The treatment is given as one dose per week. Any surviving mice are sacrificed after 4 weeks of therapy.

Day 5: Weigh animals and record.

Day 20: If there are no survivors except those treated with positive control compound, evaluate study.

Day 30: Kill all survivors and evaluate experiment.

Quality Control

Acceptable control survival time is 8–10 days. Positive control compound is 5-fluorouracil; single dose is 200 mg/kg/injection, intermittent dose is 60 mg/kg/injection, and chronic dose is 20 mg/kg/injection. Ratio of tumor to control (T/C) lower limit for positive control compound is 135%.

Evaluation

Compute mean animal weight on Days 1 and 5, and at the completion of testing compute T/C for all test groups with >65% survivors on Day 5. A T/C value <85% indicates a toxic test. An initial T/C>125% is considered necessary to demonstrate activity. A reproduced T/C>125% is considered worthy of a further study. For confirmed activity a composition should have two multi-dose assays that produce a T/C>125%.

B. Lymphocytic Leukemia P388

Summary: Ascitic fluid from donor mouse is implanted in recipient BDF1 or CDF1 mice. Treatment begins 24 hours after implant. Results are expressed as a percentage of control survival time. Under normal conditions, the inoculum site for primary screening is ip. The peptide-superantigen polymeric composition is administered ip daily for 9 days, and the parameter is median survival time. Origin of tumor line: induced in 1955 in a DBA/2 mouse by painting with MCA. Scientific Proceedings, Pathologist and Bacteriologists 33:603, 1957.

Animals

Propagation: DBA/2 mice (or BDF1 or CDF1 for one generation).Testing: BDF1 (D57BL/6×DBA/2) or CDF1 (BALB/c×DBA/2) mice. Weight: Within a 3-g weight range, with a minimum weight of 18 g for males and 17 g for females. Sex: One sex used for all test and control animals in one experiment. Experiment Size: Six animals per test group. Control Groups: Number of animals varies according to number of test groups.

Tumor Transfer

Implant: Inject i.p.

Size of Implant: 0.1 ml of diluted ascitic fluid containing $10^5$ cells.

Time of Transfer for Propagation: Day 6 or 7.

Time of Transfer for Testing: Day 6 or 7.

Testing Schedule

Day 0: Implant tumor. Prepare materials. Run positive control in every odd-numbered experiment. Record survivors daily.

Day 1: Weigh and randomize animals. Begin treatment with therapeutic composition. Typically, mice receive lmg of peptide-superantigen polymer or polymer conjugate in 0.5 ml saline. Controls receive saline alone. The treatment is given as one dose per week. Any surviving mice are sacrificed after 4 weeks of therapy. Day 5: Weigh animals and record.

Day 20: If there are no survivors except those treated with positive control compound, evaluate study.

Day 30: Kill all survivors and evaluate experiment.

Quality Control

Acceptable control survival time is 8–10 days. Positive control compound is 5-fluorouracil; single dose is 200 mg/kg/injection, intermittent dose is 60 mg/kg/injection, and chronic dose is 20 mg/kg/injection. Ratio of tumor to control (T/C) lower limit for positive control compound is 135%.

Evaluation

Compute mean animal weight on Days 1 and 5, and at the completion of testing compute T/C for all test groups with >65% survivors on Day 5. A T/C value <85% indicates a toxic test. An initial T/C>125% is considered necessary to demonstrate activity. A reproduced T/C>125% is considered worthy of a further study. For confirmed activity a composition should have two multi-dose assays that produce a T/C>125%.

C. Melanotic Melanoma B16

Summary: Tumor homogenate is implanted ip or sc in BDF1 mice. Treatment begins 24 hours after eight ip or sc implant or is delayed until an sc tumor of specialized size (usually approximately 400 mg) can be palpated. Results expressed as a percentage of control survival time. The peptide-superantigen polymeric composition is administered ip, and the parameter is mean survival time. Origin of tumor line: arose spontaneously in 1954 on the skin at the base of the ear in a C57BL/6 mouse. Handbook on Genetically Standardized Jax Mice. Roscoe B. Jackson Memorial Laboratory, Bar Harbor Me., 1962. See also Ann NY Acad Sci 100, Parts 1 and 2, 1963.

Animals

Propagation: C57BL/6 mice.

Testing: BDF1 (C57BL/6×DBA/2) mice.

Weight: Within a 3-g weight range, with a minimum weight of 18 g for males and 17 g for females.

Sex: One sex used for all test and control animals in one experiment.

Experiment Size: Ten animals per test group.

Control Groups: Number of animals varies according to number of test groups.

Tumor Transfer

Implant: Implant fragment sc by trochar or 12-guage needle or tumor homogenate (see below) every 10–14 days into axillary region with puncture in inguinal region.

Testing: Excise sc tumor on Day 10–14.

Homogenate: Mix 1 g or tumor with 10 ml of cold balanced salt solution and homogenize, and implant 0.5 ml of this tumor homogenate ip or sc. Fragment: A 25-mg fragment may be implanted sc.

Testing Schedule

Day 0: Implant tumor. Prepare materials. Run positive control in every odd-numbered experiment. Record survivors daily.

Day 1: Weigh and randomize animals. Begin treatment with therapeutic composition. Typically, mice receive lmg of peptide-superantigen polymer in 0.5 ml saline. Controls receive saline alone. The treatment is given as one dose per week. Any surviving mice are sacrificed after 8 weeks of therapy.

Day 5: Weigh animals and record.

Day 20: If there are no survivors except those treated with positive control compound, evaluate study.

Day 30: Kill all survivors and evaluate experiment.

Quality Control

Acceptable control survival time is 14–22 days. Positive control compound is 5-fluorouracil; single dose is 200 mg/kg/injection, intermittent dose is 60 mg/kg/injection, and chronic dose is 20 mg/kg/injection. Ratio of tumor to control (T/C) lower limit for positive control compound is 135% Check control deaths, no takes, etc.

Evaluation

Compute mean animal weight on Days 1 and 5, and at the completion of testing compute T/C for all test groups with >65% survivors on Day 5. A T/C value <85% indicates a toxic test. An initial T/C>125% is considered necessary to demonstrate activity. A reproduced T/C>125% is considered worthy of a further study. For confirmed activity a composition should have two multi-dose assays that produce a T/C>125%.

Metastasis After IV Injection of Tumor Cells $10^5$ B16 melanoma cells in 0.3 ml saline are injected intravenously in C57BL/6 mice. The mice are treated intravenously with 1 mg of peptide-superantigen polymers or polymer conjugate in 0.5 ml saline. Controls receive saline alone. The treatment is given as one dose per week. Mice are sacrificed after 4 weeks of therapy, the lungs are removed and metastases are enumerated.

D. 3LL Lewis Lung Carcinoma

Summary: Tumor may be implanted sc as a 2–4 mm fragment, or im as a $2\times1I10^6$-cell inoculum. Treatment begins 24 hours after implant or is delayed until a tumor of specified size (usually approximately 400 mg) can be palpated. The peptide-superantigen polymeric composition is administered ip daily for 11 days and the results are expressed as a percentage of the control. Origin of tumor line: arose spontaneously in 1951 as a carcinoma of the lung in a C57BL/6 mouse. Cancer Res 15:39, 1955. See, also Malave, I. et al., J. Nat'l. Canc. Inst. 62:83–88 (1979).

Animals

Propagation: C57BL/6 mice.

Testing: BDF1 mice or C3H.

Weight: Within a 3-g weight range, with a minimum weight of 18 g for males and 17 g for females.

Sex: One sex use for all test and control animals in one experiment.

Experiment size: Six animals per test group for sc implant, or ten for im implant. For control groups, the number of animals varies according to number of test groups.

Tumor Transfer

Implant: Inject cells im in hind leg or implant fragment sc in axillary region with puncture in inguinal region.

Time of transfer for Propagation: Days 12–14.

Time of transfer for Testing: Days 12–14.

Testing Schedule

Day 0: Implant tumor. Prepare materials. Run positive control in every odd-numbered experiment. Record survivors daily.

Day 1: Weigh and randomize animals. Begin treatment with therapeutic composition. Typically, mice receive 1 mg of peptide-superantigen polymer or polymer conjugate in 0.5 ml saline. Controls receive saline alone. The treatment is given as one dose per week. Any surviving mice are sacrificed after 4 weeks of therapy.

Day 5: Weigh animals and record.

Day 20: If there are no survivors except those treated with positive control compound, evaluate study.

Final Day: Kill all survivors and evaluate experiment.

Quality Control

Acceptable im tumor weight on Day 12 is 500–2500 mg. Acceptable im tumor median survival time is 18–28 days. Positive control compound is cyclophosphamide: 20 mg/kg/injection, qd, Days 1–11. Check control deaths, no takes, etc.

Evaluation

Compute mean animal weight when appropriate, and at the completion of testing compute T/C for all test groups. When the parameter is tumor weight, a reproducible T/C<42% is considered necessary to demonstrate activity. When the parameter is survival time, a reproducible T/C>125% is considered necessary to demonstrate activity. For confirmed activity a synthetic must have two multi-dose assays (each performed at a different laboratory); a natural product must have two different samples.

E. 3LL Lewis Lung Carcinoma Metastasis Model

This model has been utilized by a number of investigators. See, for example, Gorelik, E. et al., J. Nat'l. Canc. Inst. 65:1257–1264 (1980); Gorelik, E. et al., Rec. Results Canc. Res. 75:20–28 (1980); Isakov, N. et al., Invasion Metas. 2:12–32 (1982) Talmadge J. E. et al., J. Nat'l. Canc. Inst. 69:975–980 (1982); Hilgard, P. et al., Br. J. Cancer 35:78–86 (1977)). Mice are male inbred C57BL/6 mice, 2–3 months old.

Tumor: The 3LL Lewis Lung Carcinoma was maintained by sc transfers in C57BL/6 mice. Following sc, im or intrafoot pad transplantation, this tumor produces metastases, preferentially in the lungs. Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95–99% (by trypan blue dye exclusion). Viable tumor cells ($3\times10^4$–$5\times10^6$) suspended in 0.05 ml PBS are injected into the right hind foot pads of C57BL/6 mice. The day of tumor appearance and the diameters of established tumors are measured by caliper every two days. Typically, mice receive 1 mg of peptide-superantigen polymer or polymer conjugate in 0.5 ml saline. Controls receive saline alone. The treatment is given as one or two doses per week. In experiments involving tumor excision, mice with tumors 8–10 mm in diameter are divided into two groups. In one group, legs with tumors are amputated after ligation above the knee joints. Mice in the second group are left intact as nonamputated tumor-bearing controls. Amputation of a tumor-free leg in a tumor-bearing mouse has no known effect on subsequent metastasis, ruling out possible effects of anesthesia, stress or surgery. Surgery is performed under Nembutal anesthesia (60 mg veterinary Nembutal per kg body weight).

Determination of Metastases, Spread and Growth

Mice are killed 10–14 days after amputation. Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur, M. L. et al., J. Lab. Clin. Med. 89:217–228 (1977). Ten days following tumor amputation, 25 mg of fluorodeoxyuridine is inoculated into the peritoneums of tumor-bearing (and, if used, tumor-resected mice. After 30 min, mice are given 1 mCi of $^{125}$IdUrd (iododeoxyuridine). One day later, lungs and spleens are removed and weighed, and a degree of $^{125}$IdUrd incorporation is measured using a gamma counter.

Statistics: Values representing the incidence of metastases and their growth in the lungs of tumor-bearing mice are not normally distributed. Therefore, non-parametric statistics such as the Mann-Whitney U test may be used for analysis. Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of large doses of 3LL cells ($1-5\times10^6$) followed by surgical removal, the number of metastases was lower than that in nonoperated tumor-bearing mice, though the volume of metastases was higher than in the nonoperated controls. Using 125₁dUrd incorporation as a measured of lung metastases, no significant differences were found between the lungs of tumor-excised mice and tumor-bearing mice originally inoculated with $1\times10^6$ 3LL cells. Amputation of tumors produced following inoculation of $1\times10^5$ tumor cells dramatically accelerated metastatic growth. These results were in accord with the survival of mice after excision of local tumors. The phenomenon of acceleration of metastatic growth following excision of local tumors had been observed by other investigators. The growth rate and incidence of pulmonary metastases were highest in mice inoculated with the lowest doses ($3\times10^4$–$1\times10^5$) of tumor cells and characterized by the longest latency periods before local tumor appearance. Immunosuppression accelerated metastatic growth, though nonimmunologic mechanisms participate in the control exerted by the local tumor on lung metastasis development. These observations have implications for the prognosis of patients who undergo cancer surgery.

F. Walker Carcinosarcoma 256

Summary: Tumor may be implanted sc in the axillary region as a 2–6 mm fragment, im in the thigh as a 0.2-ml inoculum of tumor homogenate containing $10^6$ viable cells, or ip as a 0.1-ml suspension containing $10^6$ viable cells. Peptide-superantigen polymeric composition treatment is usually ip. Origin of tumor line: arose spontaneously in 1928 in the region of the mammary gland of a pregnant albino rat. J Natl Cancer Inst 13:1356, 1953.

Animals

Propagation: Random-bred albino Sprague-Dawley rats.

Testing: Fischer 344 rats or random-bred albino rats.

Weight Range: 50–70 g (maximum of 10-g weight range within each experiment).

Sex: One sex used for all test and control animals in one experiment.

Experiment Size: Six animals per test group. For control groups, the number of animals varies according to the number of test groups.

Time of Tumor Transfer

Time of Transfer for Propagation: Day 7 for im or ip implant; Days 1–13 for sc implant.

Time of Transfer for Testing: Day 7 for im or ip implant: Days 11–13 for sc implant.

Tumor Transfer Sc fragment implant is by trochar or 12-guage needle into axillary region with puncture in inguinal area. Im implant is with 0.2 ml of tumor homogenate (containing $10^6$ viable cells) into the thigh. Ip implant is with 0.1 ml of suspension (containing $10^6$ viable cells) into the ip cavity.

Testing Schedule

Prepare and administer peptide-superantigen polymeric compositions on days 1–9. Weigh animals on days 1 and 5 and evaluate on day 30.

Day 0: Implant tumor. Prepare materials. Run positive control in every odd-numbered experiment. Record survivors daily.

Day 1: Weigh and randomize animals.

Final Day: Kill all survivors and evaluate experiment.

Quality Control

Acceptable im tumor weight or survival time: 3–12 g. or 5WA21: 5–9 days.

Evaluation

Compute mean animal weight when appropriate, and at the completion of testing compute T/C for all test groups. When the parameter is tumor weight, a reproducible TC<42% is considered necessary to demonstrate activity. When the parameter is survival time, a reproducible T/C>125% is considered necessary to demonstrate activity. For confirmed activity a therapeutic agent must have activity in two multi-dose assays.

G. A20 Lymphoma $10^6$ murine A20 lymphoma cells in 0.3 ml saline are injected subcutaneously in BALB/c mice. The mice are treated intravenously with 1 mg peptide-superantigen polymers or polymer conjugates in 0.5 ml saline. Controls receive saline alone. The treatment is given as one dose per week. Tumor growth is monitored daily by physical measurement of tumor size and calculation of total tumor volume. After 4 weeks of therapy the mice are sacrificed. Additional tumor models of carcinoma and sarcoma originating from various primary sites and prepared as established tumors are primary and/or metastatic sites will be utilized to test further the efficacy of the peptide-superantigen polymers.

Example 21

Heterospecific Antigen-Superantigen Polymers to Produce Tolerance in Recipients of Heterologous Organ Transplants: Tolerance Inducing Regimen in Recipients of Organ Heterografts Inject superantigen-αGal conjugate in doses of 1 ng to 100 mg (molar ratios of SAG to αGal of 1:10 to 1:106) using parenteral or oral route of administration. The conjugates may be placed in appropriate vehicles as given in Example 6 and infused over 1–4 hours in 500 cc of normal saline. The dose may be repeated every 2 and/or 3rd day depending on the strength of tolerance produced. Antibodies specific for αGal would be expected to increase initially during the sensitization phase and then begin to decline as anergy to the αGal antigen prevails. When titers are undetectable, the recipients would then be transplanted with the heterograft. Anergy may also be produced in recipients of organ heterografts by administering the αGal and superantigen sequentially at 2 or 3 day intervals. Alternatively transgenic animals could be created using the transgene for a1, 3-galactosyltransferase with the appropriate tissue specific promoter to produce organs that do not express the α-Gal antigen. In addition anti-sense nucleotides may be used to bind and disable proteins or block function by preventing the translation of messenger RNA (MRNA) into protein. The antisense nucleotides for the α-Gal system will block the synthesis of the somatic gene product. The anti-sense nucleotides may be delivered parenterally or directly into organs or attached to proteins or liposomes.

Incorporation by Reference

All publications, patents and patent applications referred to ion this specification are specifically incorporated by reference.

This application hereby incorporates by reference U.S. patent application Ser. No. 07/416,530, filed Oct. 3, 1989; U.S. patent application Ser. No. 07/466,577, filed Jan. 17, 1990; U.S. patent application Ser. No. 07/891,718, filed Jun. 1, 1992; U.S. patent application Ser. No. 08/025,144, filed Mar. 2, 1993; U.S. patent application Ser. No. 08/189,424, filed Jan. 31, 1994; U.S. patent application Ser. No. 08/491, 746 filed Jun. 19, 1995; PCT application PCT/US/91/00342, and PCT/US/94/02339. In the even that any material in the applications incorporated by reference is found to conflict between the different applications and such material is necessary to support the claims, the information disclosed in the later-filed application is to take precedence.

Equivalents

Manly embodiments of the inventions described herein are provided. The person of ordinary skill in the art of immunology will be able to practice numerous equivalents of the inventions described herein. Such equivalents are intended to be within the scope of the following claims.

What is claimed is:

1. A pharmaceutical compound comprising a therapeutic antigen and superantigen, wherein said super antigen is conjugated to the therapeutic antigen and wherein the therapeutic antigen does not comprise an antigen binding region of an antibody.

2. A pharmaceutical compound according to claim 1, wherein the therapeutic antigen is a tumor specific antigen.

3. A pharmaceutical compound according to claim 2, wherein the tumor specific antigen is selected from the group consisting of MAGE-1, MAGE-3, MART-1, and tyrosinase.

4. A pharmaceutical compound according to claim 1, wherein the therapeutic antigen is chemically conjugated to the therapeutic antigen.

5. A pharmaceutical compound according to claim 1, wherein the therapeutic antigen is chemically conjugated to the therapeutic antigen as a fusion protein.

6. A method of making an immunotherapeutic polymer, said method comprising the steps of mixing a plurality of first subunits with a plurality of second subunits, wherein the first subunits are superantigens and the second subunits are immunotherapeutic antigens that are tumor specific antigens, crosslinking the first and second subunits in random combination.

7. An immunotherapeutic polymer made by the process of claim 6.

* * * * *